(12) United States Patent
Vermeij

(10) Patent No.: US 8,025,884 B2
(45) Date of Patent: Sep. 27, 2011

(54) *LAWSONIA INTRACELLULARIS* SUBUNIT VACCINES

(75) Inventor: Paul Vermeij, St. Anthonis (NL)

(73) Assignee: Intervet International B.V., Boxmeer (NL)

( * ) Notice: Subject to any disclaimer, the term of this patent is extended or adjusted under 35 U.S.C. 154(b) by 795 days.

(21) Appl. No.: 10/587,067

(22) PCT Filed: Jan. 18, 2005

(86) PCT No.: PCT/EP2005/000562
§ 371 (c)(1),
(2), (4) Date: Nov. 5, 2008

(87) PCT Pub. No.: WO2005/070958
PCT Pub. Date: Aug. 4, 2005

(65) Prior Publication Data
US 2009/0053228 A1 Feb. 26, 2009

(30) Foreign Application Priority Data

| Jan. 22, 2004 | (EP) | 04100202 |
| Jan. 22, 2004 | (EP) | 04100203 |
| Jan. 22, 2004 | (EP) | 04100204 |
| Jan. 22, 2004 | (EP) | 04100205 |
| Jan. 22, 2004 | (EP) | 04100206 |
| Jan. 22, 2004 | (EP) | 04100208 |
| Jan. 22, 2004 | (EP) | 04100209 |
| Jan. 22, 2004 | (EP) | 04100210 |
| Jan. 22, 2004 | (EP) | 04100211 |

(51) Int. Cl.
*A61K 39/00* (2006.01)
*A61K 39/49* (2006.01)
*C07H 21/04* (2006.01)

(52) U.S. Cl. .... 424/185.1; 424/9.1; 424/9.2; 424/184.1; 530/300; 530/350; 536/23.1; 536/23.7

(58) Field of Classification Search ............ 424/9.1, 424/9.2, 184.1, 185.1; 530/300, 350; 536/23.1, 536/23.7
See application file for complete search history.

(56) References Cited

U.S. PATENT DOCUMENTS
5,885,823 A   3/1999   Knittel et al.

FOREIGN PATENT DOCUMENTS
| EP | 1 094 070 A2 | 4/2001 |
| EP | 1 219 711 A2 | 3/2002 |
| WO | WO 00 69903 | 11/2000 |
| WO | WO 02 26250 A2 | 4/2002 |

*Primary Examiner* — Rodney P. Swartz
(74) *Attorney, Agent, or Firm* — William M. Blackstone

(57) ABSTRACT

The present invention relates i.a. to nucleic acids encoding novel *Lawsonia intracellularis* proteins. It furthermore relates to DNA fragments, recombinant DNA molecules and live recombinant carriers comprising these sequences. Also it relates to host cells comprising such nucleic acids, DNA fragments, recombinant DNA molecules and live recombinant carriers. Moreover, the invention relates to proteins encoded by these nucleotide sequences and to their use for the manufacturing of vaccines. The invention also relates to vaccines for combating *Lawsonia intracellularis* infections and methods for the preparation thereof. Finally the invention relates to diagnostic tests for the detection of *Lawsonia intracellularis* antigens and of antibodies against *Lawsonia intracellularis*.

7 Claims, 9 Drawing Sheets

LAWSONIA INTRACELLULARIS SUBUNIT VACCINES

Figure 1:
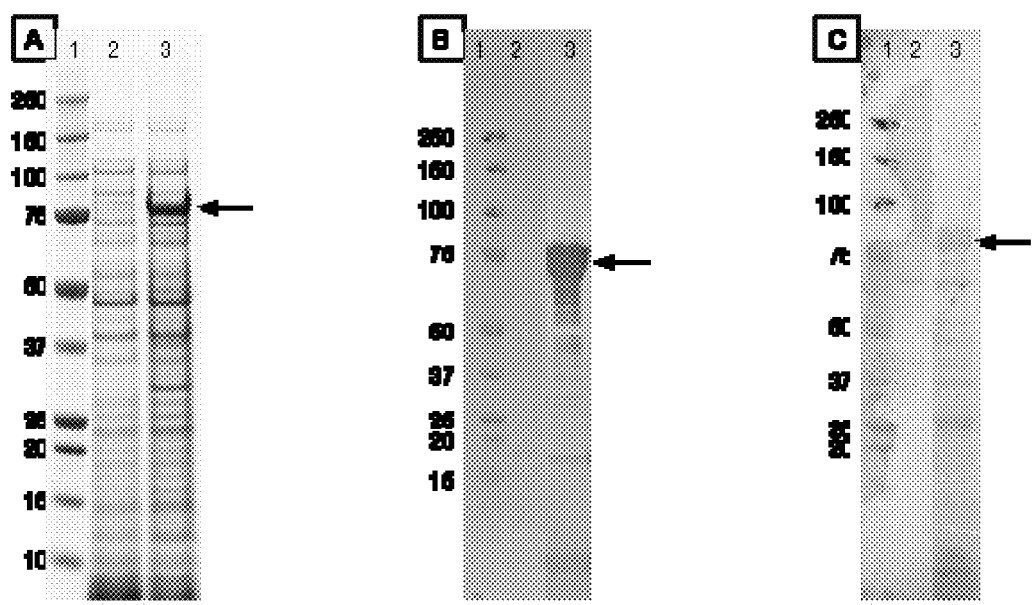

This application is the national stage of PCT/EP2005/000562, filed Jan. 18, 2005, which claims priority to EP Application 04100202.3, filed Jan. 22, 2004, EP Application 04100203.1, filed Jan. 22, 2004, EP Application 04100204.9, filed Jan. 22, 2004, EP Application 04100205.6, filed Jan. 22, 2004, EP Application 04100206.4, filed Jan. 22, 2004, EP Application 04100208.0, filed Jan. 22, 2004, EP Application 04100209.8, filed Jan. 22, 2004, EP Application 04100210.6, filed Jan. 22, 2004, and EP Application 04100211.4, filed Jan. 22, 2004, all of which are included herein in their entirety by reference.

REFERENCE TO SEQUENCE LISTING

The material saved on two identical compact discs (COPY 1 and COPY 2) under the file name Substitute Sequence Listing, created on Jul. 18, 2006, having a size of 108 KB is hereby incorporated by reference.

The present invention relates i.a. to nucleic acids encoding novel *Lawsonia intracellularis* proteins, to DNA fragments, recombinant DNA molecules and live recombinant carriers comprising these sequences, to host cells comprising such nucleic acids, DNA fragments, recombinant DNA molecules and live recombinant carriers, to proteins encoded by these nucleotide sequences and to their use for the manufacturing of vaccines, to vaccines for combating *Lawsonia intracellularis* infections and methods for the preparation thereof and to diagnostic tests for the detection of *Lawsonia intracellularis* antigens and for the detection of antibodies against *Lawsonia intracellularis*.

Porcine proliferative enteropathy (PPE or PE) has become an important disease of the modern pig industry world-wide. The disease affects 15% to 50% of the growing herds and up to 30% of the individual animals in established problem herds. Today annual economical losses have been estimated US $5-10 in extra feed and facility time costs per affected pig. PPE is a group of chronic and acute conditions of widely differing clinical signs (death, pale and anemic animals, watery, dark or bright red diarrhea, depression, reduced appetite and reluctance to move, and retarded growth). However there are two consistent features. The first, a pathological change only visible at necropsy, is a thickening of the small intestine and colon mucosa. The second is the occurrence of intracytoplasmatic small-curved bacteria in the enterocytes of the affected intestine. These bacteria have now been established as the etiological agent of PPE and have been named *Lawsonia intracellularis*.

Over the years *Lawsonia intracellularis* has been found to affect a large group of animals including monkeys, rabbits, ferrets, hamsters, fox, horses, and other animals as diverse as ostrich and emu. *Lawsonia intracellularis* is a gram-negative, flagellated bacterium that multiplies in eukaryotic enterocytes only and no cell-free culture has been described. In order to persist and multiply in the cell *Lawsonia intracellularis* must penetrate dividing crypt cells. The bacterium associates with the cell membrane and quickly enters the enterocyte via an entry vacuole. This then rapidly breaks down (within 3 hours) and the bacteria flourish and multiply freely in the cytoplasm. The mechanisms by which the bacteria cause infected cells to fail to mature, continue to undergo mitosis and form hypoplastic crypt cells is not yet understood.

The current understanding of *Lawsonia intracellularis* infection, treatment and control of the disease has been hampered by the fact that *Lawsonia intracellularis* can not be cultivated in cell-free media. Although there are reports of successful co-culturing *Lawsonia intracellularis* in rat enterocytes this has not led to the development of inactivated vaccines for combating *Lawsonia intracellularis*, although there clearly is a need for such vaccines.

It is an objective of the present invention to provide a vaccine for combating *Lawsonia intracellularis* infection.

It was surprisingly found now, that *Lawsonia intracellularis* produces nine novel proteins each of which is capable, separately or in combination with any of the other of these nine novel proteins, to induce protective immunity against *Lawsonia intracellularis*.

The first of these nine novel proteins will be referred to as the 751 kD protein. The amino acid sequence of the novel protein is presented in sequence identifier SEQ ID NO: 2. The gene encoding this protein has been sequenced and its nucleic acid sequence is shown in sequence identifier SEQ ID NO: 1. The gene will also be referred to in the Examples as "gene 5074".

The second of these nine novel proteins will be referred to as the 27 kD protein. The amino acid sequence of the novel protein is presented in sequence identifier SEQ ID NO: 4. The gene encoding this protein has been sequenced and its nucleic acid sequence is shown in sequence identifier SEQ ID NO: 3. The gene will also be referred to in the Examples as "gene 5669".

The third of these nine novel proteins will be referred to as the 62 kD protein. The amino acid sequence of the novel protein is presented in sequence identifier SEQ ID NO: 6. The gene encoding this protein has been sequenced and its nucleic acid sequence is shown in sequence identifier SEQ ID NO: 5. The gene will also be referred to in the Examples as "gene 4423".

The fourth of these nine novel proteins will be referred to as the 57 kD protein. The amino acid sequence of the novel protein is presented in sequence identifier SEQ ID NO: 8. The gene encoding this protein has been sequenced and its nucleic acid sequence is shown in sequence identifier SEQ ID NO: 7. The gene will also be referred to in the Examples as "gene 3123".

The fifth of these nine novel proteins will be referred to as the 74 kD protein. The amino acid sequence of the novel protein is presented in sequence identifier SEQ ID NO: 10. The gene encoding this protein has been sequenced and its nucleic acid sequence is shown in sequence identifier SEQ ID NO: 9. The gene will also be referred to in the Examples as "gene 5293".

The sixth of these nine novel proteins will be referred to as the 44 kD protein. The amino acid sequence of the novel protein is presented in sequence identifier SEQ ID NO: 12. The gene encoding this protein has been sequenced and its nucleic acid sequence is shown in sequence identifier SEQ ID NO: 11. The gene will also be referred to in the Examples as "gene 5464".

The seventh of these nine novel proteins will be referred to as the 43 kD protein. The amino acid sequence of the novel protein is presented in sequence identifier SEQ ID NO: 14. The gene encoding this protein has been sequenced and its nucleic acid sequence is shown in sequence identifier SEQ ID NO: 13. The gene will also be referred to in the Examples as "gene 5473".

The eighth of these nine novel proteins will be referred to as the 26/31 kD protein.

The amino acid sequence of the novel protein is presented in sequence identifier SEQ ID NO: 16. The gene encoding this protein has been sequenced and its nucleic acid sequence is shown in sequence identifier SEQ ID NO: 15. The gene will also be referred to in the Examples as "gene 4320".

The ninth of these nine novel proteins will be referred to as the 101 kD protein. The amino acid sequence of the novel protein is presented in sequence identifier SEQ ID NO: 18. The gene encoding this protein has been sequenced and its nucleic acid sequence is shown in sequence identifier SEQ ID NO: 17. The gene will also be referred to in the Examples as "gene 2008".

It is well-known in the art, that many different nucleic acid sequences can encode one and the same protein. This phenomenon is commonly known as wobble in the second and especially the third base of each triplet encoding an amino acid. This phenomenon can result in a meteorology of about 30% for two nucleic acid sequences still encoding the same protein. Therefore, two nucleic acid sequences having a sequence homology of about 70% can still encode one and the same protein.

Thus, one embodiment relates to nucleic acids encoding a *Lawsonia intracellularis* protein and to parts of that nucleic acid that encode an immunogenic fragment of that protein, wherein those nucleic acids or parts thereof have a level of homology with the nucleic acid of which the sequence is given in SEQ ID NO: 1 of at least 90%.

Preferably, the nucleic acid encoding this *Lawsonia intracellularis* protein or the part of said nucleic acid has at least 92%, preferably 94%, more preferably 95% and even more preferably 96% homology with the nucleic acid having the sequence given in SEQ ID NO: 1. Even more preferred is a homology level of 98% or even 100%.

The level of nucleotide homology can be determined with the computer program "BLAST 2 SEQUENCES" by selecting sub-program: "BLASTN." A reference for this program is Tatiana A. Tatusova, Thomas L. Madden FEMS Microbiol. Letters 174: 247-250 (1999). Parameters used are the default parameters: Reward for a match: +1. Penalty for a mismatch: −2. Open gap: 5. Extension gap: 2. Gap x_dropoff: 50.

Another approach for deciding if a certain nucleic acid is or is not a nucleic acid according to the invention relates to the question if that certain nucleic acid does hybridize under stringent conditions to nucleic acids having the nucleotide sequence as depicted in SEQ ID NO: 1.

If a nucleic acid hybridizes under stringent conditions to the nucleotide sequence as depicted in SEQ ID NO: 1, it is considered to be a nucleic acid according to the invention.

The definition of stringent conditions follows from the formula of Meinkoth and Wahl (1984. Hybridization of nucleic acids immobilized on solid supports. Anal. Biochem. 138: 267-284.)

$$Tm=[81.5°\ C.+16.6(\log M)+0.41(\%\ GC)-0.61(\%\ \text{formamide})-500/L]-1°\ C./1\%\ \text{mismatch}$$

In this formula, M is molarity of monovalent cations; % GC is the percentage of guanosine and cytosine nucleotides in the DNA; L is the length of the hybrid in base pairs.

Stringent conditions are those conditions under which nucleic acids or fragments thereof still hybridize, if they have a mismatch of 10% at the most, to the nucleic acid having the sequence depicted in SEQ ID NO: 1.

A second embodiment relates to nucleic acids encoding a *Lawsonia intracellularis* protein and to parts of that nucleic acid that encode an immunogenic fragment of that protein, wherein those nucleic acids or parts thereof have a level of homology with the nucleic acid of which the sequence is given in SEQ ID NO: 3 of at least 90%.

Preferably, the nucleic acid encoding this *Lawsonia intracellularis* protein or the part of said nucleic acid has at least 92%, preferably 94%, more preferably 95% and even more preferably 96% homology with the nucleic acid having the sequence given in SEQ ID NO: 3. Even more preferred is a homology level of 98% or even 100%.

A third embodiment relates to nucleic acids encoding a *Lawsonia intracellularis* protein and to parts of that nucleic acid that encode an immunogenic fragment of that protein, wherein those nucleic acids or parts thereof have a level of homology with the nucleic acid of which the sequence is given in SEQ ID NO: 5 of at least 90%.

Preferably, the nucleic acid encoding this *Lawsonia intracellularis* protein or the part of said nucleic acid has at least 92%, preferably 94%, more preferably 95% and even more preferably 96% homology with the nucleic acid having the sequence given in SEQ ID NO: 5. Even more preferred is a homology level of 98% or even 100%.

A fourth embodiment relates to nucleic acids encoding a *Lawsonia intracellularis* protein and to parts of that nucleic acid that encode an immunogenic fragment of that protein, wherein those nucleic acids or parts thereof have a level of homology with the nucleic acid of which the sequence is given in SEQ ID NO: 7 of at least 90%.

Preferably, the nucleic acid encoding this *Lawsonia intracellularis* protein or the part of said nucleic acid has at least 92%, preferably 94%, more preferably 95% and even more preferably 96% homology with the nucleic acid having the sequence given in SEQ ID NO: 7. Even more preferred is a homology level of 98% or even 100%.

A fifth embodiment relates to nucleic acids encoding a *Lawsonia intracellularis* protein and to parts of that nucleic acid that encode an immunogenic fragment of that protein, wherein those nucleic acids or parts thereof have a level of homology with the nucleic acid of which the sequence is given in SEQ ID NO: 9 of at least 90%.

Preferably, the nucleic acid encoding this *Lawsonia intracellularis* protein or the part of said nucleic acid has at least 92%, preferably 94%, more preferably 95% and even more preferably 96% homology with the nucleic acid having the sequence given in SEQ ID NO: 9. Even more preferred is a homology level of 98% or even 100%.

A sixth embodiment relates to nucleic acids encoding a *Lawsonia intracellularis* protein and to parts of that nucleic acid that encode an immunogenic fragment of that protein, wherein those nucleic acids or parts thereof have a level of homology with the nucleic acid of which the sequence is given in SEQ ID NO: 11 of at least 90%.

Preferably, the nucleic acid encoding this *Lawsonia intracellularis* protein or the part of said nucleic acid has at least 92%, preferably 94%, more preferably 95% and even more preferably 96% homology with the nucleic acid having the sequence given in SEQ ID NO: 11. Even more preferred is a homology level of 98% or even 100%.

A seventh embodiment relates to nucleic acids encoding a *Lawsonia intracellularis* protein and to parts of that nucleic acid that encode an immunogenic fragment of that protein, wherein those nucleic acids or parts thereof have a level of homology with the nucleic acid of which the sequence is given in SEQ ID NO: 13 of at least 90%.

Preferably, the nucleic acid encoding this *Lawsonia intracellularis* protein or the part of said nucleic acid has at least 92%, preferably 94%, more preferably 95% and even more preferably 96% homology with the nucleic acid having the sequence given in SEQ ID NO: 13. Even more preferred is a homology level of 98% or even 100%.

An eighth embodiment relates to nucleic acids encoding a *Lawsonia intracellularis* protein and to parts of that nucleic acid that encode an immunogenic fragment of that protein, wherein those nucleic acids or parts thereof have a level of homology with the nucleic acid of which the sequence is given in SEQ ID NO: 15 of at least 90%.

Preferably, the nucleic acid encoding this *Lawsonia intracellularis* protein or the part of said nucleic acid has at least 92%, preferably 94%, more preferably 95% and even more preferably 96% homology with the nucleic acid having the sequence given in SEQ ID NO: 15. Even more preferred is a homology level of 98% or even 100%.

A ninth embodiment relates to nucleic acids encoding a *Lawsonia intracellularis* protein and to parts of that nucleic acid that encode an immunogenic fragment of that protein, wherein those nucleic acids or parts thereof have a level of homology with the nucleic acid of which the sequence is given in SEQ ID NO: 17 of at least 90%.

Preferably, the nucleic acid encoding this *Lawsonia intracellularis* protein or the part of said nucleic acid has at least 92%, preferably 94%, more preferably 95% and even more preferably 96% homology with the nucleic acid having the sequence given in SEQ ID NO: 17. Even more preferred is a homology level of 98% or even 100%.

Since the present invention discloses nucleic acids encoding novel *Lawsonia intracellularis* proteins, it is now for the first time possible to obtain these proteins in sufficient quantities. This can e.g. be done by using expression systems to express the genes encoding the proteins.

Therefore, in a more preferred embodiment, the invention relates to DNA fragments comprising a nucleic acid according to the invention. Such DNA fragments can e.g. be plasmids, into which a nucleic acid according to the invention is cloned. Such DNA fragments are e.g. useful for enhancing the amount of DNA for use as a primer, as described below.

An essential requirement for the expression of the nucleic acid is an adequate promoter functionally linked to the nucleic acid, so that the nucleic acid is under the control of the promoter. It is obvious to those skilled in the art that the choice of a promoter extends to any eukaryotic, prokaryotic or viral promoter capable of directing gene transcription in cells used as host cells for protein expression.

Therefore, an even more preferred form of this embodiment relates to a recombinant DNA molecule comprising a DNA fragment or a nucleic acid according to the invention that is placed under the control of a functionally linked promoter. This can be accomplished by means of e.g. standard molecular biology techniques. (Sambrook, J. and Russell, D. W., Molecular cloning: a laboratory manual, 2001. ISBN 0-87969-577-3).

Functionally linked promoters are promoters that are capable of controlling the transcription of the nucleic acids to which they are linked.

Such a promoter can be a *Lawsonia* promoter e.g. the promoter involved in in vivo expression of any of the genes encoding the nine novel proteins, provided that that promoter is functional in the cell used for expression. It can also be a heterologous promoter. When the host cells are bacteria, useful expression control sequences which may be used include the Trp promoter and operator (Goeddel, et al., Nucl. Acids Res., 8, 4057, 1980); the lac promoter and operator (Chang, et al., Nature, 275, 615, 1978); the outer membrane protein promoter (Nakamura, K. and Inouge, M., EMBO J., 1, 771-775, 1982); the bacteriophage lambda promoters and operators (Remaut, E. et al., Nucl. Acids Res., 11, 4677-4688, 1983); the α-amylase (*B. subtilis*) promoter and operator, termination sequences and other expression enhancement and control sequences compatible with the selected host cell.

When the host cell is yeast, useful expression control sequences include, e.g., α-mating factor. For insect cells the polyhedrin or p10 promoters of baculoviruses can be used (Smith, G. E. et al., Mol. Cell. Biol. 3, 2156-65, 1983). When the host cell is of mammalian origin illustrative useful expression control sequences include the SV-40 promoter (Berman, P. W. et al., Science, 222, 524-527, 1983) or the metallothionein promoter (Brinster, R. L., Nature, 296, 39-42, 1982) or a heat shock promoter (Voellmy et al., Proc. Natl. Acad. Sci. USA, 82, 4949-53, 1985).

Bacterial, yeast, fungal, insect and mammalian cell expression systems are very frequently used systems. Such systems are well-known in the art and generally available, e.g. commercially through Invitrogen, Novagen or Clontech Laboratories, Inc. 4030 Fabian Way, Palo Alto, Calif. 94303-4607, USA. Next to these expression systems, parasite-based expression systems are very attractive expression systems. Such systems are e.g. described in the French Patent Application with Publication number 2 714 074, and in U.S. Ser. No. 08/043,109 (Hoffman, S, and Rogers, W.: Public. Date 1 Dec. 1993).

A still even more preferred form of this embodiment of the invention relates to Live Recombinant Carriers (LRCs) comprising a nucleic acid encoding any of the genes encoding the nine novel proteins or an immunogenic fragment thereof according to the invention, a DNA fragment according to the invention or a recombinant DNA molecule according to the invention. Such carriers are e.g. bacteria and viruses. These LRCs are micro-organisms or viruses in which additional genetic information, in this case a nucleic acid encoding any of the genes encoding the nine novel proteins or an immunogenic fragment thereof according to the invention has been cloned. Animals infected with such LRCs will produce an immunogenic response not only against the immunogens of the carrier, but also against the immunogenic parts of the protein(s) for which the genetic code is additionally cloned into the LRC, e.g. the 75 kD protein or any of the other proteins according to the invention.

As an example of bacterial LRCs, attenuated *Salmonella* strains known in the art can attractively be used.

Live recombinant carrier parasites have i.a. been described by Vermeulen, A. N. (Int. Journ. Parasitol. 28: 1121-1130 (1998))

Also, LRC viruses may be used as a way of transporting the nucleic acid into a target cell. Live recombinant carrier viruses are also called vector viruses. Viruses often used as vectors are Vaccinia viruses (Panicali et al; Proc. Natl. Acad. Sci. USA, 79: 4927 (1982), Herpesviruses (E.P.A. 0473210A2), and Retroviruses (Valerio, D. et al; in Baum, S. J., Dicke, K. A., Lotzova, E. and Pluznik, D. H. (Eds.), Experimental Haematology today—1988. Springer Verlag, New York: pp. 92-99 (1989)).

The technique of in vivo homologous recombination, well-known in the art, can be used to introduce a recombinant nucleic acid into the genome of a bacterium, parasite or virus of choice, capable of inducing expression of the inserted nucleic acid according to the invention in the host animal.

Finally another form of this embodiment of the invention relates to a host cell comprising a nucleic acid encoding a protein according to the invention, a DNA fragment comprising such a nucleic acid or a recombinant DNA molecule comprising such a nucleic acid under the control of a functionally linked promoter. This form also relates to a host cell containing a live recombinant carrier containing a nucleic acid molecule encoding any of the genes encoding the nine novel proteins or a fragment thereof according to the invention.

A host cell may be a cell of bacterial origin, e.g. *Escherichia coli, Bacillus subtilis* and *Lactobacillus* species, in combination with bacteria-based plasmids as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses.

Another embodiment of the invention relates to the novel proteins and to immunogenic fragments thereof according to the invention.

The concept of immunogenic fragments will be defined below.

One form of this embodiment relates i.a. to *Lawsonia intracellularis* proteins that have an amino acid sequence that is at least 90% homologous to the amino acid sequence as depicted in SEQ ID NO: 2 and to immunogenic fragments of said protein.

In a preferred form, the embodiment relates to such *Lawsonia intracellularis* proteins that have a sequence homology of at least 92%, preferably 94%, more preferably 96% homology to the amino acid sequence as depicted in SEQ ID NO: 2 and to immunogenic fragments of such proteins.

Even more preferred is a homology level of 98% or even 100%.

The level of protein homology can be determined with the computer program "BLAST 2 SEQUENCES" by selecting sub-program: "BLASTP."

A reference for this program is Tatiana A. Tatusova, Thomas L. Madden FEMS Microbiol. Letters 174: 247-250 (1999). Matrix used: "blosum62". Parameters used are the default parameters:

Open gap: 11. Extension gap: 1. Gap x_dropoff: 50.

It will be understood that, for the particular proteins embraced herein, natural variations can exist between individual *Lawsonia intracellularis* strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979) Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science, 227, 1435-1441, 1985) and determining the functional similarity between homologous proteins. Such amino acid substitutions of the exemplary embodiments of this invention, as well as variations having deletions and/or insertions are within the scope of the invention as long as the resulting proteins retain their immune reactivity.

This explains why *Lawsonia intracellularis* proteins according to the invention, when isolated from different field isolates, may have homology levels of about 90%, while still representing the same protein with the same immunological characteristics. Those variations in the amino acid sequence of a certain protein according to the invention that still provide a protein capable of inducing an immune response against infection with *Lawsonia intracellularis* or at least against the clinical manifestations of the infection are considered as "not essentially influencing the immunogenicity".

A second form of this embodiment relates i.a. to *Lawsonia intracellularis* proteins that have an amino acid sequence that is at least 90% homologous to the amino acid sequence as depicted in SEQ ID NO: 4 and to immunogenic fragments of said protein.

In a preferred form, the embodiment relates to such *Lawsonia intracellularis* proteins that have a sequence homology of at least 92%, preferably 94%, more preferably 96% homology to the amino acid sequence as depicted in SEQ ID NO: 4 and to immunogenic fragments of such proteins.

Even more preferred is a homology level of 98% or even 100%.

A third form of this embodiment relates i.a. to *Lawsonia intracellularis* proteins that have an amino acid sequence that is at least 90% homologous to the amino acid sequence as depicted in SEQ ID NO: 6 and to immunogenic fragments of said protein.

In a preferred form, the embodiment relates to such *Lawsonia intracellularis* proteins that have a sequence homology of at least 92%, preferably 94%, more preferably 96% homology to the amino acid sequence as depicted in SEQ ID NO: 6 and to immunogenic fragments of such proteins.

Even more preferred is a homology level of 98% or even 100%.

A fourth form of this embodiment relates i.a. to *Lawsonia intracellularis* proteins that have an amino acid sequence that is at least 90% homologous to the amino acid sequence as depicted in SEQ ID NO: 8 and to immunogenic fragments of said protein.

In a preferred form, the embodiment relates to such *Lawsonia intracellularis* proteins that have a sequence homology of at least 92%, preferably 94%, more preferably 96% homology to the amino acid sequence as depicted in SEQ ID NO: 8 and to immunogenic fragments of such proteins.

Even more preferred is a homology level of 98% or even 100%.

A fifth form of this embodiment relates i.a. to *Lawsonia intracellularis* proteins that have an amino acid sequence that is at least 90% homologous to the amino acid sequence as depicted in SEQ ID NO: 10 and to immunogenic fragments of said protein.

In a preferred form, the embodiment relates to such *Lawsonia intracellularis* proteins that have a sequence homology of at least 92%, preferably 94%, more preferably 96% homology to the amino acid sequence as depicted in SEQ ID NO: 10 and to immunogenic fragments of such proteins.

Even more preferred is a homology level of 98% or even 100%.

A sixth form of this embodiment relates i.a. to *Lawsonia intracellularis* proteins that have an amino acid sequence that is at least 90% homologous to the amino acid sequence as depicted in SEQ ID NO: 12 and to immunogenic fragments of said protein.

In a preferred form, the embodiment relates to such *Lawsonia intracellularis* proteins that have a sequence homology of at least 92%, preferably 94%, more preferably 96% homology to the amino acid sequence as depicted in SEQ ID NO: 12 and to immunogenic fragments of such proteins.

Even more preferred is a homology level of 98% or even 100%.

A seventh form of this embodiment relates i.a. to *Lawsonia intracellularis* proteins that have an amino acid sequence that is at least 90% homologous to the amino acid sequence as depicted in SEQ ID NO: 14 and to immunogenic fragments of said protein.

In a preferred form, the embodiment relates to such *Lawsonia intracellularis* proteins that have a sequence homology of at least 92%, preferably 94%, more preferably 96% homology to the amino acid sequence as depicted in SEQ ID NO: 14 and to immunogenic fragments of such proteins.

Even more preferred is a homology level of 98% or even 100%.

An eighth form of this embodiment relates i.a. to *Lawsonia intracellularis* proteins that have an amino acid sequence that is at least 90% homologous to the amino acid sequence as depicted in SEQ ID NO: 16 and to immunogenic fragments of said protein.

In a preferred form, the embodiment relates to such *Lawsonia intracellularis* proteins that have a sequence homology of at least 92%, preferably 94%, more preferably 96% homology to the amino acid sequence as depicted in SEQ ID NO: 16 and to immunogenic fragments of such proteins.

Even more preferred is a homology level of 98% or even 100%.

A ninth form of this embodiment relates i.a. to *Lawsonia intracellularis* proteins that have an amino acid sequence that is at least 90% homologous to the amino acid sequence as depicted in SEQ ID NO: 18 and to immunogenic fragments of said protein.

In a preferred form, the embodiment relates to such *Lawsonia intracellularis* proteins that have a sequence homology of at least 92%, preferably 94%, more preferably 96% homology to the amino acid sequence as depicted in SEQ ID NO: 18 and to immunogenic fragments of such proteins.

Even more preferred is a homology level of 98% or even 100%.

When a protein is used for e.g. vaccination purposes or for raising antibodies, it is however not necessary to use the whole protein. It is also possible to use a fragment of that protein that is capable, as such or coupled to a carrier such as e.g. KLH, of inducing an immune response against that protein, a so-called immunogenic fragment. An "immunogenic fragment" is understood to be a fragment of the full-length protein that still has retained its capability to induce an immune response in the host, i.e. comprises a B- or T-cell epitope. At this moment, a variety of techniques is available to easily identify DNA fragments encoding antigenic fragments (determinants). The method described by Geysen et al (Patent Application WO 84/03564, Patent Application WO 86/06487, U.S. Pat. No. 4,833,092, Proc. Natl. Acad. Sci. 81: 3998-4002 (1984), J. Imm. Meth. 102, 259-274 (1987), the so-called PEPSCAN method is an easy to perform, quick and well-established method for the detection of epitopes; the immunologically important regions of the protein. The method is used world-wide and as such well-known to one skilled in the art. This (empirical) method is especially suitable for the detection of B-cell epitopes. Also, given the sequence of the gene encoding any protein, computer algorithms are able to designate specific protein fragments as the immunologically important epitopes on the basis of their sequential and/or structural agreement with epitopes that are now known. The determination of these regions is based on a combination of the hydrophilicity criteria according to Hopp and Woods (Proc. Natl. Acad. Sci. 78: 38248-3828 (1981)), and the secondary structure aspects according to Chou and Fasman (Advances in Enzymology 47: 45-148 (1987) and U.S. Pat. No. 4,554,101). T-cell epitopes can likewise be predicted from the sequence by computer with the aid of Berzofsky's amphiphilicity criterion (Science 235, 1059-1062 (1987) and U.S. patent application Ser. No. 07/005, 885). A condensed overview is found in: Shan Lu on common principles: Tibtech 9: 238-242 (1991), Good et al on Malaria epitopes; Science 235: 1059-1062 (1987), Lu for a review; Vaccine 10: 3-7 (1992), Berzowsky for HIV-epitopes; The FASEB Journal 5:2412-2418 (1991).

Therefore, one form of still another embodiment of the invention relates to vaccines capable of protecting pigs against *Lawsonia intracellularis* infection, that comprise a protein or an immunogenic fragment thereof, according to the invention as described above together with a pharmaceutically acceptable carrier.

Still another embodiment of the present invention relates to the proteins according to the invention for use in a vaccine.

Still another embodiment relates to the use of a protein according to the invention for the manufacturing of a vaccine for combating *Lawsonia intracellularis* infections.

One way of making a vaccine according to the invention is by biochemical purification of the proteins or immunogenic fragments thereof according to the invention from bacteria obtained through mucosal scrapings taken from the infected intestine wall. This is however a very time-consuming way of making the vaccine.

It is therefore much more convenient to use the expression products of the genes encoding the proteins or immunogenic fragments thereof according to the invention in vaccines. The nucleic acid sequences of the genes encoding the nine novel proteins are provided by the present invention.

Such vaccines based upon the expression products of these genes can easily be made by admixing a protein according to the invention or an immunogenic fragment thereof according to the invention with a pharmaceutically acceptable carrier as described below.

Alternatively, a vaccine according to the invention can comprise live recombinant carriers as described above, capable of expressing the proteins according to the invention or immunogenic fragments thereof according to the invention. Such vaccines, e.g. based upon a *Salmonella* carrier or a viral carrier infecting the enteric epithelium, or e.g. the respiratory epithelium have the advantage over subunit vaccines that they better mimic the natural way of infection of *Lawsonia intracellularis*. Moreover, their self-propagation is an advantage since only low amounts of the recombinant carrier are necessary for immunization.

Vaccines described above all contribute to active vaccination, i.e. the host's immune system is triggered by a protein according to the invention or an immunogenic fragment thereof, to make antibodies against these proteins.

Alternatively, such antibodies can be raised in e.g. rabbits or can be obtained from antibody-producing cell lines as described below. Such antibodies can then be administered to the host animal. This method of vaccination, passive vaccination, is the vaccination of choice when an animal is already infected, and there is no time to allow the natural immune response to be triggered. It is also the preferred method for vaccinating immune-compromised animals. Administered antibodies against *Lawsonia intracellularis* can in these cases bind directly to the bacteria. This has the advantage that it immediately decreases or stops *Lawsonia intracellularis* growth. Therefore, one other form of this embodiment of the invention relates to vaccines comprising antibodies against at least one of the novel *Lawsonia intracellularis* proteins according to the invention.

Vaccines can also be based upon host cells as described above, that comprise the proteins or immunogenic fragments thereof according to the invention.

An alternative and efficient way of vaccination is direct vaccination with DNA encoding the relevant antigen. Direct vaccination with DNA encoding proteins has been successful for many different proteins. (As reviewed in e.g. Donnelly et al., The Immunologist 2: 20-26 (1993)).

This way of vaccination is very attractive for the vaccination of pigs against *Lawsonia intracellularis* infection.

Therefore, still other forms of this embodiment of the invention relate to vaccines comprising nucleic acids encoding a protein according to the invention or immunogenic fragments thereof according to the invention, and to vaccines comprising DNA fragments that comprise such nucleic acids.

Still other forms of this embodiment relate to vaccines comprising recombinant DNA molecules according to the invention.

DNA vaccines can easily be administered through intradermal application e.g. using a needle-less injector. This way of administration delivers the DNA directly into the cells of the animal to be vaccinated. Amounts of DNA in the microgram range between 1 and 100 μg provide very good results.

In a further embodiment, the vaccine according to the present invention additionally comprises one or more antigens derived from other pig pathogenic organisms and viruses, or genetic information encoding such antigens.

Such organisms and viruses are preferably selected from the group of Pseudorabies virus, Porcine influenza virus, Porcine parvo virus, Transmissible gastro-enteritis virus, Rotavirus, *Escherichia coli, Erysipelothrix rhusiopathiae, Bordetella bronchiseptica, Salmonella cholerasuis, Haemophilus parasuis, Pasteurella multocida, Streptococcus suis, Mycoplasma hyopneumoniae, Brachyspira hyodysenteriae* and *Actinobacillus pleuropneumoniae*.

All vaccines according to the present invention comprise a pharmaceutically acceptable carrier. A pharmaceutically acceptable carrier can be e.g. sterile water or a sterile physiological salt solution. In a more complex form the carrier can e.g. be a buffer.

Methods for the preparation of a vaccine comprise the admixing of a protein according to the invention, or an immunogenic fragment thereof, and a pharmaceutically acceptable carrier.

Vaccines according to the present invention may in a preferred presentation also contain an adjuvant. Adjuvants in general comprise substances that boost the immune response of the host in a non-specific manner A number of different adjuvants are known in the art. Examples of adjuvants are Freunds Complete and Incomplete adjuvant, vitamin E, non-ionic block polymers, muramyldipeptides, Quill A$^{(R)}$, mineral oil e.g. Bayol$^{(R)}$ or Markol$^{(R)}$, vegetable oil, and Carbopol $^{(R)}$ (a homopolymer), or Diluvac$^{(R)}$ Forte.

The vaccine may also comprise a so-called "vehicle". A vehicle is a compound to which the polypeptide adheres, without being covalently bound to it. Often used vehicle compounds are e.g. aluminium hydroxide, -phosphate or -oxide, silica, Kaolin, and Bentonite.

A special form of such a vehicle, in which the antigen is partially embedded in the vehicle, is the so-called ISCOM (EP 109.942, EP 180.564, EP 242.380)

In addition, the vaccine may comprise one or more suitable surface-active compounds or emulsifiers, e.g., SPAN or TWEEN. Often, the vaccine is mixed with stabilizers, e.g. to protect degradation-prone polypeptides from being degraded, to enhance the shelf-life of the vaccine, or to improve freeze-drying efficiency. Useful stabilizers are i.a. SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent.

It goes without saying, that other ways of adjuvanating adding vehicle compounds or diluents, emulsifying or stabilizing a polypeptide are also embodied in the present invention.

Vaccines according to the invention can very suitably be administered in amounts ranging between 1 and 100 micrograms, although smaller doses can in principle be used. A dose exceeding 100 micrograms will, although immunologically very suitable, be less attractive for commercial reasons.

Vaccines based upon live attenuated recombinant carriers, such as the LRC-viruses and bacteria described above can be administered in much lower doses, because they multiply themselves during the infection. Therefore, very suitable amounts would range between $10^3$ and $10^9$ CFU/PFU for respectively bacteria and viruses.

Many ways of administration can be applied. Oral application is a very attractive way of administration, because the infection is an infection of the digestive tract. A preferred way of oral administration is the packaging of the vaccine in capsules, known and frequently used in the art, that only disintegrate after they have passed the highly acidic environment of the stomach. Also, the vaccine could be mixed with compounds known in the art for temporarily enhancing the pH of the stomach. Systemic application is also suitable, e.g. by intramuscular application of the vaccine. If this route is followed, standard procedures known in the art for systemic application are well-suited.

From a point of view of protection against disease, a quick and correct diagnosis of *Lawsonia intracellularis* infection is important.

Therefore it is another objective of this invention to provide diagnostic tools suitable for the detection of *Lawsonia intracellularis* infection.

A diagnostic test for the detection of *Lawsonia intracellularis* antibodies in sera can be e.g. a simple standard sandwich-ELISA-test in which any of the novel proteins according to the invention or antigenic fragments thereof according to the invention are coated to the wall of the wells of an ELISA-plate. A method for the detection of such antibodies is e.g. incubation of the 75 kD protein (or any other protein according to the invention) or antigenic fragments thereof with serum from mammals to be tested, followed by e.g. incubation with a labelled antibody against the relevant mammalian antibody. A colour reaction can then reveal the presence or absence of antibodies against *Lawsonia intracellularis*. Another example of a diagnostic test system is e.g. the incubation of a Western blot comprising the 75 kD protein or an antigenic fragment thereof according to the invention, with serum of mammals to be tested, followed by analysis of the blot.

Thus, another embodiment of the present invention relates to diagnostic tests for the detection of antibodies against *Lawsonia intracellularis*. Such tests comprise a protein or a fragment thereof according to the invention.

A diagnostic test based upon the detection of antigenic material of any of the nine proteins of *Lawsonia intracellularis* antigens and therefore suitable for the detection of *Lawsonia intracellularis* infection can e.g. also be a standard ELISA test. In one example of such a test the walls of the wells of an ELISA plate are coated with antibodies directed against the 75 kD protein (or any other protein according to the invention). After incubation with the material to be tested, labelled anti-*Lawsonia intracellularis* antibodies are added to the wells. A colour reaction then reveals the presence of antigenic material from *Lawsonia intracellularis*.

Therefore, still another embodiment of the present invention relates to diagnostic tests for the detection of antigenic material of *Lawsonia intracellularis*. Such tests comprise antibodies against a protein or a fragment thereof according to the invention.

The polypeptides or immunogenic fragments thereof according to the invention expressed as characterized above can be used to produce antibodies, which may be polyclonal, monospecific or monoclonal (or derivatives thereof). If polyclonal antibodies are desired, techniques for producing and processing polyclonal sera are well-known in the art (e.g. Mayer and Walter, eds. *Immunochemical Methods in Cell and Molecular Biology*, Academic Press, London, 1987).

Monoclonal antibodies, reactive against the polypeptide according to the invention (or variants or fragments thereof) according to the present invention, can be prepared by immunizing inbred mice by techniques also known in the art (Kohler and Milstein, *Nature*, 256, 495-497, 1975).

Methods for large-scale production of antibodies according to the invention are also known in the art. Such methods rely on the cloning of (fragments of) the genetic information encoding the protein according to the invention in a filamentous phage for phage display. Such techniques are described i.a. in review papers by Cortese, R. et al., (1994) in Trends Biotechn. 12: 262-267., by Clackson, T. & Wells, J. A. (1994) in Trends Biotechn. 12: 173-183, by Marks, J. D. et al., (1992) in J. Biol. Chem. 267: 16007-16010, by Winter, G. et al., (1994) in Annu. Rev. Immunol. 12: 433-455, and by Little, M. et al., (1994) Biotechn. Adv. 12: 539-555. The phages are subsequently used to screen camelid expression libraries expressing camelid heavy chain antibodies. (Muyldermans, S, and Lauwereys, M., Journ. Molec. Recogn. 12: 131-140 (1999) and Ghahroudi, M. A. et al., FEBS Letters 414: 512-526 (1997)). Cells from the library that express the desired antibodies can be replicated and subsequently be used for large scale expression of antibodies.

EXAMPLES

Example 1

Isolation of *Lawsonia intracellularis* from Infected Porcine Ilea

*L. intracellularis* infected ilea, confirmed by histopathology and acid-fast Ziehl-Neelsen staining, were collected from pigs that died with PE, and stored at −80° C. After thawing *L. intracellularis* bacteria were isolated from mucosal scrapings taken from the infected intestinal wall. The ileal scrapings were homogenized repeatedly in PBS in an omnimixer to release the intracellular bacteria as described by Lawson et al. (Vet. Microbiol. 10: 303-323 (1985)). Supernatant obtained after low-speed centrifugation to remove cell debris was filtered through 5.0, 3.0, 1.2, and 0.8 μm filters (Millipore). The filtrate was subsequently centrifuged at 8000 g for 30 min, giving a small pellet of *L. intracellularis* bacteria. These bacteria were further purified using a Percoll gradient. The identity of the purified bacteria was assessed by PCR (Jones et al., J. Clin. Microbiol. 31: 2611-2615 (1993)) whereas purity of the isolated bacteria (>95%) was assessed by phase contrast microscopy to reveal any contaminating bacteria or gut debris present.

Bacterial Strains and Plasmids

*L. intracellularis* cells were isolated from infected ileal material as described above. *Escherichia coli* host strain BL21star(DE3) containing vector pLysSrare and plasmid pET-His-1 were purchased from Novagen (Madison, Wis., USA). *E. coli* strain TOP 10F' was purchased from Invitrogen (Groningen, the Netherlands). Stocks of all bacterial strains, containing 30% glycerol, were stored at −70° C.

Luria Bertani broth (LB) and LB plates were prepared according to standard procedures.

DNA Isolation

In order to obtain highly purified *L. intracellularis* chromosomal DNA, DNA was prepared from bacterial cells using a Biorad chromosomal DNA isolation kit (Biorad, Veenendaal, the Netherlands). Plasmid DNA was isolated using Qiagen products.

PCR Amplification

PCR amplification was performed using a PCR mixture containing 52 U/ml Expand High Fidelity Enzyme Mix (Roche Applied BioSciences), Expand HF buffer with 2.5 mM $MgCl_2$, 16 mM dNTPs (Promega, Wis., USA), 20 pmoles of primers and 15 ng chromosomal DNA of *L. intracellularis* as template.

For standard applications (i.e. colony PCR) the PCR mixture contained 20 U/ml Supertaq and Supertaq buffer (HT Biotechnology Ltd, Cambridge, UK), containing 8 mM dNTPs (Promega, Wis., USA), 10 pmoles of primers and 15 ng template.

Ligation and Transformation

Ligations were performed in a 1× ligation buffer with 1 unit of ligation enzyme (Gibco BRL Life Technologies Inc., USA) at 16° C. overnight. 1 μl of the ligation reaction was transformed to *E. coli* competent cells by heat shock. The BL21star(DE3) *E. coli* competent cells and the TOP10F' *E. coli* competent cells were made competent using standard methods.

Expression of 8×HIS Fusion Proteins

For the 75 kD, 27 kD, 62 kD and the 57 kD gene, the following expression method was used. The DNA sequence of the expression vector was confirmed by standard sequencing techniques before the expression vector was transformed to BL21star(DE3) containing pLysSrare. The resulting strain was grown overnight at 37° C. at 200 rpm in 5 ml LB with 100 μg/ml ampicillin. The overnight culture was diluted 1:100 in 50 ml LB with 100 μg/ml ampicillin. This culture was grown under the same conditions until the $OD_{600}$ reached 0.5. The culture was induced with IPTG to a final concentration of 1 mM and continued to grow for a subsequent 3 hours. 100 μl samples were taken for analysis. *E. coli* strain BL21star(DE3) containing pLysSrare was grown and induced under the same conditions and samples were taken as a negative control. The samples were analyzed by SDS page.

In Vitro Transcription and Translation

For the 74 kD, 44 kD, 43 kD, 26/31 kD and the 101 kD gene, the following expression method was followed. In vitro transcription and translation was performed using the Rapid Translation System from Roche Applied Science (Mannheim, FRG) according the manufacturer's protocol.

Summarizing, first the knowledge based sequence-optimization tool ProteoExpert RTS *E. coli* HY was used to design high yield variants of the original gene. This program optimizes the DNA template for the translation step by suggesting mutations in the DNA sequence. Only silent mutations were allowed, leading to identical amino-acid sequences on the protein level. However, changes of up to 8 nucleotides within the first 6 codons were proposed by the ProteoExpert service to give better expression results.

Ten sense and a universal antisense primers, containing a 5' overlapping region of 20 nucleotides and 30-38 additional gene-specific nucleotides, were used in 10 different PCR reactions to amplify these variants with purified *L. intracellularis* chromosomal DNA as template. The obtained amplicons were purified from gel and used for the generation of linear expression constructs for cell-free protein expression using the RTS *E. coli* Linear Template Generation Set, Histag, to introduce the necessary T7 regulatory elements.

Again the obtained amplicons were purified from gel, and after quantification, the appropriate amount of DNA was used for protein expression analysis in a 50-µl RTS 100 *E. coli* HY reaction mixture. Expression was analysed using Western blotting with an anti polyhistidine monoclonal antibody.

The construct that gave the highest protein yields was ligated to pCR2.1 TOPO TA vector using the TOPO TA cloning kit. The obtained plasmid was used for medium scale protein production using the RTS 500 *E. coli* HY kit. The samples were analyzed by SDS page and by Western blot.

The DNA sequence of the expression vector was confirmed using an ABI 310 automated sequencer (Applied Biosystems, California, USA).

If needed protein was purified using TALON immobilized metal affinity chromatography resin according to the protocol of the manufacturer for purification using denaturing conditions. Subsequently, the purified protein fraction was dialyzed against PBS to remove urea from the sample.

Polyacrylamide Gel Electrophoresis and Western Blotting

SDS-PAGE was performed using 4-12% Bis-Tris gels from the NuPAGE electrophoresis system (Invitrogen, www-.invitrogen.com). Western blotting was performed using semi dry blotting procedures. Western blots were developed using chicken anti-Lawsonia polyclonal serum that was raised against a whole cell preparation in a water:oil=45:55 emulsion or using a pig serum that had been obtained from a animal that been orally challenged with purified *L. intracellularis* cells and that had developed clinical signs and post-mortem lesions typical for *L. intracellularis* infection. The sera were pre-adsorbed using an equal volume crude cell extracts from BL21star(DE3) containing vector pLysSrare at 4° C. for 4 hours.

Results

Cloning of *L. intracellularis* Gene 5074 in T7 Based Expression Vector

Gene 5074 was amplified using primer 2075 (CATGCCATGGCTAGTCTTACAGCAGGAATGTG) [SEQ ID NO.: 19] and 2076 (CCGCTCGAGACACGCTTCATATTTACAACTG) [SEQ ID NO.: 20]. In the process a 5' NcoI and 3' XhoI site were introduced into the PCR product. The obtained PCR product was digested using restriction enzymes NcoI and XhoI. The digested PCR product was subsequently ligated to pET22b that had been cut with the same two restriction enzymes. The ligation mixture was transformed to *E. coli* TOP10F and incubated o/n at 37° C. Putative transformants were checked for the right plasmid, using colony PCR. The plasmid inserts, of colony PCR positive transformants, were checked by nucleotide sequence analysis. One of the clones that contained a sequence as expected on basis of the cloning strategy was chosen and designated pET5074.

Expression of *L. intracellularis* Gene 5074 from T7 Promoter in *E. coli*

Plasmid pET5074 was transformed to BL21Star(DE3) pLysSrare. The resulting strain was tested for recombinant protein production as described above. Samples of the induced culture and control samples were analysed by SDS-PAGE gel electrophoresis (FIG. 1A). A clear protein band of approximately 75 kD was observed in sample that had been taken after 3 hours of induction (FIG. 1A, lane 3) in comparison with the un-induced sample (FIG. 1A, lane 2).

The same samples were also analysed by western blot using the pig and chicken serum. A reaction with the 75 kD protein was observed using the serum from the pig that had been orally challenged with purified *L. intracellularis* cells (FIG. 1B, lane 3). and with the chicken anti-*L. intracellularis* serum (FIG. 1C, lane 3).

Conclusion: the 75 kD vaccine component could be successfully expressed in large quantities and is indeed clearly recognized by both orally challenged pig anti-*L. intracellularis* serum and by chicken anti-*L. intracellularis* serum Cloning of *L. intracellularis* Gene 5669 in T7 Based Expression Vector Gene 5669 was amplified using primer 2185 (CATGCCATGGATGCACTTGAGTTCATACAAGA) [SEQ ID NO.: 21] and 2186 (CCGCTCGAGATGAATTTGGATTTCAATTT) [SEQ ID NO.: 22]. In the process a 5' NcoI and 3' XhoI site were introduced into the PCR product. The obtained PCR product was digested using restriction enzymes NcoI and XhoI. The digested PCR product was subsequently ligated to pET22b that had been cut with the same two restriction enzymes. The ligation mixture was transformed to *E. coli* TOP10F and incubated o/n at 37° C. Putative transformants were checked for the right plasmid, using colony PCR. The plasmid inserts, of colony PCR positive transformants, were checked by nucleotide sequence analysis. One of the clones that contained a sequence as expected on basis of the cloning strategy was chosen and designated pET5669.

Expression of *L. intracellularis* Gene 5669 from T7 Promoter in *E. coli*

Plasmid pET5669 was transformed to BL21Star(DE3) pLysSrare. The resulting strain was tested for recombinant protein production as described above. Samples of the induced culture and control samples were analysed by SDS-PAGE gel electrophoresis (FIG. 2A). A clear protein band of approximately 27 kDa was observed in sample that had been taken after 3 hours of induction (FIG. 2A, lane 3) in comparison with the uninduced sample (FIG. 2A, lane 2).

The same samples were also analysed by western blot using the pig and chicken serum. A reaction with the 27 kD protein was observed using the serum from the pig that had been orally challenged with purified *L. intracellularis* cells (FIG. 2B, lane 3). and with the chicken anti-*L. intracellularis* serum (FIG. 2C, lane 3).

Conclusion: the 27 kD vaccine component could be successfully expressed in large quantities and is indeed clearly recognized by both orally challenged pig anti-*L. intracellularis* serum and by chicken anti-*L. intracellularis* serum Cloning of *L. intracellularis* Gene 4423 in T7 Based Expression Vector Gene 4423 was amplified using primer 2171 (CATGCCATGGATGCTAGCTATGTGGTTTTGCC) [SEQ ID NO.: 23] and 2172 (CCGCTCGAGGTTATCTTCAACAGCCTTAG) [SEQ ID NO.: 24]. In the process a 5' NcoI and 3' XhoI site were introduced into the PCR product. The obtained PCR product was digested using restriction enzymes NcoI and XhoI. The digested PCR product was subsequently ligated to pET22b that had been cut with the same two restriction enzymes. The ligation mixture was transformed to *E. coli* TOP10F and incubated o/n at 37° C. Putative transformants were checked for the right plasmid, using colony PCR. The plasmid inserts, of colony PCR positive transformants, were checked by nucleotide sequence analysis. One of the clones that contained a sequence as expected on basis of the cloning strategy was chosen and designated pET4423.

Expression of *L. intracellularis* Gene 4423 from T7 Promoter in *E. coli*

Plasmid pET4423 was transformed to BL21Star(DE3) pLysSrare. The resulting strain was tested for recombinant protein production as described above. Samples of the induced culture and control samples were analysed by SDS-PAGE gel electrophoresis (FIG. 3A). A clear protein band of approximately 62 kDa was observed in a sample that had been taken after 3 hours of induction (FIG. 3A, lane 3) in comparison with the uninduced sample (FIG. 3A, lane 2).

The same samples were also analysed by western blot using the pig serum. A reaction with the 62 kD protein was observed using the serum from the pig that had been orally challenged with purified *L. intracellularis* cells (FIG. 3B, lane 3).

Conclusion: the 62 kD vaccine component could be successfully expressed in large quantities and is indeed clearly recognized by orally challenged pig anti-L. intracellularis serum.

Cloning of *L. intracellularis* Gene 3123 in T7 Based Expression Vector

Gene 3123 was amplified using primer 2167 (CATGCCATGGATCAGTTTAATAAACCCTCTTT) [SEQ ID NO.: 25] and 2168 (CCGCTCGAGGGTTCGAC-CATGTACAAACT) [SEQ ID NO.: 26]. In the process a 5' NcoI and 3' XhoI site were introduced into the PCR product. The obtained PCR product was digested using restriction enzymes NcoI and XhoI. The digested PCR product was subsequently ligated to pET22b that had been cut with the same two restriction enzymes. The ligation mixture was transformed to *E. coli* TOP10F and incubated o/n at 37° C. Putative transformants were checked for the right plasmid, using colony PCR. The plasmid inserts, of colony PCR positive transformants, were checked by nucleotide sequence analysis. One of the clones that contained a sequence as expected on basis of the cloning strategy was chosen and designated pET3123.

Expression of *L. intracellularis* Gene 3123 from T7 Promoter in *E. coli*

Plasmid pET3123 was transformed to BL21Star(DE3) pLysSrare. The resulting strain was tested for recombinant protein production as described above. Samples of the induced culture and control samples were analysed by SDS-PAGE gel electrophoresis (FIG. 4A). A protein band of approximately 57 kDa was observed in sample that had been taken after 3 hours of induction (FIG. 4A, lane 3) in comparison with the uninduced sample (FIG. 4A, lane 2).

The same samples were also analysed by western blot using the pig serum. A reaction with the 57 kD protein was observed using the serum from the pig that had been orally challenged with purified *L. intracellularis* cells (FIG. 4B, lane 3).

Conclusion: the 57 kD vaccine component could be successfully expressed in large quantities and is indeed clearly recognized by whole-cell vaccinated pig anti-L. intracellularis serum.

Cloning of *L. intracellularis* Gene 5293

For the evaluation of the ProteoExpert suggestions, linear DNA templates were generated via PCR using the RTS Linear Template Generation Set. The primers used in these experiments also introduced a His6-tag at the C-terminus for detection and purification. The PCR-generated templates were examined for their expression performance using RTS 100 *E. coli* HY Kit. The suggested DNA sequence that gave the highest yields was constructed using primers 5293A5 and 5293B (Table 1) in the first PCR.

The obtained expression construct was ligated to pCR2.1 TOPO TA vector and the resulting vector was transformed to *E. coli* TOP10F and incubated o/n at 37° C. Putative transformants were checked for the right plasmid, using colony PCR. The plasmid inserts, of colony PCR positive transformants, were checked by nucleotide sequence analysis. One of the clones that contained a sequence as expected on basis of the cloning strategy was chosen and designated pTOPO5293.

TABLE 1

Sequence of the degenerated primers used for the amplification of gene 5293.

| Primer | Sequence |
|---|---|
| 5293A5 | CTTTAAGAAGGAGATATACCATGGCGGATTATTTAA [SEQ ID NO.: 27] |
| 5293B | GTGGTGGAATTTCTTITGGAGGTGATGATGAGAACC CCCCCCTGCACCAAGTTGCC [SEQ ID NO.: 28] |

Expression of *L. intracellularis* Gene 5293 Using RTS Technology

Plasmid pTOPO5293 was purified from *E. coli* TOP10F and the appropriate amount of DNA was added to a RTS500 vial. After incubation conform the protocol of the manufacturer, a sample was taken for analysis using SDS-PAGE gel electrophoresis (FIG. 5A). A clear protein band of approximately 74 kDa was observed in sample that had been taken after 30 hours of induction (FIG. 5A, lane 3) in comparison with the control sample (FIG. 5A, lane 2).

The same samples were also analysed by western blot using pig serum. The 74 kD protein was specifically recognized by the polyclonal pig serum used in this experiment (FIG. 5B, lane 3).

Conclusion: The 74 kD protein according to the invention can efficiently be expressed and is specifically recognized by the polyclonal pig serum. The 74 kD protein is an important vaccine component for the protection of pigs against *Lawsonia intracellularis* infection.

Cloning of *L. intracellularis* Gene 5464

For the evaluation of the ProteoExpert suggestions, linear DNA templates were generated via PCR using the RTS Linear Template Generation Set. The primers used in these experiments also introduced a His$_6$-tag at the C-terminus for detection and purification. The PCR-generated templates were examined for their expression performance using RTS100 *E. coli* HY Kit. The suggested DNA sequence that gave the highest yields was constructed using primers 5464A5 and 5464B (Table 2) in the first PCR.

The obtained expression construct was ligated to pCR2.1 TOPO TA vector and the resulting vector was transformed to *E. coli*t TOP10F and incubated o/n at 37° C. Putative transformants were checked for the right plasmid, using colony PCR. The plasmid inserts, of colony PCR positive transformants, were checked by nucleotide sequence analysis. One of the clones that contained a sequence as expected on basis of the cloning strategy was chosen and designated pTOPO5264.

TABLE 2

Sequence of the degenerated primers used for the amplification of gene 5464.

| Primer | Sequence |
|---|---|
| 5464A5 | CTTTAAGAAGGAGATATACCATGGCTAACGTATCAGGAAT TCCTGCACCACGATT [SEQ ID NO.: 29] |
| 5464B | TGATGATGAGAACCCCCCCCCTTGTATATTATTTTCATCTG [SEQ ID NO.: 30] |

Expression of *L. intracellularis* Gene 5464 Using RTS Technology

Plasmid pTOPO5464 was purified from *E. coli* TOP10F and the appropriate amount of DNA was added to an RTS500 vial. After incubation according to the protocol of the manufacturer, (Roche Diagnostics GmbH, Mannheim, Germany), a sample was taken for analysis using SDS-PAGE gel electrophoresis (FIG. 6A). A clear protein band of approximately 44 kDa was observed in sample that had been taken after 30 hours of induction (FIG. 6A, lane 3) in comparison with the control sample (FIG. 6A, lane 2). Using the anti-polyhistidine monoclonal in Western blot revealed a second reactive protein suggesting the presence of an internal translation start site in the gene or post translational modification of the mature protein (FIG. 6B, lane 3). A polyclonal serum was raised against purified 44 kD protein. In ELISA this serum specifically recognized purified whole *L. intracellularis* cells that were used as coating material with a reasonable titer (>2 log 9). Low titers were measured using a control serum (<2 log 3).

Conclusion: The 44 kD protein according to the invention can efficiently be expressed. Moreover, antiserum raised against the expressed protein is perfectly capable of recognizing *Lawsonia intracellularis* cells. The 44 kD protein is an important vaccine component for the protection of pigs against *Lawsonia intracellularis* infection.

Cloning of *L. intracellularis* Gene 5473

For the evaluation of the ProteoExpert suggestions, linear DNA templates were generated via PCR using the RTS Linear Template Generation Set. The primers used in these experiments also introduced a His6-tag at the C-terminus for detection and purification. The PCR-generated templates were examined for their expression performance using RTS100 *E. coli* HY Kit. The suggested DNA sequence that gave the highest yields was constructed using primers 5473A2 and 5473B (Table 3) in the first PCR.

The obtained expression construct was ligated to pCR2.1 TOPO TA vector and the resulting vector was transformed to *E. coli*t TOP10F and incubated o/n at 37° C. Putative transformants were checked for the right plasmid, using colony PCR. The plasmid inserts, of colony PCR positive transformants, were checked by nucleotide sequence analysis. One of the clones that contained a sequence as expected on basis of the cloning strategy was chosen and designated pTOPO5473.

TABLE 3

Sequence of the degenerated primers used for the amplification of gene 5473.

| Primer | Sequence |
|---|---|
| 5473A2 | CTTTAAGAAGGAGATATACCATGACAAATTTTGGAGA TATTAGCGGAAGCTCCG [SEQ ID NO.: 31] |
| 5473B | TGATGATGAGAACCCCCCCCCTCACGTGCACCA [SEQ ID NO.: 32] |

Expression of *L. intracellularis* Gene 5473 Using RTS Technology

Plasmid pTOPO5473 was purified from *E. coli* TOP10F and the appropriate amount of DNA was added to a RTS500 vial. After incubation according to the protocol of the manufacturer, (Roche Diagnostics GmbH, Mannheim, Germany), a sample was taken for analysis using SDS-PAGE gel electrophoresis (FIG. 7A). However, it was impossible to see whether the reaction mixture had produced a protein of around 40 kDa because the mixture already contains a dominant protein of around 40 kDa (FIG. 7A, lane 2 and 4). The RTS 500 reaction containing pTOPO5473 and the control mixture were loaded onto a IMAC column and proteins that had bound to the column were analyzed using SDS-PAGE. From the gel it appeared that a 43 kDa protein was eluted from the column (FIG. 7A, lane 5) that was not purified from the control sample (FIG. 7A, lane 3), so protein was expressed.

The same samples were also analysed by Western blot using pig-derived and chicken-derived *L. intracellularis* antiserum. A reaction with the 43 kD protein was observed both using serum from *L. intracellularis* bacterin vaccinated pigs (FIG. 7B, lane 5) and chickens (FIG. 7C, lane 5).

Conclusion: The 43 kD protein according to the invention can be efficiently expressed. Moreover, antiserum raised against *Lawsonia intracellularis* cells from both chickens and pigs recognizes the expressed protein. The 43 kD protein is an important vaccine component for the protection of pigs against *Lawsonia intracellularis* infection.

Cloning of *L. intracellularis* Gene 4320

For the evaluation of the ProteoExpert suggestions, linear DNA templates were generated via PCR using the RTS Linear Template Generation Set. The primers used in these experiments also introduced a His$_6$-tag at the C-terminus for detection and purification. The PCR-generated templates were examined for their expression performance using RTS100 *E. coli* HY Kit. The suggested DNA sequence that gave the highest yields was constructed using primers 4320A8 and 4320B (Table 4) in the first PCR.

The obtained expression construct was ligated to pCR2.1 TOPO TA vector and the resulting vector was transformed to *E. coli* TOP10F and incubated o/n at 37° C. Putative transformants were checked for the right plasmid, using colony PCR. The plasmid inserts, of colony PCR positive transformants, were checked by nucleotide sequence analysis. One of the clones that contained a sequence as expected on basis of the cloning strategy was chosen and designated pTOPO4320.

TABLE 4

Sequence of the degenerated primers used for the amplification of gene 4320.

| Primer | Sequence |
|---|---|
| 4320A8 | CTTTAAGAAGGAGATATACCATGAGCTTAGTAATT AACAATAACCTGATGGCCG [SEQ ID NO.: 33] |
| 4320B | TGATGATGAGAACCCCCCCCGCCAATAAGTTGCTG [SEQ ID NO.: 34] |

Expression of *L. intracellularis* Gene 4320 Using RTS Technology

Plasmid pTOPO4320 was purified from *E. coli* TOP10F and the appropriate amount of DNA was added to an RTS500 vial. After incubation according to the protocol of the manufacturer, (Roche Diagnostics GmbH, Mannheim, Germany), a sample was taken for analysis using SDS-PAGE gel electrophoresis (FIG. 8A). Two clear protein bands of approximately 31 and 26 kDa were observed in sample that had been taken after 30 hours of induction (FIG. 8A, lane 3) in comparison with the control sample (FIG. 8A, lane 2). Both bands reacted with an anti-polyhistidine monoclonal suggesting the presence of an internal translation start site in the gene or post translational modification of the mature protein (FIG. 8B, lane 2). Using polyclonal pig and chicken sera, high titers (>2 log 10) were observed in an ELISA using purified 26/31 kD protein and purified whole L. intracellularis cells as coating material. Using IHC we found that polyclonal anti-26/31 kD protein specifically recognized L. intracellularis infected enterocytes, whereas no reaction was seen in with specimens cut from the ilia of healthy pigs. The serum used in IHC also gave high titers (>2 log 15) against whole L. intracellularis cells in ELISA.

Conclusion: The 26/31 kD protein according to the invention can be efficiently expressed. Moreover, antiserum raised against Lawsonia intracellularis cells from both chickens and pigs recognizes the expressed protein in ELISA tests, where the wells were coated with the 26/31 kD protein.

Moreover, polyclonal anti-serum raised against the 26/31 kD protein specifically recognized L. intracellularis infected enterocytes.

The 26/31 kD protein is an important vaccine component for the protection of pigs against Lawsonia intracellularis infection.

Cloning of L. intracellularis Gene 2008

Sequence analysis of gene 2008 had revealed that the gene encoded a putative N-terminal signal sequence and a C-terminal beta-barrel structure. Both structures are known to be very hydrophobic. Because the RTS system has been found unsuitable for the expression of proteins that contain large hydrophobic regions it was decided to amplify gene 2008 from base 37 to 1958. Expression of this gene fragment resulted in a protein of 63 kD.

For the evaluation of the ProteoExpert suggestions, linear DNA templates were generated via PCR using the RTS Linear Template Generation Set. The primers used in these experiments also introduced a His$_6$-tag at the C-terminus for detection and purification. The PCR-generated templates were examined for their expression performance using RTS 100 E. coli HY Kit. The suggested DNA sequence that gave the highest yields was constructed using primers 2008A6 and 2008B (Table 5) in the first PCR.

The linear expression construct was ligated to pCR2.1 TOPO TA vector and the resulting vector was transformed to E. coli TOP10F and incubated o/n at 37° C. Putative transformants were checked for the right plasmid, using colony PCR. The plasmid inserts, of colony PCR positive transformants, were checked by nucleotide sequence analysis. One of the clones that contained a sequence as expected on basis of the cloning strategy was chosen and designated pTOPO2008.

TABLE 5

Sequence of the degenerated primers used for the amplification of gene 2008.

| Primer | Sequence |
| --- | --- |
| 2008A6 | CTTTAAGAAGGAGATATACCATGGCAGATGTATTTTTCG AAGGCAGAACCGAAAC [SEQ ID NO.: 35] |
| 2008B | TGATGATGAGAACCCCCCCCATTAACATACCAAATAGAT [SEQ ID NO.: 36] |

Expression of L. intracellularis Gene 2008 Using RTS Technology

Plasmid pTOPO2008 was purified from E. coli TOP10F and the appropriate amount of DNA was added to an RTS500 vial. After incubation according to the protocol of the manufacturer, (Roche Diagnostics GmbH, Mannheim, Germany), a sample was taken for analysis using SDS-PAGE gel electrophoresis (FIG. 9A). A clear protein band of approximately 63 kDa was observed in sample that had been taken after 30 hours of induction (FIG. 9A, lane 3) in comparison with the control sample (FIG. 9A, lane 2).

The same samples were also analysed by western blot using both pig- and chicken-antiserum. A strong reaction with the 63 kD protein was observed using both the polyclonal pig (FIG. 9B, lane 3) and chicken serum (FIG. 9C, lane 3).

Concusion: the 63 kD fragment of the protein according to the invention can efficiently be expressed. Moreover, the 63 kD protein fragment is strongly and equally well recognized by both chicken- and pig-antiserum against Lawsonia intracellularis cells.

The 101 kD protein according to the invention and the 63 kD protein fragment thereof are important vaccine components for the protection of pigs against Lawsonia intracellularis infection.

Example 2

The objective of this experiment was to test for active protection in pigs induced by experimental Lawsonia recombinant combi subunit vaccine comprising the 75 kD, 44 kD, 26/31 kD and the 27 kD protein.

Vaccine

Inactivated recombinant subunit combi vaccine in microDiluvac Forte.

The following antigens were incorporated: 75 kD, 44 kD, 26/31 kD and the 27 kD protein. The mixture of recombinant antigens was dialyzed against a dialysis buffer (50 mM Tris-HCl pH8.0, 100 mM NaCl, 1 mM EDTA, 1 mM oxidized glutathione, 3 mM reduced glutathione, 10 mM CHAPS) and concentrated using PEG20,000. The concentration of all antigens was estimated from Coomassie stained NuPage gel using Gene Tools software (Syngene, Cambridge, England). The antigens were formulated in the vaccine at a concentration of 50 µg of every single antigen per ml.

Experimental Design

Eighteen 6-week-old SPF pigs (3 groups of 6 pigs each) were used for the experiment. Group 1 pigs were vaccinated intramuscularly (neck) with 2 ml of the recombinant combi subunit vaccine at T=0 and T=4w. Group 2 was left as nonvaccinated challenge control group. Group 3 was a nontreated performance control group. At T=6w (12 weeks of age) groups 1 and 2 were challenged orally with homogenized infected mucosa. Subsequently all pigs were daily observed for clinical signs of Porcine Proliferative Enteropathy (PPE) during 3 weeks. At T=9w (15-week-old) all remaining pigs were euthanized and post-mortem examined. The intestines (ileum) were examined for macroscopical changes typical for Lawsonia intracellularis infection and samples were taken for histological examination.

Preparation of Challenge Material

Challenge material was prepared by scraping the mucosa of the ileum of confirmed PPE cases. The material was stored in batches of 200 grams at −20° C. ntil further use. Shortly before challenge, 200 gram of the infected mucosa was thawed and mixed with 200 ml physiological salt solution. This mixture was homogenized in an omnimixer for one minute at full speed and then further diluted with 400 ml physiological salt solution (up to 800 ml).

Vaccination

The pigs were assigned to 3 treatment groups as described below.

| Group | Number | Unit | Vaccine | Dose | Route | Time in weeks |
|---|---|---|---|---|---|---|
| 1 | 6 | 5 | Sub-unit vaccine | 2 ml | IM | T = 0 and T = 4 |
| 2 | 6 | 5 | Non-vaccinated Challenge control | — | — | — |
| 3 | 6 | 12 | Non-vaccinated Negative control | — | — | — |

Challenge

Group 1 and 2 were challenged orally with 20 ml challenge inoculum at T=6w (12 weeks of age). Group 3 was left as a non-treated control group.

Post-Mortem Examination and Histopathology

All pigs were killed at T=9w (15 weeks of age, 3 weeks after challenge) and subjected to a post-mortem examination to assess the efficacy of the different vaccines.

| | |
|---|---|
| — | Normal |
| 1 | minimal to mild redness/erosions without thickening of mucosa over limited area |
| 2 | mild to moderate redness/erosions and/or thickening of mucosa over limited area |
| 3 | moderate redness/erosions and/or thickening of mucosa over extended area |
| 4 | moderate to severe redness/erosions and/or ulceration and/or severe thickening of mucosa and intestinal wall over extended area |

From each pig at least one sample of the ileum (if present from an affected area) was taken for histology.

Histologic scoring of ileum samples was based on:
a) Presence of *L. intracellularis* bacteria in slides: Warthin Starry was performed for detection of bacteria.
b) Evaluation of histologic lesions in Hematoxylin/Eosin slides: Severity of *L. intracellularis*-specific lesion (adenomatous glandular proliferation) was scored. Other lesions are described.

| Histologic lesion | | Warthin Starry | HE lesion score | Remark |
|---|---|---|---|---|
| No abnormalities detected | | 0 | 0 | |
| Adenomatous glandular proliferation | mild (multi)focal | 2 | 1 | Typical PPE |
| | moderate diffuse or multifocal | 2 | 2 | |
| | severe diffuse | 2 | 3 | |
| Other lesions (not going along with adenomatous proliferation) | | 0/1 | | Lesion is described |

Warthin Starry:
0: no bacteria evident
1: presence of single/small numbers of bacteria within lesion
2: presence of considerable numbers of bacteria within lesion Evaluation of Results All data were recorded for each pig individually. The mean score per group was calculated for the parameters histopathology score and post-mortem score. Starting from the score of the challenge control group, the % protection in the vaccinated was calculated. Pathology scores were compared using two-sided Mann-Whitney U test.

Results

Post-Mortem and Histology

Post-mortem results after challenge are shown in Table 6. Histopathological scores showed clear cut results. Only the control pigs showed the typical histopathological lesions (=severe diffuse adenomatous glandular proliferation) and only the enterocytes in the control histopathology slides contained numerous *Lawsonia* bacteria, whereas no bacteria were observed in the enterocytes of the vaccinated and non-challenged animals.

Conclusion

The post-mortem and histopathological examination gave clear cut results. The subunit vaccine tested appeared to induce 100% protection against histopathological lesions and the occurrence of *Lawsonia* in the enterocytes (=against infection).

Table 6 Post-Mortem Examination 3 Weeks After Challenge (T=9w)

TABLE 1

Post-mortem examination 3 weeks after challenge (T = 9 w)

| | | Macroscopically | Histo-pathological scores Histological | | |
|---|---|---|---|---|---|
| group | pig # | ileum | WS | HE | remarks/description |
| 1 sububit in µ-DF IM route 2x | 177 | 3 | 0 | 0 | NAD |
| | 180 | 2 | 0 | 0 | NAD |
| | 356 | 3 | 0 | 0 | one crypt abscess, one focus of mild GP |
| | 361 | 0 | 0 | 0 | NAD |
| | 378 | 2 | 0 | 0 | mild focal GP, thick tunica muscularis |
| | 385 | 2 | 0 | 0 | mild focal GP, thick tunica muscularis |
| | total | 12 | 0 | 0 | |
| | p-value[a] | 0.054 | | 0.000 | |
| 2 challenge control | 181 | 4 | 2 | 3 | severe diffuse adematous GP |
| | 193 | 3 | 2 | 2 | moderate diffuse adematous GP |
| | 194 | 3 | 2 | 3 | severe diffuse adematous GP |
| | 195 | 4 | 2 | 3 | severe diffuse adematous GP |

TABLE 1-continued

Post-mortem examination 3 weeks after challenge (T = 9 w)

| group | pig # | Histo-pathological scores | | | remarks/description |
|---|---|---|---|---|---|
| | | Macroscopically ileum | Histological WS | HE | |
| | 351 | 2 | NS | NS | NS |
| | 376 | 4 | 2 | 3 | severe diffuse adematous GP |
| | total | 20 | 10 | 14 | |
| 3 | 173 | 2 | 0 | 0 | NAD |
| untreated | 174 | 2 | 0 | 0 | NAD |
| contact | 179 | 0 | 0 | 0 | NAD |
| controls | 183 | 1 | 0 | 0 | NAD |
| | 200 | 1 | 0 | 0 | NAD |
| | 388 | 0 | 0 | 0 | NAD |
| | total | 6 | 0 | 0 | |
| | p-value[a] | 0.008 | | 0.000 | |

[a] two-sided Mann-Whitney U test (compared to control group 3)
WS = Warthin Starry staining,
HE = haematoxilin-eosin staining,
NAD = no abnormality detected,
NS = no sample
GP = glandular proliferation,
MFPC = multifocal propria congestion
N.B. all group 4 pigs showed (macroscopically) congestion of lymph vessels Legend to the Figure.

FIG. 1. Analysis of the over-expression of *Lawsonia intracellularis* gene 5074 in *Escherichia coli* t BL21STAR/pLysS-RARE by SDS-PAGE (A) and Western blotting with polyclonal pig serum (B) and polyclonal chicken serum (C). Lane 1, molecular weight marker; lane 2, pET5074 T=0; lane 3, pET5074 T=3. Arrows indicate the location of the expression product.

Figure 2:
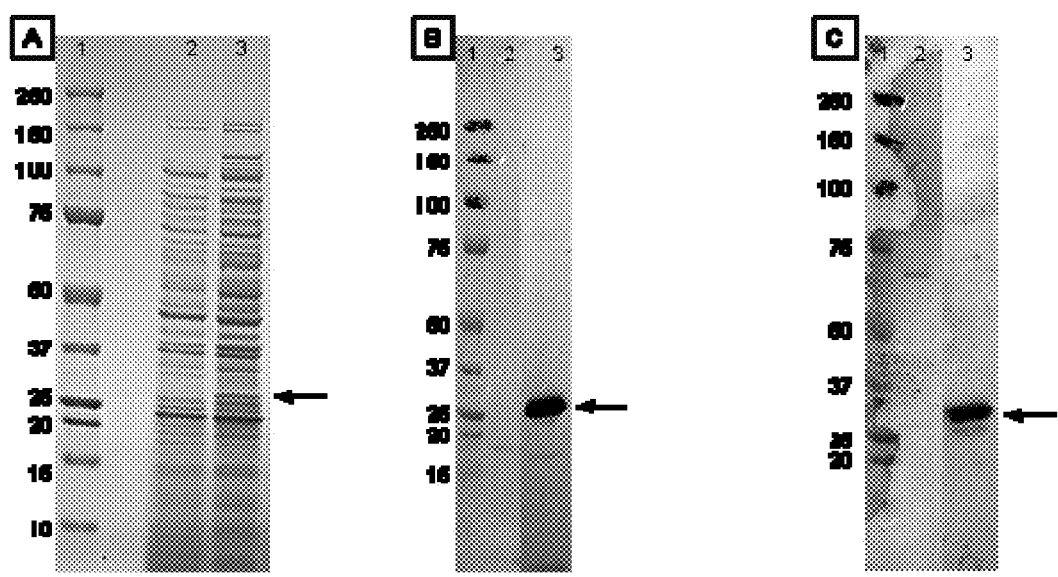

FIG. 2. Analysis of the over-expression of *Lawsonia intracellularis* gene 5669 in *Escherichia coli* t BL21STAR/pLysS-RARE by SDS-PAGE (A) and Western blotting with polyclonal pig serum (B) and polyclonal chicken serum (C). Lane 1, molecular weight marker; lane 2, pET5669 T=0; lane 3, pET5669 T=3. Arrows indicate the location of the expression product.

Figure 3:
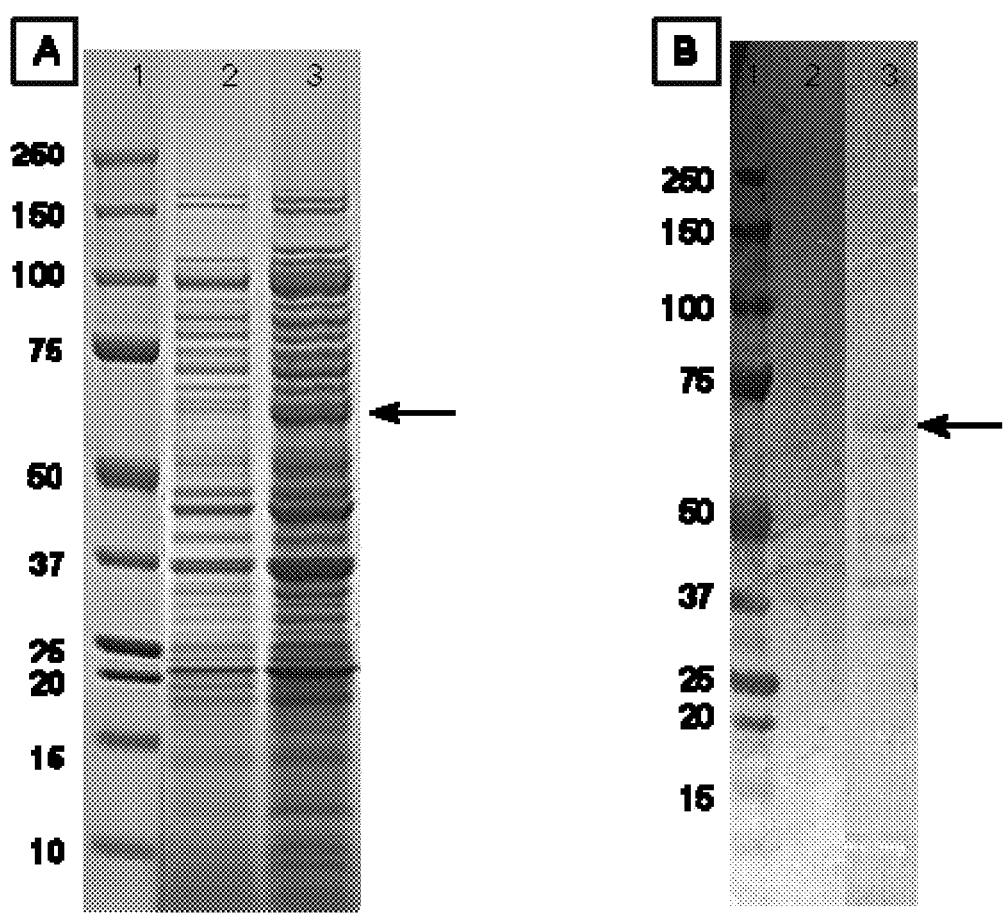

FIG. 3. Analysis of the over-expression of *Lawsonia intracellularis* gene 4423 in *Escherichia coli* t BL21STAR/pLysS-RARE by SDS-PAGE (A) and Western blotting with polyclonal pig serum (B). Lane 1, molecular weight marker; lane 2, pET4423 T=0; lane 3, pET4423 T=3. Arrows indicate the location of the expression product.

Figure 4:
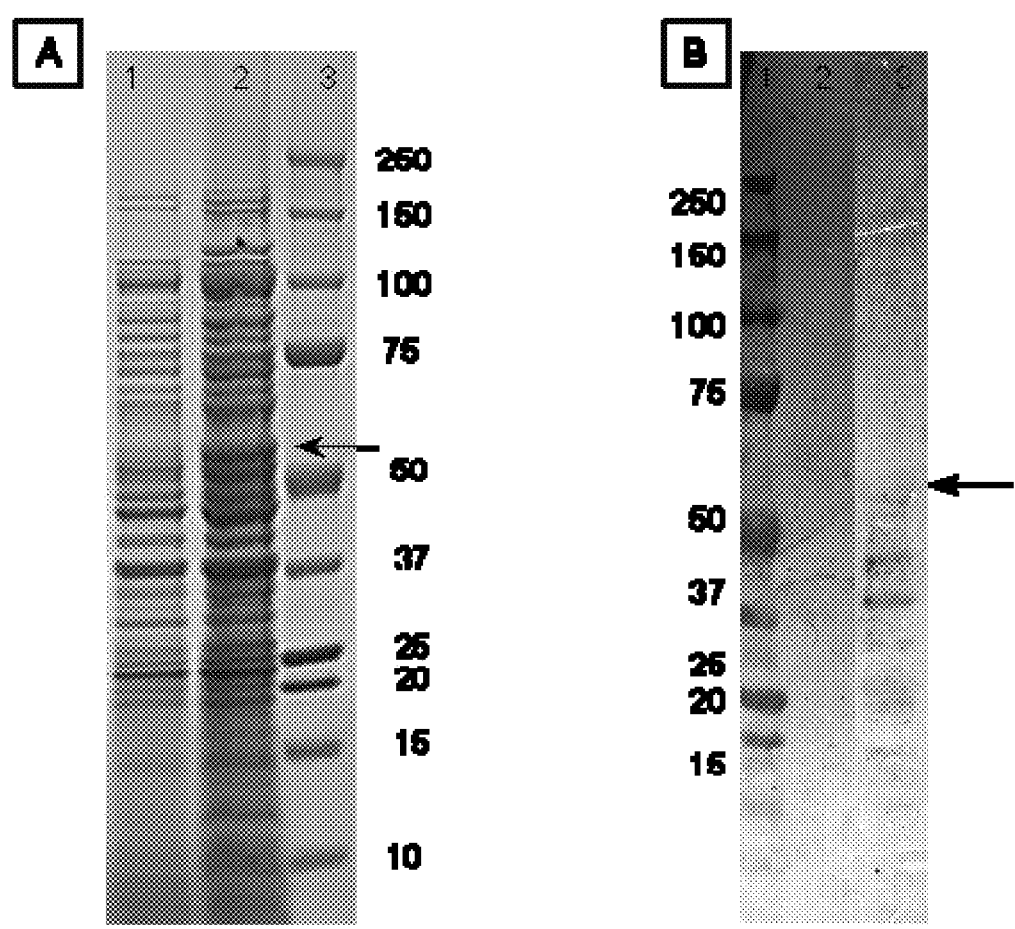

FIG. 4. Analysis of the over-expression of *Lawsonia intracellularis* gene 3123 in *Escherichia coli* t BL21STAR/pLysS-RARE by SDS-PAGE (A) and Western blotting with polyclonal pig serum (B). Lane 1, molecular weight marker; lane 2, pET3123 T=0; lane 3, pET3123 T=3. Arrows indicate the location of the expression product.

Figure 5:
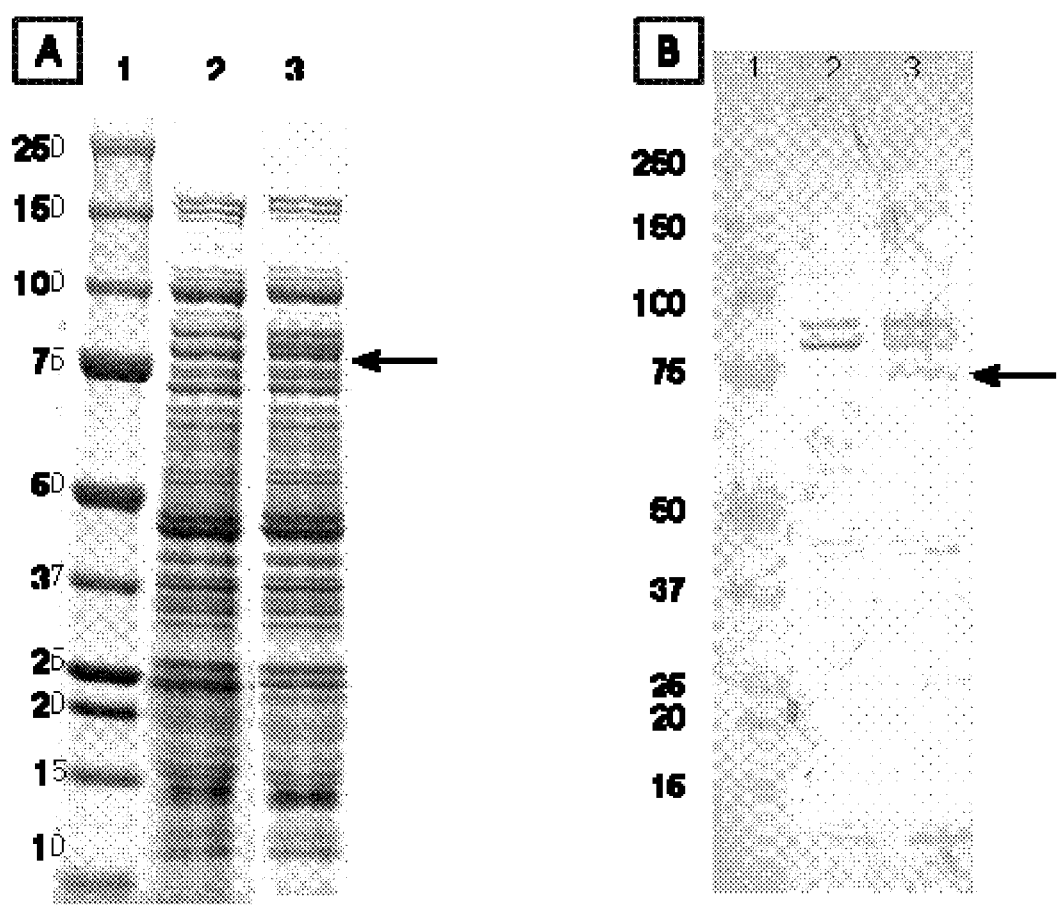

FIG. 5. Analysis of the expression of *Lawsonia intracellularis* gene 5293 using RTS500 technology by SDS-PAGE (A) and Western blotting with polyclonal pig serum (B). Lane 1, molecular weight marker; lane 2, control; lane 3, pET5293 Arrows indicate the location of the expression product.

Figure 6:
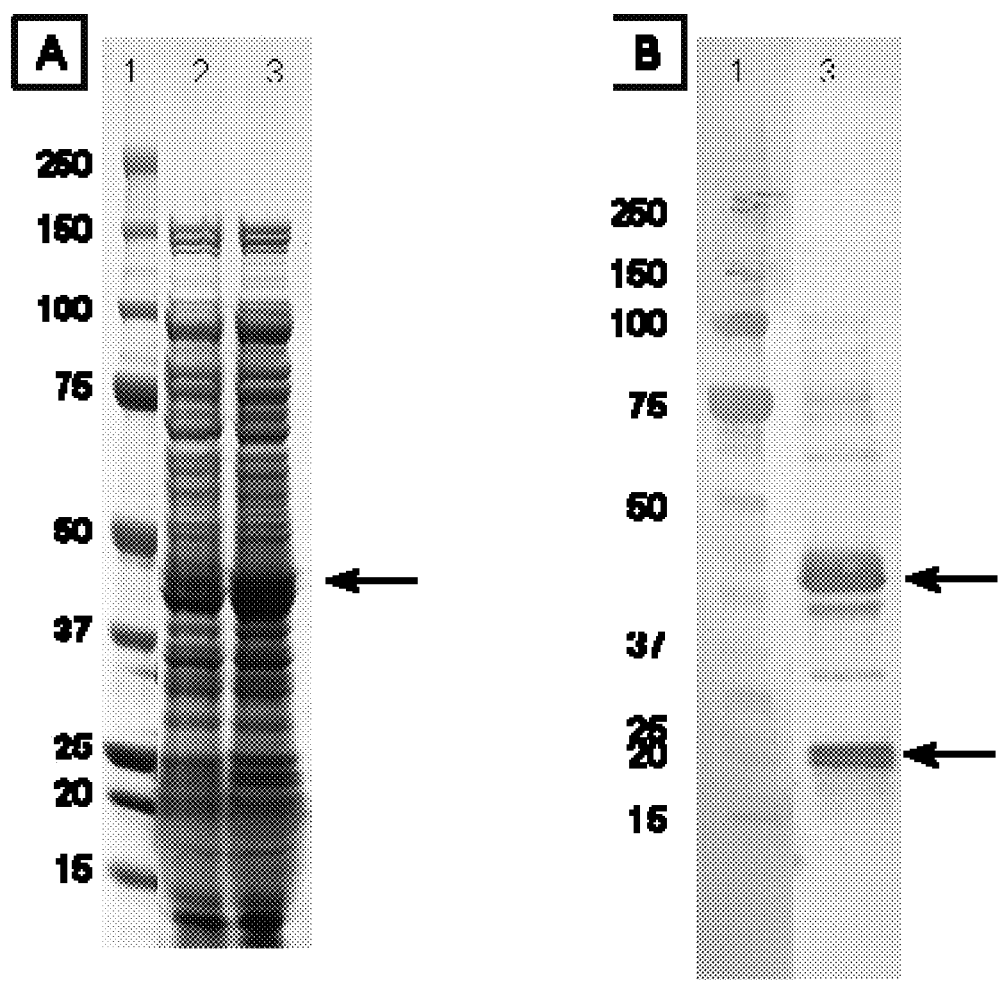

FIG. 6. Analysis of the expression of *Lawsonia intracellularis* gene 5464 using RTS500 technology by SDS-PAGE (A) and Western blotting using anti-polyhistidine monoclonal (B). Lane 1, molecular weight marker; lane 2, control; lane 3, pET5464 Arrows indicate the location of the expression product.

Figure 7:
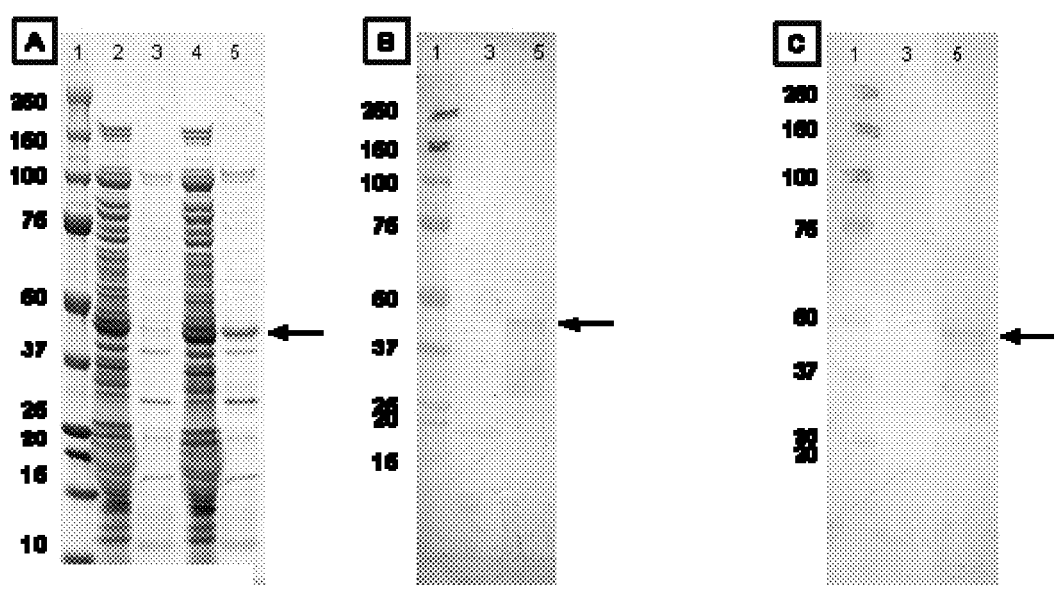

FIG. 7. Analysis of the expression of *Lawsonia intracellularis* gene 5473 using RTS500 technology by SDS-PAGE (A) and Western blotting with polyclonal pig serum (B) and polyclonal chicken serum(C). Lane 1, molecular weight marker; lane 2, control; lane 3, bound protein fraction IMAC purification control sample; lane 4 pET5473; lane 5, bound protein fraction IMAC purification pET5473. Arrows indicate the location of the expression product.

Figure 8:
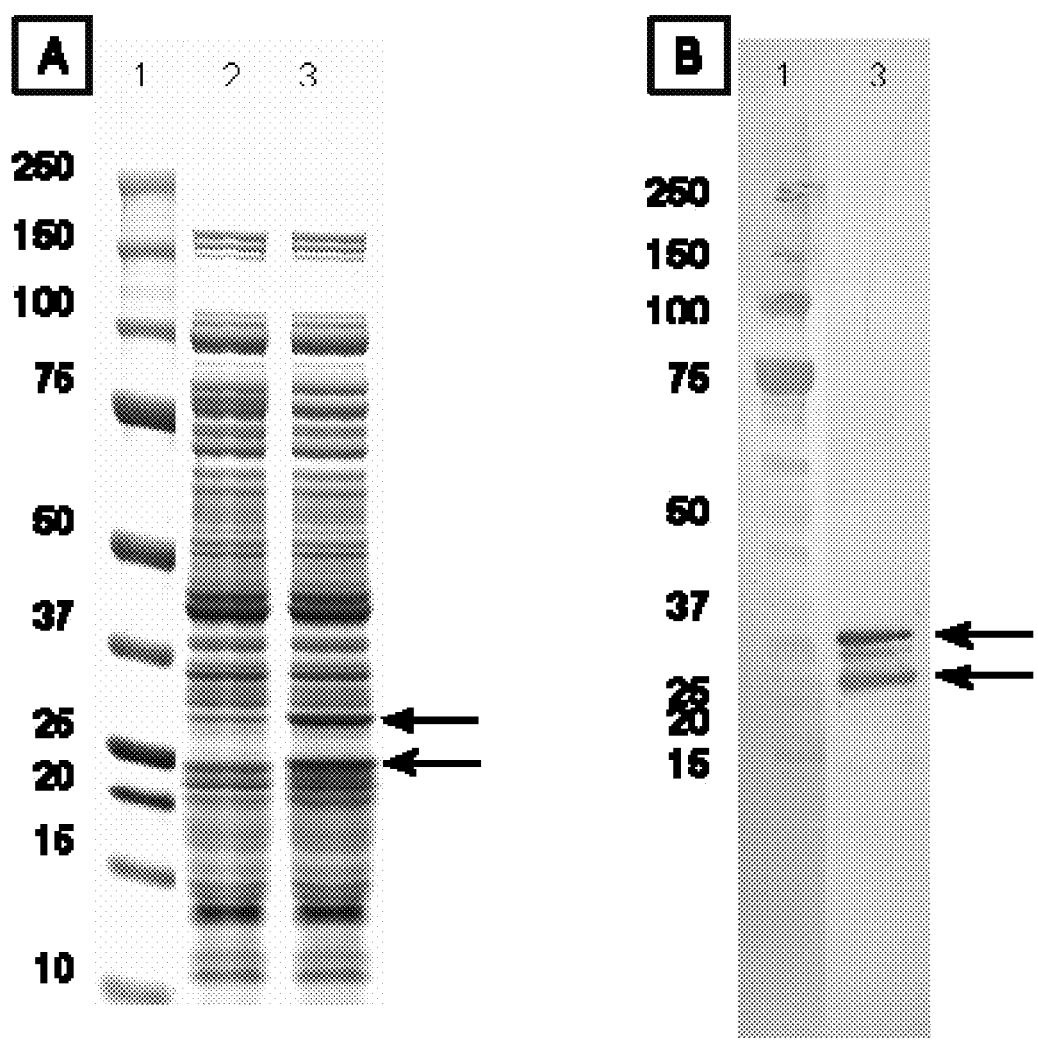

FIG. 8. Analysis of the expression of *Lawsonia intracellularis* gene 4320 using RTS500 technology by SDS-PAGE (A) and Western blotting using anti-polyhistidine monoclonal (B). Lane 1, molecular weight marker; lane 2, control; lane 3, pET4320 Arrows indicate the location of the expression product.

Figure 9:
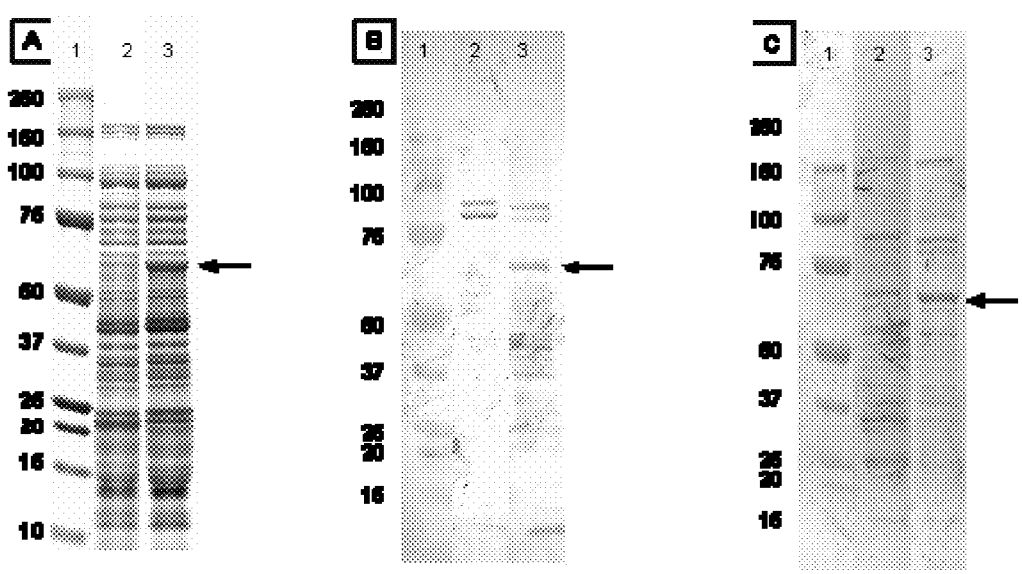

FIG. 9. Analysis of the expression of *Lawsonia intracellularis* gene 2008 using RTS500 technology by SDS-PAGE (A) and Western blotting with polyclonal pig serum (B). Lane 1, molecular weight marker; lane 2, control; lane 3, pET2008 Arrows indicate the location of the expression product.

The invention claimed is:

1. An isolated *Lawsonia intracellularis* protein, or an immunogenic fragment thereof, selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18.

2. Diagnostic test for the detection of antibodies against *Lawsonia intracellularis*, wherein said test comprises a protein or a fragment thereof as defined in claim 1.

3. Diagnostic test for the detection of antigenic material of *Lawsonia intracellularis*, wherein said test comprises antibodies against a protein or a fragment thereof as defined in claim 1.

4. A vaccine for combating *Lawsonia intracellularis* infection, comprising at least one protein according to claim 1, and a pharmaceutically acceptable carrier.

5. The isolated protein of claim 1, consisting of SEQ ID NO: 2.

6. An isolated nucleic acid selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, and SEQ ID NO: 17.

7. The isolated nucleic acid of claim 6, consisting of SEQ ID NO: 1.

* * * * *

SEQUENCE LISTING

<160> NUMBER OF SEQ ID NOS: 18

<210> SEQ ID NO 1
<211> LENGTH: 2088
<212> TYPE: DNA
<213> ORGANISM: Lawsonia intracellularis

```
<220> FEATURE:
<221> NAME/KEY: CDS
<222> LOCATION: (16)..(2085)

<400> SEQUENCE: 1
cggaggttga ttact atg agt ctt aca gca gga atg tgg aca ggt gtt tca      51
               Met Ser Leu Thr Ala Gly Met Trp Thr Gly Val Ser
                 1               5                  10 gga ctt tta agt cat ggc gaa aag atg aat gtt att ggt aat aac ata       99
Gly Leu Leu Ser His Gly Glu Lys Met Asn Val Ile Gly Asn Asn Ile
         15                  20                  25 gct aac gta aat aca gta ggc ttt aaa ggc caa cgt atg gat ttc gca     147
Ala Asn Val Asn Thr Val Gly Phe Lys Gly Gln Arg Met Asp Phe Ala
 30                  35                  40 gac ttt att tat caa gat ggc ttt agt act gca ggg att aca caa att     195
Asp Phe Ile Tyr Gln Asp Gly Phe Ser Thr Ala Gly Ile Thr Gln Ile
 45                  50                  55                  60 gga cgt ggt gta ggc att gga gct gtc atg ggg aac ttt ggt cag ggt     243
Gly Arg Gly Val Gly Ile Gly Ala Val Met Gly Asn Phe Gly Gln Gly
                 65                  70                  75 agt ttt gaa acc aca act gaa gca aca gac ctt gct att ggt ggt cgt     291
Ser Phe Glu Thr Thr Thr Glu Ala Thr Asp Leu Ala Ile Gly Gly Arg
         80                  85                  90 gga ttt ttc aaa gtt aaa cca caa gga tca gag act tca tat tat acc     339
Gly Phe Phe Lys Val Lys Pro Gln Gly Ser Glu Thr Ser Tyr Tyr Thr
 95                 100                 105 cgt gca ggt aat ttt cgt ttt aat aat gat gga tac tta gtt gat cct     387
Arg Ala Gly Asn Phe Arg Phe Asn Asn Asp Gly Tyr Leu Val Asp Pro
                110                 115                 120 cat gga tat gct ctt cag ggt tgg aaa att gat aat act gaa ggg cca     435
His Gly Tyr Ala Leu Gln Gly Trp Lys Ile Asp Asn Thr Glu Gly Pro
125                 130                 135                 140 caa cgt atc tca ggt ggt gtt aat cca ggt aca aat act tcg cag att     483
Gln Arg Ile Ser Gly Gly Val Asn Pro Gly Thr Asn Thr Ser Gln Ile
                145                 150                 155 atg ggt aca ggt gaa cca aca gat atc cgt ctt gat act tgg aca gtt     531
Met Gly Thr Gly Glu Pro Thr Asp Ile Arg Leu Asp Thr Trp Thr Val
                160                 165                 170 gca cct tta cag aca aca aat gta agt ttt aac gta aac ctt tct tct     579
Ala Pro Leu Gln Thr Thr Asn Val Ser Phe Asn Val Asn Leu Ser Ser
        175                 180                 185 gat aaa tct gga gat aaa tct caa aac gtt aat agt cca ttt acc tca     627
Asp Lys Ser Gly Asp Lys Ser Gln Asn Val Asn Ser Pro Phe Thr Ser
190                 195                 200 tta ttt aat ata tgg aat ggt aaa caa cca agt gaa cct aac aat cca     675
Leu Phe Asn Ile Trp Asn Gly Lys Gln Pro Ser Glu Pro Asn Asn Pro
205                 210                 215                 220 cct atg cct gaa agt gca tat agt tat cag aca tct att aag gta tat     723
Pro Met Pro Glu Ser Ala Tyr Ser Tyr Gln Thr Ser Ile Lys Val Tyr
                225                 230                 235 gat gaa gct ggt gga aca cat aca tta aca gtc tat ttt gac caa gtt     771
Asp Glu Ala Gly Gly Thr His Thr Leu Thr Val Tyr Phe Asp Gln Val
                240                 245                 250 tct cct aaa gac tac aaa ggt ggt gga agt gga gaa agt gta tgg gaa     819
Ser Pro Lys Asp Tyr Lys Gly Gly Gly Ser Gly Glu Ser Val Trp Glu
        255                 260                 265 tac gtt gtt act atg gat cct tct gaa gat aat cgc caa gtt tct gtt     867
Tyr Val Val Thr Met Asp Pro Ser Glu Asp Asn Arg Gln Val Ser Val
        270                 275                 280 ggt ggt aac att gtg gac atc aaa gat act aaa gct gca gga atg tta     915
Gly Gly Asn Ile Val Asp Ile Lys Asp Thr Lys Ala Ala Gly Met Leu
```

```
              285                 290                 295                 300
atg tca gga aca ttg agt ttt gat agc tca gga aaa ctt gca aac caa        963
Met Ser Gly Thr Leu Ser Phe Asp Ser Ser Gly Lys Leu Ala Asn Gln
                    305                 310                 315 agt gca tat tcg ctg aat ggt tca cgt aag cct gca gtt gat cct gca       1011
Ser Ala Tyr Ser Leu Asn Gly Ser Arg Lys Pro Ala Val Asp Pro Ala
                320                 325                 330 acc gga gct ctt att aat ggt aat ggt ttt act att gat aga gat gga       1059
Thr Gly Ala Leu Ile Asn Gly Asn Gly Phe Thr Ile Asp Arg Asp Gly
            335                 340                 345 aat gca att cct att ctt aat ata gat aat cca gct gaa aac ttc tat       1107
Asn Ala Ile Pro Ile Leu Asn Ile Asp Asn Pro Ala Glu Asn Phe Tyr
        350                 355                 360 cca gca gaa gtt tct aat aat gga ttt cct atg att gta gct aat ttt       1155
Pro Ala Glu Val Ser Asn Asn Gly Phe Pro Met Ile Val Ala Asn Phe
365                 370                 375                 380 act ggt gtc cca ggt aaa aat aca gct gga tct gtt ggt gat gct acc       1203
Thr Gly Val Pro Gly Lys Asn Thr Ala Gly Ser Val Gly Asp Ala Thr
                    385                 390                 395 acc ttt ttt aca gaa att gac ttt ggt tta aaa gct act gat ctt gat       1251
Thr Phe Phe Thr Glu Ile Asp Phe Gly Leu Lys Ala Thr Asp Leu Asp
                400                 405                 410 aat aca tgg aag aat gca aat gaa cct ctt tct tct tta agc tat aaa       1299
Asn Thr Trp Lys Asn Ala Asn Glu Pro Leu Ser Ser Leu Ser Tyr Lys
            415                 420                 425 aaa aca cat aat cct atg gat gtc gca ggt ggt tgg aca gtt ggt ggg       1347
Lys Thr His Asn Pro Met Asp Val Ala Gly Gly Trp Thr Val Gly Gly
        430                 435                 440 tat aaa act cca gct cca tca gta act gaa ctt ggt atg gct cag ata       1395
Tyr Lys Thr Pro Ala Pro Ser Val Thr Glu Leu Gly Met Ala Gln Ile
445                 450                 455                 460 ttg gaa aat cct gct ggg gta atg cca caa tat tat ttt ggt aac cct       1443
Leu Glu Asn Pro Ala Gly Val Met Pro Gln Tyr Tyr Phe Gly Asn Pro
                    465                 470                 475 aac tat gat aac aca gtt cca cag agt cca cca tat gta tat aaa aat       1491
Asn Tyr Asp Asn Thr Val Pro Gln Ser Pro Pro Tyr Val Tyr Lys Asn
                480                 485                 490 gaa gct tct tat cag gct gca tat aag act gca tta act gcc gca ggt       1539
Glu Ala Ser Tyr Gln Ala Ala Tyr Lys Thr Ala Leu Thr Ala Ala Gly
            495                 500                 505 ggt acc gca gct gac att aaa aag gaa cat tgg cct cat aat gct gca       1587
Gly Thr Ala Ala Asp Ile Lys Lys Glu His Trp Pro His Asn Ala Ala
        510                 515                 520 tca ggt ata tta gaa gct aat gat cca cca aat gtt aaa gac tta gct       1635
Ser Gly Ile Leu Glu Ala Asn Asp Pro Pro Asn Val Lys Asp Leu Ala
525                 530                 535                 540 aat atg aat gga aca cca aac cgc tta tca aat gcg ttt act aac tat       1683
Asn Met Asn Gly Thr Pro Asn Arg Leu Ser Asn Ala Phe Thr Asn Tyr
                    545                 550                 555 gca ggt ggt agc tct aca aaa tct gca agt caa aat ggt tat ggt ttt       1731
Ala Gly Gly Ser Ser Thr Lys Ser Ala Ser Gln Asn Gly Tyr Gly Phe
                560                 565                 570 ggt gat tta atg aac tat agt gta aat gct gag gga gtg tta ttt gga       1779
Gly Asp Leu Met Asn Tyr Ser Val Asn Ala Glu Gly Val Leu Phe Gly
            575                 580                 585 gta tat tca aat gga gta caa ctt cca tta tat caa gta gct ctt tat       1827
Val Tyr Ser Asn Gly Val Gln Leu Pro Leu Tyr Gln Val Ala Leu Tyr
        590                 595                 600 gat ttt aac tct aaa cag ggg tta cgt cgt gaa ggt ggt aac tta ttt       1875
Asp Phe Asn Ser Lys Gln Gly Leu Arg Arg Glu Gly Gly Asn Leu Phe
```

```
                605                    610                   615                   620
agt caa aca aga gaa tca ggg gac cca tct tca ggt gct gca aac act        1923
Ser Gln Thr Arg Glu Ser Gly Asp Pro Ser Ser Gly Ala Ala Asn Thr
            625                   630                   635 tct ggg ttt ggt tca att aac gct aat act tta gaa gga tca aac gta        1971
Ser Gly Phe Gly Ser Ile Asn Ala Asn Thr Leu Glu Gly Ser Asn Val
            640                   645                   650 gat ata tct aca gag ttt gtc tca atg att gca aca caa cgt gga ttc        2019
Asp Ile Ser Thr Glu Phe Val Ser Met Ile Ala Thr Gln Arg Gly Phe
            655                   660                   665 cag tca aat agt aaa att gta act act att gac caa atg tta gag aca        2067
Gln Ser Asn Ser Lys Ile Val Thr Thr Ile Asp Gln Met Leu Glu Thr
            670                   675                   680 gtt gta aat atg aag cgt tag                                             2088
Val Val Asn Met Lys Arg
685             690

<210> SEQ ID NO 2
<211> LENGTH: 690
<212> TYPE: PRT
<213> ORGANISM: Lawsonia intracellularis

<400> SEQUENCE: 2

Met Ser Leu Thr Ala Gly Met Trp Thr Gly Val Ser Gly Leu Leu Ser
1               5                   10                  15

His Gly Glu Lys Met Asn Val Ile Gly Asn Asn Ile Ala Asn Val Asn
            20                  25                  30

Thr Val Gly Phe Lys Gly Gln Arg Met Asp Phe Ala Asp Phe Ile Tyr
        35                  40                  45

Gln Asp Gly Phe Ser Thr Ala Gly Ile Thr Gln Ile Gly Arg Gly Val
    50                  55                  60

Gly Ile Gly Ala Val Met Gly Asn Phe Gly Gln Gly Ser Phe Glu Thr
65                  70                  75                  80

Thr Thr Glu Ala Thr Asp Leu Ala Ile Gly Gly Arg Gly Phe Phe Lys
                85                  90                  95

Val Lys Pro Gln Gly Ser Glu Thr Ser Tyr Tyr Thr Arg Ala Gly Asn
            100                 105                 110

Phe Arg Phe Asn Asn Asp Gly Tyr Leu Val Asp Pro His Gly Tyr Ala
        115                 120                 125

Leu Gln Gly Trp Lys Ile Asp Asn Thr Glu Gly Pro Gln Arg Ile Ser
    130                 135                 140

Gly Gly Val Asn Pro Gly Thr Asn Thr Ser Gln Ile Met Gly Thr Gly
145                 150                 155                 160

Glu Pro Thr Asp Ile Arg Leu Asp Thr Trp Thr Val Ala Pro Leu Gln
                165                 170                 175

Thr Thr Asn Val Ser Phe Asn Val Asn Leu Ser Ser Asp Lys Ser Gly
            180                 185                 190

Asp Lys Ser Gln Asn Val Asn Ser Pro Phe Thr Ser Leu Phe Asn Ile
        195                 200                 205

Trp Asn Gly Lys Gln Pro Ser Glu Pro Asn Asn Pro Met Pro Glu
    210                 215                 220

Ser Ala Tyr Ser Tyr Gln Thr Ser Ile Lys Val Tyr Asp Glu Ala Gly
225                 230                 235                 240

Gly Thr His Thr Leu Thr Val Tyr Phe Asp Gln Val Ser Pro Lys Asp
                245                 250                 255

Tyr Lys Gly Gly Gly Ser Gly Glu Ser Val Trp Glu Tyr Val Val Thr
            260                 265                 270
```

```
Met Asp Pro Ser Glu Asp Asn Arg Gln Val Ser Val Gly Gly Asn Ile
            275                 280                 285

Val Asp Ile Lys Asp Thr Lys Ala Ala Gly Met Leu Met Ser Gly Thr
        290                 295                 300

Leu Ser Phe Asp Ser Ser Gly Lys Leu Ala Asn Gln Ser Ala Tyr Ser
305                 310                 315                 320

Leu Asn Gly Ser Arg Lys Pro Ala Val Asp Pro Ala Thr Gly Ala Leu
                325                 330                 335

Ile Asn Gly Asn Gly Phe Thr Ile Asp Arg Asp Gly Asn Ala Ile Pro
            340                 345                 350

Ile Leu Asn Ile Asp Asn Pro Ala Glu Asn Phe Tyr Pro Ala Glu Val
        355                 360                 365

Ser Asn Asn Gly Phe Pro Met Ile Val Ala Asn Phe Gly Val Pro
    370                 375                 380

Gly Lys Asn Thr Ala Gly Ser Val Gly Asp Ala Thr Thr Phe Phe Thr
385                 390                 395                 400

Glu Ile Asp Phe Gly Leu Lys Ala Thr Asp Leu Asp Asn Thr Trp Lys
                405                 410                 415

Asn Ala Asn Glu Pro Leu Ser Ser Leu Ser Tyr Lys Lys Thr His Asn
            420                 425                 430

Pro Met Asp Val Ala Gly Gly Trp Thr Val Gly Gly Tyr Lys Thr Pro
        435                 440                 445

Ala Pro Ser Val Thr Glu Leu Gly Met Ala Gln Ile Leu Glu Asn Pro
    450                 455                 460

Ala Gly Val Met Pro Gln Tyr Tyr Phe Gly Asn Pro Asn Tyr Asp Asn
465                 470                 475                 480

Thr Val Pro Gln Ser Pro Pro Tyr Val Tyr Lys Asn Glu Ala Ser Tyr
                485                 490                 495

Gln Ala Ala Tyr Lys Thr Ala Leu Thr Ala Ala Gly Gly Thr Ala Ala
            500                 505                 510

Asp Ile Lys Lys Glu His Trp Pro His Asn Ala Ala Ser Gly Ile Leu
        515                 520                 525

Glu Ala Asn Asp Pro Pro Asn Val Lys Asp Leu Ala Asn Met Asn Gly
    530                 535                 540

Thr Pro Asn Arg Leu Ser Asn Ala Phe Thr Asn Tyr Ala Gly Gly Ser
545                 550                 555                 560

Ser Thr Lys Ser Ala Ser Gln Asn Gly Tyr Gly Phe Gly Asp Leu Met
                565                 570                 575

Asn Tyr Ser Val Asn Ala Glu Gly Val Leu Phe Gly Val Tyr Ser Asn
            580                 585                 590

Gly Val Gln Leu Pro Leu Tyr Gln Val Ala Leu Tyr Asp Phe Asn Ser
        595                 600                 605

Lys Gln Gly Leu Arg Arg Glu Gly Gly Asn Leu Phe Ser Gln Thr Arg
    610                 615                 620

Glu Ser Gly Asp Pro Ser Ser Gly Ala Ala Asn Thr Ser Gly Phe Gly
625                 630                 635                 640

Ser Ile Asn Ala Asn Thr Leu Glu Gly Ser Asn Val Asp Ile Ser Thr
                645                 650                 655

Glu Phe Val Ser Met Ile Ala Thr Gln Arg Gly Phe Gln Ser Asn Ser
            660                 665                 670

Lys Ile Val Thr Thr Ile Asp Gln Met Leu Glu Thr Val Val Asn Met
        675                 680                 685

Lys Arg
```

-continued

690

<210> SEQ ID NO 3
<211> LENGTH: 751
<212> TYPE: DNA
<213> ORGANISM: Lawsonia intracellularis
<220> FEATURE:
<221> NAME/KEY: CDS
<222> LOCATION: (32)..(715)

<400> SEQUENCE: 3

```
aagagttacc ctagcgttag gagctaacaa c atg ttt cgt atg att gtt ttt        52
                                  Met Phe Arg Met Ile Val Phe
                                  1               5 ttt act gta ggt atc att atg ctt att ctt gct tgc tta gct gca ctt       100
Phe Thr Val Gly Ile Ile Met Leu Ile Leu Ala Cys Leu Ala Ala Leu
         10                  15                  20 gag ttc ata caa gat ttt ccc aat agc tat caa gaa gat gga caa atg       148
Glu Phe Ile Gln Asp Phe Pro Asn Ser Tyr Gln Glu Asp Gly Gln Met
 25                  30                  35 gtt aca gga att att tca aaa ata ata ggc tct aac tgt gat aat tct       196
Val Thr Gly Ile Ile Ser Lys Ile Ile Gly Ser Asn Cys Asp Asn Ser
40                  45                  50                  55 tca aca tct gat ata aat aat aag aaa tcc ata gat aga gat aaa gat       244
Ser Thr Ser Asp Ile Asn Asn Lys Lys Ser Ile Asp Arg Asp Lys Asp
                 60                  65                  70 aca tta ctc tca agt agt aat aga aat aca ata caa gcc ggt act cca       292
Thr Leu Leu Ser Ser Ser Asn Arg Asn Thr Ile Gln Ala Gly Thr Pro
             75                  80                  85 cat caa gaa aat aac ata aaa gaa gat ctt caa ctg act aac aaa aat       340
His Gln Glu Asn Asn Ile Lys Glu Asp Leu Gln Leu Thr Asn Lys Asn
         90                  95                 100 gaa caa aca act cca gaa gaa gaa gaa gaa agt aaa ttt att tgg tta       388
Glu Gln Thr Thr Pro Glu Glu Glu Glu Glu Ser Lys Phe Ile Trp Leu
105                 110                 115 aca gaa gct cca tca gag ctt aaa aaa gga gaa aaa gct ata aca caa       436
Thr Glu Ala Pro Ser Glu Leu Lys Lys Gly Glu Lys Ala Ile Thr Gln
120                 125                 130                 135 aca aga ttg tct att ggt aag gat ata tct ttt aga att act gct gat       484
Thr Arg Leu Ser Ile Gly Lys Asp Ile Ser Phe Arg Ile Thr Ala Asp
                140                 145                 150 gat gcc atc aaa gct caa tca atg atg tta aaa aat cca gat agg ttt       532
Asp Ala Ile Lys Ala Gln Ser Met Met Leu Lys Asn Pro Asp Arg Phe
            155                 160                 165 gtt tta gat ctt caa gga aag tgg ggt att tcc ctt cca cct att cca       580
Val Leu Asp Leu Gln Gly Lys Trp Gly Ile Ser Leu Pro Pro Ile Pro
        170                 175                 180 cct aca aat cct tgg tta aaa aaa ata cgc tta ggt act aat aat gga       628
Pro Thr Asn Pro Trp Leu Lys Lys Ile Arg Leu Gly Thr Asn Asn Gly
    185                 190                 195 aat aca cga ctt gtc ttt gat ctt caa aaa aaa cca tct aaa act gaa       676
Asn Thr Arg Leu Val Phe Asp Leu Gln Lys Lys Pro Ser Lys Thr Glu
200                 205                 210                 215 att aaa caa tta gat aca aat aaa att gaa atc caa att cattaaattg       725
Ile Lys Gln Leu Asp Thr Asn Lys Ile Glu Ile Gln Ile
                220                 225 catattagac aataagttat aataaa                                          751
```

<210> SEQ ID NO 4
<211> LENGTH: 228
<212> TYPE: PRT
<213> ORGANISM: Lawsonia intracellularis -continued

<400> SEQUENCE: 4

```
Met Phe Arg Met Ile Val Phe Phe Thr Val Gly Ile Ile Met Leu Ile
1               5                   10                  15

Leu Ala Cys Leu Ala Ala Leu Glu Phe Ile Gln Asp Phe Pro Asn Ser
            20                  25                  30

Tyr Gln Glu Asp Gly Gln Met Val Thr Gly Ile Ile Ser Lys Ile Ile
        35                  40                  45

Gly Ser Asn Cys Asp Asn Ser Ser Thr Ser Asp Ile Asn Asn Lys Lys
    50                  55                  60

Ser Ile Asp Arg Asp Lys Asp Thr Leu Leu Ser Ser Ser Asn Arg Asn
65                  70                  75                  80

Thr Ile Gln Ala Gly Thr Pro His Gln Glu Asn Asn Ile Lys Glu Asp
                85                  90                  95

Leu Gln Leu Thr Asn Lys Asn Glu Gln Thr Thr Pro Glu Glu Glu Glu
            100                 105                 110

Glu Ser Lys Phe Ile Trp Leu Thr Glu Ala Pro Ser Glu Leu Lys Lys
        115                 120                 125

Gly Glu Lys Ala Ile Thr Gln Thr Arg Leu Ser Ile Gly Lys Asp Ile
    130                 135                 140

Ser Phe Arg Ile Thr Ala Asp Asp Ala Ile Lys Ala Gln Ser Met Met
145                 150                 155                 160

Leu Lys Asn Pro Asp Arg Phe Val Leu Asp Leu Gly Lys Trp Gly
                165                 170                 175

Ile Ser Leu Pro Pro Ile Pro Pro Thr Asn Pro Trp Leu Lys Lys Ile
            180                 185                 190

Arg Leu Gly Thr Asn Asn Gly Asn Thr Arg Leu Val Phe Asp Leu Gln
        195                 200                 205

Lys Lys Pro Ser Lys Thr Glu Ile Lys Gln Leu Asp Thr Asn Lys Ile
    210                 215                 220

Glu Ile Gln Ile
225

<210> SEQ ID NO 5
<211> LENGTH: 1715
<212> TYPE: DNA
<213> ORGANISM: Lawsonia intracellularis
<220> FEATURE:
<221> NAME/KEY: CDS
<222> LOCATION: (34)..(1677)

<400> SEQUENCE: 5
```

```
aagctttggt aatagtttct aaggagttat tta atg cat caa aaa agt tgt tta       54
                                   Met His Gln Lys Ser Cys Leu
                                   1               5 gtt gct tta tgt att atg ttt att att atg gtg caa gtt ctt cag gca       102
Val Ala Leu Cys Ile Met Phe Ile Ile Met Val Gln Val Leu Gln Ala
            10                  15                  20 aat gca gct agc tat gtg gtt ttg cca ttt aaa gta aat gct cct cca       150
Asn Ala Ala Ser Tyr Val Val Leu Pro Phe Lys Val Asn Ala Pro Pro
    25                  30                  35 agc tat act tat ttg gaa aaa gct atc cca tct atg tta act tct aga       198
Ser Tyr Thr Tyr Leu Glu Lys Ala Ile Pro Ser Met Leu Thr Ser Arg
40                  45                  50                  55 ctt tat tgg gaa gaa cgt ttt caa cct atc ccg gat gct aat gct att       246
Leu Tyr Trp Glu Glu Arg Phe Gln Pro Ile Pro Asp Ala Asn Ala Ile
                60                  65                  70 aaa gca gga aag gta gaa gat ata aag gaa atg gat aag gca agg ata       294
```

```
                Lys Ala Gly Lys Val Glu Asp Ile Lys Glu Met Asp Lys Ala Arg Ile
                                 75                  80                  85 gct aca ggt gca gac tat ctt ata tgg gga cag gta aat att gta ggt       342
Ala Thr Gly Ala Asp Tyr Leu Ile Trp Gly Gln Val Asn Ile Val Gly
             90                  95                 100 gat gaa gct acg ctt gat gta caa gtt tgt gat ata gaa gga tca att       390
Asp Glu Ala Thr Leu Asp Val Gln Val Cys Asp Ile Glu Gly Ser Ile
        105                 110                 115 tgg agg aaa agt aaa aat aca aaa gtt gat aat tta att act gcc ctt       438
Trp Arg Lys Ser Lys Asn Thr Lys Val Asp Asn Leu Ile Thr Ala Leu
120             125                 130                 135 caa gat aca gca gat gca att aat agt gag ttg ttt ggg cgt gca act       486
Gln Asp Thr Ala Asp Ala Ile Asn Ser Glu Leu Phe Gly Arg Ala Thr
            140                 145                 150 aca aaa cca tca tca aaa gct act att gta gct caa atg aac tct gga       534
Thr Lys Pro Ser Ser Lys Ala Thr Ile Val Ala Gln Met Asn Ser Gly
                155                 160                 165 ttg att aag gga aaa gga aat gaa aat cag tca tat ctt aat cca gaa       582
Leu Ile Lys Gly Lys Gly Asn Glu Asn Gln Ser Tyr Leu Asn Pro Glu
            170                 175                 180 ttt cgt tat caa gga agc aat ctt tcc cgt ggc cga agt caa gct ctt       630
Phe Arg Tyr Gln Gly Ser Asn Leu Ser Arg Gly Arg Ser Gln Ala Leu
        185                 190                 195 ccc ttt gct tca gtt ggt ata gtt gtt ggt gac ttt ata gga gat aat       678
Pro Phe Ala Ser Val Gly Ile Val Val Gly Asp Phe Ile Gly Asp Asn
200             205                 210                 215 aaa aat gaa gtt gcc ata tta agt gag tat aaa gtc cat att tat cga       726
Lys Asn Glu Val Ala Ile Leu Ser Glu Tyr Lys Val His Ile Tyr Arg
            220                 225                 230 tgg gaa gaa gaa agg tta gct ctt ctt gga gaa tat aaa ttc cct cgc       774
Trp Glu Glu Glu Arg Leu Ala Leu Leu Gly Glu Tyr Lys Phe Pro Arg
        235                 240                 245 tca cta cag tct tta cat att cgt gct ttt gat gtg gat cat gat ggt       822
Ser Leu Gln Ser Leu His Ile Arg Ala Phe Asp Val Asp His Asp Gly
            250                 255                 260 gta cag gaa atc att gtt tct tgc ttt gat cct tca tat gca aag cca       870
Val Gln Glu Ile Ile Val Ser Cys Phe Asp Pro Ser Tyr Ala Lys Pro
265                 270                 275 tat tcg ttt att ctt agt ttt aaa aat aga gtg ttt aaa gag tta gcc       918
Tyr Ser Phe Ile Leu Ser Phe Lys Asn Arg Val Phe Lys Glu Leu Ala
280                 285                 290                 295 aca aac tta cca ttt tat tta aat gtg gtt aaa ctt cca cca gat ttt       966
Thr Asn Leu Pro Phe Tyr Leu Asn Val Val Lys Leu Pro Pro Asp Phe
            300                 305                 310 tct cct atg tta att ggt caa aag agt gac aat tca agg att ttt tct      1014
Ser Pro Met Leu Ile Gly Gln Lys Ser Asp Asn Ser Arg Ile Phe Ser
        315                 320                 325 ccc tct ggg gtt tat gaa ata gaa aaa cat gga cgt aac tat ata atg      1062
Pro Ser Gly Val Tyr Glu Ile Glu Lys His Gly Arg Asn Tyr Ile Met
            330                 335                 340 gga aat cgt ctt agt ctt cca aag gaa gct aat att ttt aat ttt tct      1110
Gly Asn Arg Leu Ser Leu Pro Lys Glu Ala Asn Ile Phe Asn Phe Ser
        345                 350                 355 tgg tta cca tca gat tca tta aaa gat gaa gaa gct aag tta gta ctt      1158
Trp Leu Pro Ser Asp Ser Leu Lys Asp Glu Glu Ala Lys Leu Val Leu
360                 365                 370                 375 gta acc aat aat gaa aga tta gtt gta tat aat aca aaa ggc aca aga      1206
Val Thr Asn Asn Glu Arg Leu Val Val Tyr Asn Thr Lys Gly Thr Arg
            380                 385                 390 ctt ttt atg act gaa gaa gtg tat tat ggt tct tct gtt ggt ata gac      1254
```

```
Leu Phe Met Thr Glu Glu Val Tyr Tyr Gly Ser Ser Val Gly Ile Asp
            395                 400                 405 gag ccc agt aat atg cct ggt ctt gga aag tca aaa gag ctt atc cct      1302
Glu Pro Ser Asn Met Pro Gly Leu Gly Lys Ser Lys Glu Leu Ile Pro
            410                 415                 420 tct aaa tat ttt atc cca gga cgg atg att cct att aat ctt gat tca      1350
Ser Lys Tyr Phe Ile Pro Gly Arg Met Ile Pro Ile Asn Leu Asp Ser
            425                 430                 435 atg ggg aaa tgg gag ttg ctt gta agc aag cca att tct gtt gca gca      1398
Met Gly Lys Trp Glu Leu Leu Val Ser Lys Pro Ile Ser Val Ala Ala
440                 445                 450                 455 aaa ttt ttt gaa aat tat aga tct ttt gct gaa ggc gaa att cag gct      1446
Lys Phe Phe Glu Asn Tyr Arg Ser Phe Ala Glu Gly Glu Ile Gln Ala
            460                 465                 470 tta aca tgg gac ggc tta gga tta ggt ctt gta tgg aat aca cgt cgt      1494
Leu Thr Trp Asp Gly Leu Gly Leu Gly Leu Val Trp Asn Thr Arg Arg
            475                 480                 485 att aag gga act att aca gat ttt gcc tta gct gat atg aat aat gat      1542
Ile Lys Gly Thr Ile Thr Asp Phe Ala Leu Ala Asp Met Asn Asn Asp
            490                 495                 500 ggg aag tta gac tta gtt gtt tcc gtt aat agc cat aca ggg att ctt      1590
Gly Lys Leu Asp Leu Val Val Ser Val Asn Ser His Thr Gly Ile Leu
            505                 510                 515 gga cta gaa aaa cga aag aca att ata gta ttt tat cct tta gag gta      1638
Gly Leu Glu Lys Arg Lys Thr Ile Ile Val Phe Tyr Pro Leu Glu Val
520                 525                 530                 535 gat aaa caa ggt atc cct aag gct gtt gaa gat aac taa ttttttccta       1687
Asp Lys Gln Gly Ile Pro Lys Ala Val Glu Asp Asn
            540                 545 ttaattattt ttttattctg atagttaa                                       1715

<210> SEQ ID NO 6
<211> LENGTH: 547
<212> TYPE: PRT
<213> ORGANISM: Lawsonia intracellularis

<400> SEQUENCE: 6

Met His Gln Lys Ser Cys Leu Val Ala Leu Cys Ile Met Phe Ile Ile
1               5                   10                  15

Met Val Gln Val Leu Gln Ala Asn Ala Ala Ser Tyr Val Leu Pro
            20                  25                  30

Phe Lys Val Asn Ala Pro Pro Ser Tyr Thr Tyr Leu Glu Lys Ala Ile
            35                  40                  45

Pro Ser Met Leu Thr Ser Arg Leu Tyr Trp Glu Glu Arg Phe Gln Pro
50                  55                  60

Ile Pro Asp Ala Asn Ala Ile Lys Ala Gly Lys Val Glu Asp Ile Lys
65                  70                  75                  80

Glu Met Asp Lys Ala Arg Ile Ala Thr Gly Ala Asp Tyr Leu Ile Trp
            85                  90                  95

Gly Gln Val Asn Ile Val Gly Asp Glu Ala Thr Leu Asp Val Gln Val
            100                 105                 110

Cys Asp Ile Glu Gly Ser Ile Trp Arg Lys Ser Lys Asn Thr Lys Val
            115                 120                 125

Asp Asn Leu Ile Thr Ala Leu Gln Asp Thr Ala Asp Ala Ile Asn Ser
            130                 135                 140

Glu Leu Phe Gly Arg Ala Thr Thr Lys Pro Ser Ser Lys Ala Thr Ile
145                 150                 155                 160

Val Ala Gln Met Asn Ser Gly Leu Ile Lys Gly Lys Gly Asn Glu Asn
```

```
                        165                 170                 175
    Gln Ser Tyr Leu Asn Pro Glu Phe Arg Tyr Gln Gly Ser Asn Leu Ser
                    180                 185                 190

Arg Gly Arg Ser Gln Ala Leu Pro Phe Ala Ser Val Gly Ile Val Val
                195                 200                 205

Gly Asp Phe Ile Gly Asp Asn Lys Asn Glu Val Ala Ile Leu Ser Glu
            210                 215                 220

Tyr Lys Val His Ile Tyr Arg Trp Glu Glu Arg Leu Ala Leu Leu
    225                 230                 235                 240

Gly Glu Tyr Lys Phe Pro Arg Ser Leu Gln Ser Leu His Ile Arg Ala
                    245                 250                 255

Phe Asp Val Asp His Asp Gly Val Gln Glu Ile Ile Val Ser Cys Phe
                260                 265                 270

Asp Pro Ser Tyr Ala Lys Pro Tyr Ser Phe Ile Leu Ser Phe Lys Asn
                275                 280                 285

Arg Val Phe Lys Glu Leu Ala Thr Asn Leu Pro Phe Tyr Leu Asn Val
            290                 295                 300

Val Lys Leu Pro Pro Asp Phe Ser Pro Met Leu Ile Gly Gln Lys Ser
    305                 310                 315                 320

Asp Asn Ser Arg Ile Phe Ser Pro Ser Gly Val Tyr Glu Ile Glu Lys
                    325                 330                 335

His Gly Arg Asn Tyr Ile Met Gly Asn Arg Leu Ser Leu Pro Lys Glu
                340                 345                 350

Ala Asn Ile Phe Asn Phe Ser Trp Leu Pro Ser Asp Ser Leu Lys Asp
                355                 360                 365

Glu Glu Ala Lys Leu Val Leu Val Thr Asn Asn Glu Arg Leu Val Val
            370                 375                 380

Tyr Asn Thr Lys Gly Thr Arg Leu Phe Met Thr Glu Glu Val Tyr Tyr
    385                 390                 395                 400

Gly Ser Ser Val Gly Ile Asp Glu Pro Ser Asn Met Pro Gly Leu Gly
                    405                 410                 415

Lys Ser Lys Glu Leu Ile Pro Ser Lys Tyr Phe Ile Pro Gly Arg Met
                420                 425                 430

Ile Pro Ile Asn Leu Asp Ser Met Gly Lys Trp Glu Leu Leu Val Ser
                435                 440                 445

Lys Pro Ile Ser Val Ala Ala Lys Phe Phe Glu Asn Tyr Arg Ser Phe
            450                 455                 460

Ala Glu Gly Glu Ile Gln Ala Leu Thr Trp Asp Gly Leu Gly Leu Gly
    465                 470                 475                 480

Leu Val Trp Asn Thr Arg Arg Ile Lys Gly Thr Ile Thr Asp Phe Ala
                    485                 490                 495

Leu Ala Asp Met Asn Asn Asp Gly Lys Leu Asp Leu Val Ser Val
                500                 505                 510

Asn Ser His Thr Gly Ile Leu Gly Leu Glu Lys Arg Lys Thr Ile Ile
                515                 520                 525

Val Phe Tyr Pro Leu Glu Val Asp Lys Gln Gly Ile Pro Lys Ala Val
            530                 535                 540

Glu Asp Asn
    545

<210> SEQ ID NO 7
    <211> LENGTH: 1564
    <212> TYPE: DNA
    <213> ORGANISM: Lawsonia intracellularis
    <220> FEATURE:
```

```
<221> NAME/KEY: CDS
<222> LOCATION: (41)..(1522)

<400> SEQUENCE: 7
agaagtatgt tctataagta gagtaaggaa tataaaaaat atg gtt agt tat att      55
                                             Met Val Ser Tyr Ile
                                             1               5 cgt tta tta gga agt ata ttt tta gta tta gca att ttt ggt tgt ggc     103
Arg Leu Leu Gly Ser Ile Phe Leu Val Leu Ala Ile Phe Gly Cys Gly
                10                  15                  20 gct cag ttt aat aaa ccc tct tta ctt gat gaa acc cct ata gat tac     151
Ala Gln Phe Asn Lys Pro Ser Leu Leu Asp Glu Thr Pro Ile Asp Tyr
            25                  30                  35 agt tct gta ctt tct gat tac ata gta gaa tta gaa aaa gaa cca ctt     199
Ser Ser Val Leu Ser Asp Tyr Ile Val Glu Leu Glu Lys Glu Pro Leu
        40                  45                  50 cag tat ata tta cta aaa aaa gaa aaa ttt tct caa atg gag ata tat     247
Gln Tyr Ile Leu Leu Lys Lys Glu Lys Phe Ser Gln Met Glu Ile Tyr
    55                  60                  65 aat tat caa ttc aca tca caa cat tgg tct cca gat aat ttt gta tca     295
Asn Tyr Gln Phe Thr Ser Gln His Trp Ser Pro Asp Asn Phe Val Ser
70                  75                  80                  85 cct gct ata tgg gaa cat cag gta gat ata tat atc cct cac cat cca     343
Pro Ala Ile Trp Glu His Gln Val Asp Ile Tyr Ile Pro His His Pro
                90                  95                  100 gtt tca gaa cgt gca ctt ctt atc atc aat aat ggt att aat aat ggt     391
Val Ser Glu Arg Ala Leu Leu Ile Ile Asn Asn Gly Ile Asn Asn Gly
            105                 110                 115 aca ttt ttt act tct cct aaa gct cca act gat ttt act cca gaa gta     439
Thr Phe Phe Thr Ser Pro Lys Ala Pro Thr Asp Phe Thr Pro Glu Val
        120                 125                 130 tta gaa gaa atc gct cgt tca aca aaa act gta gtc att gct cta agt     487
Leu Glu Glu Ile Ala Arg Ser Thr Lys Thr Val Val Ile Ala Leu Ser
135                 140                 145 gat atc cca aat cag tat ctt act tat aga ggt gac tgg aga ttt ctt     535
Asp Ile Pro Asn Gln Tyr Leu Thr Tyr Arg Gly Asp Trp Arg Phe Leu
150                 155                 160                 165 aag gaa gat gaa agt att gct atg agt tgg tct agt ttt tta caa gat     583
Lys Glu Asp Glu Ser Ile Ala Met Ser Trp Ser Ser Phe Leu Gln Asp
                170                 175                 180 cca gaa agt cgg tac aca aga cct ctc tat gtc cct atg gtt gca gca     631
Pro Glu Ser Arg Tyr Thr Arg Pro Leu Tyr Val Pro Met Val Ala Ala
            185                 190                 195 gtt tct cag gca atg act ctt gca gaa aag gag tta caa gca tta aaa     679
Val Ser Gln Ala Met Thr Leu Ala Glu Lys Glu Leu Gln Ala Leu Lys
        200                 205                 210 att aag cat ttt att gta tct ggt gtg tca aag cgt gga tgg aca aca     727
Ile Lys His Phe Ile Val Ser Gly Val Ser Lys Arg Gly Trp Thr Thr
215                 220                 225 tgg ctt tca gct att gct gac tca cga gta gat gct att acc ccg ttt     775
Trp Leu Ser Ala Ile Ala Asp Ser Arg Val Asp Ala Ile Thr Pro Phe
230                 235                 240                 245 gtt att gat gca ttg aat act cgg aaa gtc ctt gga cat atg tat aaa     823
Val Ile Asp Ala Leu Asn Thr Arg Lys Val Leu Gly His Met Tyr Lys
                250                 255                 260 aca tat gga aat aat tgg cct ata gca ttt tat cca tat tat aga ttt     871
Thr Tyr Gly Asn Asn Trp Pro Ile Ala Phe Tyr Pro Tyr Tyr Arg Phe
            265                 270                 275 gat tta gat aaa caa cta gat aca gtt cct ttt ttc aat ctt atg aat     919
Asp Leu Asp Lys Gln Leu Asp Thr Val Pro Phe Phe Asn Leu Met Asn
        280                 285                 290
```

```
att gtt gat cca tat aga tat tta gga aca cca tat aag tct cga ctt      967
Ile Val Asp Pro Tyr Arg Tyr Leu Gly Thr Pro Tyr Lys Ser Arg Leu
    295                 300                 305 gct atc cct aaa tat att gta aat gca agt gga gat gat ttt tat gtc     1015
Ala Ile Pro Lys Tyr Ile Val Asn Ala Ser Gly Asp Asp Phe Tyr Val
310                 315                 320                 325 cct gat aat tca agt ttt tac tat gat gat ctc cct gga gag aaa gca     1063
Pro Asp Asn Ser Ser Phe Tyr Tyr Asp Asp Leu Pro Gly Glu Lys Ala
                330                 335                 340 tta cgt ttt gca cca aac tca aat cat cat ggg ata tta aat ttc aca     1111
Leu Arg Phe Ala Pro Asn Ser Asn His His Gly Ile Leu Asn Phe Thr
            345                 350                 355 aaa caa tcg ctt att cct ttt gtg aat aga gta caa aaa ggt att tca     1159
Lys Gln Ser Leu Ile Pro Phe Val Asn Arg Val Gln Lys Gly Ile Ser
        360                 365                 370 acg cca gtt tta gat att tcc aca gag atg acg gaa cga gtt caa tat     1207
Thr Pro Val Leu Asp Ile Ser Thr Glu Met Thr Glu Arg Val Gln Tyr
    375                 380                 385 gtg act gtt cgt ttt tct gaa gtt cca gag aag ata gta ctt tgg aaa     1255
Val Thr Val Arg Phe Ser Glu Val Pro Glu Lys Ile Val Leu Trp Lys
390                 395                 400                 405 gca gca aat cca gag tca cga gat ttt cgt tat gcc tgt cgt gtt agg     1303
Ala Ala Asn Pro Glu Ser Arg Asp Phe Arg Tyr Ala Cys Arg Val Arg
                410                 415                 420 tac atg gaa aca cca tta cac ctt tct gca aca ggg gaa gtt agc gtt     1351
Tyr Met Glu Thr Pro Leu His Leu Ser Ala Thr Gly Glu Val Ser Val
            425                 430                 435 tca tta gag atc cct tct gta gga tgg caa gct gct ttt att gaa gct     1399
Ser Leu Glu Ile Pro Ser Val Gly Trp Gln Ala Ala Phe Ile Glu Ala
        440                 445                 450 aca ttt aaa gat ggt ttt gtt gca aca aca cca gtg tat att tta cca     1447
Thr Phe Lys Asp Gly Phe Val Ala Thr Thr Pro Val Tyr Ile Leu Pro
    455                 460                 465 aaa gat ata tat cca cct ata aaa ata cca cct gta cat gga tta tta     1495
Lys Asp Ile Tyr Pro Pro Ile Lys Ile Pro Pro Val His Gly Leu Leu
470                 475                 480                 485 tgt aag ttt gta cat ggt cga acc tag taactagtag ttgttgtact           1542
Cys Lys Phe Val His Gly Arg Thr
                490 gataatctaa aaggatatag at                                            1564

<210> SEQ ID NO 8
<211> LENGTH: 493
<212> TYPE: PRT
<213> ORGANISM: Lawsonia intracellularis

<400> SEQUENCE: 8

Met Val Ser Tyr Ile Arg Leu Leu Gly Ser Ile Phe Leu Val Leu Ala
1               5                   10                  15

Ile Phe Gly Cys Gly Ala Gln Phe Asn Lys Pro Ser Leu Leu Asp Glu
            20                  25                  30

Thr Pro Ile Asp Tyr Ser Ser Val Leu Ser Asp Tyr Ile Val Glu Leu
        35                  40                  45

Glu Lys Glu Pro Leu Gln Tyr Ile Leu Leu Lys Lys Glu Lys Phe Ser
    50                  55                  60

Gln Met Glu Ile Tyr Asn Tyr Gln Phe Thr Gln His Trp Ser Pro
65                  70                  75                  80

Asp Asn Phe Val Ser Pro Ala Ile Trp Glu His Gln Val Asp Ile Tyr
                85                  90                  95
```

Ile Pro His His Pro Val Ser Glu Arg Ala Leu Leu Ile Ile Asn Asn
            100                 105                 110

Gly Ile Asn Asn Gly Thr Phe Phe Thr Ser Pro Lys Ala Pro Thr Asp
        115                 120                 125

Phe Thr Pro Glu Val Leu Glu Glu Ile Ala Arg Ser Thr Lys Thr Val
130                 135                 140

Val Ile Ala Leu Ser Asp Ile Pro Asn Gln Tyr Leu Thr Tyr Arg Gly
145                 150                 155                 160

Asp Trp Arg Phe Leu Lys Glu Asp Glu Ser Ile Ala Met Ser Trp Ser
                165                 170                 175

Ser Phe Leu Gln Asp Pro Glu Ser Arg Tyr Thr Arg Pro Leu Tyr Val
            180                 185                 190

Pro Met Val Ala Ala Val Ser Gln Ala Met Thr Leu Ala Glu Lys Glu
        195                 200                 205

Leu Gln Ala Leu Lys Ile Lys His Phe Ile Val Ser Gly Val Ser Lys
    210                 215                 220

Arg Gly Trp Thr Thr Trp Leu Ser Ala Ile Ala Asp Ser Arg Val Asp
225                 230                 235                 240

Ala Ile Thr Pro Phe Val Ile Asp Ala Leu Asn Thr Arg Lys Val Leu
                245                 250                 255

Gly His Met Tyr Lys Thr Tyr Gly Asn Asn Trp Pro Ile Ala Phe Tyr
            260                 265                 270

Pro Tyr Tyr Arg Phe Asp Leu Asp Lys Gln Leu Asp Thr Val Pro Phe
        275                 280                 285

Phe Asn Leu Met Asn Ile Val Asp Pro Tyr Arg Tyr Leu Gly Thr Pro
    290                 295                 300

Tyr Lys Ser Arg Leu Ala Ile Pro Lys Tyr Ile Val Asn Ala Ser Gly
305                 310                 315                 320

Asp Asp Phe Tyr Val Pro Asp Asn Ser Ser Phe Tyr Tyr Asp Asp Leu
                325                 330                 335

Pro Gly Glu Lys Ala Leu Arg Phe Ala Pro Asn Ser Asn His His Gly
            340                 345                 350

Ile Leu Asn Phe Thr Lys Gln Ser Leu Ile Pro Phe Val Asn Arg Val
        355                 360                 365

Gln Lys Gly Ile Ser Thr Pro Val Leu Asp Ile Ser Thr Glu Met Thr
    370                 375                 380

Glu Arg Val Gln Tyr Val Thr Val Arg Phe Ser Glu Val Pro Glu Lys
385                 390                 395                 400

Ile Val Leu Trp Lys Ala Ala Asn Pro Glu Ser Arg Asp Phe Arg Tyr
                405                 410                 415

Ala Cys Arg Val Arg Tyr Met Glu Thr Pro Leu His Leu Ser Ala Thr
            420                 425                 430

Gly Glu Val Ser Val Ser Leu Glu Ile Pro Ser Val Gly Trp Gln Ala
        435                 440                 445

Ala Phe Ile Glu Ala Thr Phe Lys Asp Gly Phe Val Ala Thr Thr Pro
    450                 455                 460

Val Tyr Ile Leu Pro Lys Asp Ile Tyr Pro Pro Ile Lys Ile Pro Pro
465                 470                 475                 480

Val His Gly Leu Leu Cys Lys Phe Val His Gly Arg Thr
                485                 490

<210> SEQ ID NO 9
<211> LENGTH: 2096
<212> TYPE: DNA

```
<213> ORGANISM: Lawsonia intracellularis
<220> FEATURE:
<221> NAME/KEY: CDS
<222> LOCATION: (12)..(2096)

<400> SEQUENCE: 9
aggacaaaac t atg gcg gat tat ctt tca gga gga att tct ttt gga gga         50
           Met Ala Asp Tyr Leu Ser Gly Gly Ile Ser Phe Gly Gly
           1               5                   10 att ggt agt gga acc gat ttc caa gct atg att gat caa ctt aag aaa          98
Ile Gly Ser Gly Thr Asp Phe Gln Ala Met Ile Asp Gln Leu Lys Lys
        15                  20                  25 att gag ctt att cct aaa aat aga ctt gta gtt tcc cat gaa caa tgg         146
Ile Glu Leu Ile Pro Lys Asn Arg Leu Val Val Ser His Glu Gln Trp
 30                  35                  40                  45 aca aaa aaa tat aaa gca ttt gaa gag ctt ata aaa aca gtt aaa gat         194
Thr Lys Lys Tyr Lys Ala Phe Glu Glu Leu Ile Lys Thr Val Lys Asp
                 50                  55                  60 act gaa gcg tct tta agt aag cta agt tct gtt ggt gct att tta aaa         242
Thr Glu Ala Ser Leu Ser Lys Leu Ser Ser Val Gly Ala Ile Leu Lys
             65                  70                  75 aaa gaa ggt tct gtt tca aat act tct gtt gca agc gtt aag gca agt         290
Lys Glu Gly Ser Val Ser Asn Thr Ser Val Ala Ser Val Lys Ala Ser
         80                  85                  90 tct gat gca tct gat gga aca cat aca att gat gtg aaa cag ctt gca         338
Ser Asp Ala Ser Asp Gly Thr His Thr Ile Asp Val Lys Gln Leu Ala
     95                 100                 105 aca aac acg att ctt tct aat aat cat att ttt gat tct aaa act gaa         386
Thr Asn Thr Ile Leu Ser Asn Asn His Ile Phe Asp Ser Lys Thr Glu
110                 115                 120                 125 agt att aat aat aca ggt tca cct ggt atc ttt gct tat gag tat aaa         434
Ser Ile Asn Asn Thr Gly Ser Pro Gly Ile Phe Ala Tyr Glu Tyr Lys
                130                 135                 140 ggg gaa cta cat gaa gtt gaa gtt cct cca ggt agt gat ctt gaa tat         482
Gly Glu Leu His Glu Val Glu Val Pro Pro Gly Ser Asp Leu Glu Tyr
            145                 150                 155 ctt gca aca tta ata aac aaa gat tct aat aat cct ggt gtt aaa gca         530
Leu Ala Thr Leu Ile Asn Lys Asp Ser Asn Asn Pro Gly Val Lys Ala
        160                 165                 170 aac ctt atc aag act ggc gat ggc tat atg ttt agt ctt gaa gga act         578
Asn Leu Ile Lys Thr Gly Asp Gly Tyr Met Phe Ser Leu Glu Gly Thr
    175                 180                 185 gaa act ggt gca aat gcg act tta tct att tca aat aag aca acg ctt         626
Glu Thr Gly Ala Asn Ala Thr Leu Ser Ile Ser Asn Lys Thr Thr Leu
190                 195                 200                 205 cca gac ttt aaa gca tct gtt gct acc agc agt gca tta gct aat ggt         674
Pro Asp Phe Lys Ala Ser Val Ala Thr Ser Ser Ala Leu Ala Asn Gly
                210                 215                 220 gaa gat aca att att aat act tca gga aca act caa caa ttt tct ttt         722
Glu Asp Thr Ile Ile Asn Thr Ser Gly Thr Thr Gln Gln Phe Ser Phe
            225                 230                 235 gaa tac aat gga aga aca ttt act ttc gat att cct tca gga aca aca         770
Glu Tyr Asn Gly Arg Thr Phe Thr Phe Asp Ile Pro Ser Gly Thr Thr
        240                 245                 250 gca aaa gaa ctc caa aca gct ata aat gaa aat aca aaa aat aca gga         818
Ala Lys Glu Leu Gln Thr Ala Ile Asn Glu Asn Thr Lys Asn Thr Gly
    255                 260                 265 gta cgt gca act ttt gaa aaa cat ggc tca gat ata gta ttg caa tta         866
Val Arg Ala Thr Phe Glu Lys His Gly Ser Asp Ile Val Leu Gln Leu
270                 275                 280                 285 gaa gga aca gtt cct aat caa caa gtt aaa gta acc gct agc cct act         914
```

-continued

```
         Glu Gly Thr Val Pro Asn Gln Gln Val Lys Val Thr Ala Ser Pro Thr
                         290                 295                 300 gat ctt gga agt ttc aca tct tcg ggt caa gca ggc tgg aat aaa cgt          962
Asp Leu Gly Ser Phe Thr Ser Ser Gly Gln Ala Gly Trp Asn Lys Arg
            305                 310                 315 gat tct caa gat gct att ttt aat att aat ggt tgg gac caa gaa ctt         1010
Asp Ser Gln Asp Ala Ile Phe Asn Ile Asn Gly Trp Asp Gln Glu Leu
        320                 325                 330 aca tct tct aca aat gaa ctt aca gaa gtt atc cca gga ctt caa att        1058
Thr Ser Ser Thr Asn Glu Leu Thr Glu Val Ile Pro Gly Leu Gln Ile
    335                 340                 345 aca cta ctt tcc gaa ggg aaa aca caa att aca att cag act tct act        1106
Thr Leu Leu Ser Glu Gly Lys Thr Gln Ile Thr Ile Gln Thr Ser Thr
350                 355                 360                 365 gac gaa gta aaa aaa caa gtt gag aaa gca gta gag tct ata aat aat        1154
Asp Glu Val Lys Lys Gln Val Glu Lys Ala Val Glu Ser Ile Asn Asn
                370                 375                 380 gtt ctt tcc aaa att caa gag tta act aaa gca aca gct gaa gac aaa        1202
Val Leu Ser Lys Ile Gln Glu Leu Thr Lys Ala Thr Ala Glu Asp Lys
            385                 390                 395 gat gat agt aaa gac act tct agt tct tca agt aaa att cca tca tat        1250
Asp Asp Ser Lys Asp Thr Ser Ser Ser Ser Lys Ile Pro Ser Tyr
        400                 405                 410 tta caa agt cct aca aaa gtg aag gct gga cta ttt aca ggt gat act        1298
Leu Gln Ser Pro Thr Lys Val Lys Ala Gly Leu Phe Thr Gly Asp Thr
    415                 420                 425 ggc ata caa atg ctt agt act aga ctt aag tct atc ttt tct tct aat        1346
Gly Ile Gln Met Leu Ser Thr Arg Leu Lys Ser Ile Phe Ser Ser Asn
430                 435                 440                 445 ggt cta ggt ttt tct cct aaa caa aca caa gat ggt cca ggg gat cta        1394
Gly Leu Gly Phe Ser Pro Lys Gln Thr Gln Asp Gly Pro Gly Asp Leu
                450                 455                 460 ttt tca tca ctt gct tca att ggt att gtc gta gat gct gat gag ggt        1442
Phe Ser Ser Leu Ala Ser Ile Gly Ile Val Val Asp Ala Asp Glu Gly
            465                 470                 475 agt gaa act ttt gga caa ctt aaa att tta gat aga gaa aca att ggt        1490
Ser Glu Thr Phe Gly Gln Leu Lys Ile Leu Asp Arg Glu Thr Ile Gly
        480                 485                 490 cct gat gca cct tat aca act ctt gat gag gca tta aaa aaa gat cca        1538
Pro Asp Ala Pro Tyr Thr Thr Leu Asp Glu Ala Leu Lys Lys Asp Pro
    495                 500                 505 caa gca gta gca gat ata tta gct ggt agt tct gga ata tct gat tca        1586
Gln Ala Val Ala Asp Ile Leu Ala Gly Ser Ser Gly Ile Ser Asp Ser
510                 515                 520                 525 aca gat ttt tct tat caa gat cat att gtt gga aaa aca caa gct ggt        1634
Thr Asp Phe Ser Tyr Gln Asp His Ile Val Gly Lys Thr Gln Ala Gly
                530                 535                 540 aca tat gat gta aag tat tct gta gat gca agt ggt act ata gga gac        1682
Thr Tyr Asp Val Lys Tyr Ser Val Asp Ala Ser Gly Thr Ile Gly Asp
            545                 550                 555 gtt tac att gga ggt gta aaa gct tct cta tct gat cct gca aaa aat        1730
Val Tyr Ile Gly Gly Val Lys Ala Ser Leu Ser Asp Pro Ala Lys Asn
        560                 565                 570 ata tat acg gtc aca tct ggt cct gct aca ggt ctt agt ata gca gtt        1778
Ile Tyr Thr Val Thr Ser Gly Pro Ala Thr Gly Leu Ser Ile Ala Val
    575                 580                 585 aat aat cgt act cca ggt atc aat gta gaa agt act gta aga gtc aaa        1826
Asn Asn Arg Thr Pro Gly Ile Asn Val Glu Ser Thr Val Arg Val Lys
590                 595                 600                 605 caa ggt aaa ctt agc caa ata caa gaa gca ctt aaa gct gaa gta cag        1874
```

```
                Gln Gly Lys Leu Ser Gln Ile Gln Glu Ala Leu Lys Ala Glu Val Gln
                                610                 615                 620 caa gat cct tta aaa gaa aac aca ggt cct tta att atc atg caa gat       1922
Gln Asp Pro Leu Lys Glu Asn Thr Gly Pro Leu Ile Ile Met Gln Asp
            625                 630                 635 aac tat aag gat gtt atg aaa aat ctt gag aca aga ata gaa aaa gaa       1970
Asn Tyr Lys Asp Val Met Lys Asn Leu Glu Thr Arg Ile Glu Lys Glu
        640                 645                 650 aca caa aga gtt act agt tgg gaa cgt atg atg cgt tta aaa ttt tct       2018
Thr Gln Arg Val Thr Ser Trp Glu Arg Met Met Arg Leu Lys Phe Ser
    655                 660                 665 aga ctt gat gct gta tta gca aaa tat aat cag atg atg tca gca aat       2066
Arg Leu Asp Ala Val Leu Ala Lys Tyr Asn Gln Met Met Ser Ala Asn
670                 675                 680                 685 gct tct agt tta ggg caa ctt ggt gca taa                               2096
Ala Ser Ser Leu Gly Gln Leu Gly Ala
                690

<210> SEQ ID NO 10
<211> LENGTH: 694
<212> TYPE: PRT
<213> ORGANISM: Lawsonia intracellularis

<400> SEQUENCE: 10

Met Ala Asp Tyr Leu Ser Gly Gly Ile Ser Phe Gly Gly Ile Gly Ser
1               5                   10                  15

Gly Thr Asp Phe Gln Ala Met Ile Asp Gln Leu Lys Lys Ile Glu Leu
            20                  25                  30

Ile Pro Lys Asn Arg Leu Val Val Ser His Glu Gln Trp Thr Lys Lys
        35                  40                  45

Tyr Lys Ala Phe Glu Glu Leu Ile Lys Thr Val Lys Asp Thr Glu Ala
    50                  55                  60

Ser Leu Ser Lys Leu Ser Ser Val Gly Ala Ile Leu Lys Lys Glu Gly
65                  70                  75                  80

Ser Val Ser Asn Thr Ser Val Ala Ser Val Lys Ala Ser Ser Asp Ala
                85                  90                  95

Ser Asp Gly Thr His Thr Ile Asp Val Lys Gln Leu Ala Thr Asn Thr
            100                 105                 110

Ile Leu Ser Asn Asn His Ile Phe Asp Ser Lys Thr Glu Ser Ile Asn
        115                 120                 125

Asn Thr Gly Ser Pro Gly Ile Phe Ala Tyr Glu Tyr Lys Gly Glu Leu
    130                 135                 140

His Glu Val Glu Val Pro Pro Gly Ser Asp Leu Glu Tyr Leu Ala Thr
145                 150                 155                 160

Leu Ile Asn Lys Asp Ser Asn Asn Pro Gly Val Lys Ala Asn Leu Ile
                165                 170                 175

Lys Thr Gly Asp Gly Tyr Met Phe Ser Leu Glu Gly Thr Glu Thr Gly
            180                 185                 190

Ala Asn Ala Thr Leu Ser Ile Ser Asn Lys Thr Thr Leu Pro Asp Phe
        195                 200                 205

Lys Ala Ser Val Ala Thr Ser Ser Ala Leu Ala Asn Gly Glu Asp Thr
    210                 215                 220

Ile Ile Asn Thr Ser Gly Thr Thr Gln Gln Phe Ser Phe Glu Tyr Asn
225                 230                 235                 240

Gly Arg Thr Phe Thr Phe Asp Ile Pro Ser Gly Thr Thr Ala Lys Glu
                245                 250                 255

Leu Gln Thr Ala Ile Asn Glu Asn Thr Lys Asn Thr Gly Val Arg Ala
```

-continued

```
                260                 265                 270
Thr Phe Glu Lys His Gly Ser Asp Ile Val Leu Gln Leu Glu Gly Thr
            275                 280                 285
Val Pro Asn Gln Gln Val Lys Val Thr Ala Ser Pro Thr Asp Leu Gly
        290                 295                 300
Ser Phe Thr Ser Ser Gly Gln Ala Gly Trp Asn Lys Arg Asp Ser Gln
305                 310                 315                 320
Asp Ala Ile Phe Asn Ile Asn Gly Trp Asp Gln Glu Leu Thr Ser Ser
                325                 330                 335
Thr Asn Glu Leu Thr Glu Val Ile Pro Gly Leu Gln Ile Thr Leu Leu
            340                 345                 350
Ser Glu Gly Lys Thr Gln Ile Thr Ile Gln Thr Ser Thr Asp Glu Val
        355                 360                 365
Lys Lys Gln Val Glu Lys Ala Val Glu Ser Ile Asn Asn Val Leu Ser
    370                 375                 380
Lys Ile Gln Glu Leu Thr Lys Ala Thr Ala Glu Asp Lys Asp Ser
385                 390                 395                 400
Lys Asp Thr Ser Ser Ser Ser Lys Ile Pro Ser Tyr Leu Gln Ser
                405                 410                 415
Pro Thr Lys Val Lys Ala Gly Leu Phe Thr Gly Asp Thr Gly Ile Gln
            420                 425                 430
Met Leu Ser Thr Arg Leu Lys Ser Ile Phe Ser Ser Asn Gly Leu Gly
        435                 440                 445
Phe Ser Pro Lys Gln Thr Gln Asp Gly Pro Gly Asp Leu Phe Ser Ser
    450                 455                 460
Leu Ala Ser Ile Gly Ile Val Val Asp Ala Asp Glu Gly Ser Glu Thr
465                 470                 475                 480
Phe Gly Gln Leu Lys Ile Leu Asp Arg Glu Thr Ile Gly Pro Asp Ala
                485                 490                 495
Pro Tyr Thr Thr Leu Asp Glu Ala Leu Lys Lys Asp Pro Gln Ala Val
            500                 505                 510
Ala Asp Ile Leu Ala Gly Ser Ser Gly Ile Ser Asp Ser Thr Asp Phe
        515                 520                 525
Ser Tyr Gln Asp His Ile Val Gly Lys Thr Gln Ala Gly Thr Tyr Asp
    530                 535                 540
Val Lys Tyr Ser Val Asp Ala Ser Gly Thr Ile Gly Asp Val Tyr Ile
545                 550                 555                 560
Gly Gly Val Lys Ala Ser Leu Ser Asp Pro Ala Lys Asn Ile Tyr Thr
                565                 570                 575
Val Thr Ser Gly Pro Ala Thr Gly Leu Ser Ile Ala Val Asn Asn Arg
            580                 585                 590
Thr Pro Gly Ile Asn Val Glu Ser Thr Val Arg Val Lys Gln Gly Lys
        595                 600                 605
Leu Ser Gln Ile Gln Glu Ala Leu Lys Ala Glu Val Gln Gln Asp Pro
    610                 615                 620
Leu Lys Glu Asn Thr Gly Pro Leu Ile Ile Met Gln Asp Asn Tyr Lys
625                 630                 635                 640
Asp Val Met Lys Asn Leu Glu Thr Arg Ile Glu Lys Glu Thr Gln Arg
                645                 650                 655
Val Thr Ser Trp Glu Arg Met Met Arg Leu Lys Phe Ser Arg Leu Asp
            660                 665                 670
Ala Val Leu Ala Lys Tyr Asn Gln Met Met Ser Ala Asn Ala Ser Ser
        675                 680                 685
```

Leu Gly Gln Leu Gly Ala
690

<210> SEQ ID NO 11
<211> LENGTH: 1200
<212> TYPE: DNA
<213> ORGANISM: Lawsonia intracellularis
<220> FEATURE:
<221> NAME/KEY: CDS
<222> LOCATION: (13)..(1200)

<400> SEQUENCE: 11

| | | |
|---|---|---|
| taggagatag tt atg gct aat gtt agt gga atc cct gca cca cga tta ctt<br>Met Ala Asn Val Ser Gly Ile Pro Ala Pro Arg Leu Leu<br>1                      5                     10 | | 51 |
| tcc aca aca aat caa atg acc aat gca gct gct ggt aat act aat aga<br>Ser Thr Thr Asn Gln Met Thr Asn Ala Ala Ala Gly Asn Thr Asn Arg<br>15                    20                    25 | | 99 |
| gct acc ggt agt atg aac ggt cgt aat ctc aca caa ata aaa aca cct<br>Ala Thr Gly Ser Met Asn Gly Arg Asn Leu Thr Gln Ile Lys Thr Pro<br>30                    35                    40                    45 | | 147 |
| cag tcc atg att gat aat gct tca gaa gaa tta aca act tct ctt gaa<br>Gln Ser Met Ile Asp Asn Ala Ser Glu Glu Leu Thr Thr Ser Leu Glu<br>               50                    55                    60 | | 195 |
| tct aaa agc agt gac gac ttt gca att aaa gat cgt aaa aga caa ggg<br>Ser Lys Ser Ser Asp Asp Phe Ala Ile Lys Asp Arg Lys Arg Gln Gly<br>           65                    70                    75 | | 243 |
| aaa gga tct gat tct cta tta aaa atg gtt caa gaa tat aca gag ctg<br>Lys Gly Ser Asp Ser Leu Leu Lys Met Val Gln Glu Tyr Thr Glu Leu<br>80                    85                    90 | | 291 |
| acg aat gat gat acc cgt aat gct aaa aga gct atg tta tcc cag gta<br>Thr Asn Asp Asp Thr Arg Asn Ala Lys Arg Ala Met Leu Ser Gln Val<br>95                    100                 105 | | 339 |
| tta cgt gca agt caa agt tca caa gat gta ctc gaa aaa aca tta gaa<br>Leu Arg Ala Ser Gln Ser Ser Gln Asp Val Leu Glu Lys Thr Leu Glu<br>110                 115                120                125 | | 387 |
| caa ttt tct aat aaa aca gat gct tgg gct tct ctt gca gaa att gca<br>Gln Phe Ser Asn Lys Thr Asp Ala Trp Ala Ser Leu Ala Glu Ile Ala<br>                  130                 135                140 | | 435 |
| caa gaa tat ggt gca gaa tct cca cag cca aca gga tta aaa tct gta<br>Gln Glu Tyr Gly Ala Glu Ser Pro Gln Pro Thr Gly Leu Lys Ser Val<br>145               150                155 | | 483 |
| tta gat gct atg gag aca tta gaa aat gag ttt ggt gat gaa att aaa<br>Leu Asp Ala Met Glu Thr Leu Glu Asn Glu Phe Gly Asp Glu Ile Lys<br>                160                 165                170 | | 531 |
| gca gga cta aaa gga gct cta aat tca aaa gaa ttt act gat ata ggc<br>Ala Gly Leu Lys Gly Ala Leu Asn Ser Lys Glu Phe Thr Asp Ile Gly<br>175               180                185 | | 579 |
| agt gca gca cag tta aga gat ctt tat aca aca aca gta act ata aca<br>Ser Ala Ala Gln Leu Arg Asp Leu Tyr Thr Thr Thr Val Thr Ile Thr<br>190               195                200                205 | | 627 |
| gct gca cct gat gca gtg tta gca aga ctt ctt gaa gaa tat gag agt<br>Ala Ala Pro Asp Ala Val Leu Ala Arg Leu Leu Glu Glu Tyr Glu Ser<br>                  210                 215                220 | | 675 |
| gat gat gat ctg gat aga gcc att gat ttc ctt cta tct aca ctt ggt<br>Asp Asp Asp Leu Asp Arg Ala Ile Asp Phe Leu Leu Ser Thr Leu Gly<br>225               230                235 | | 723 |
| gga gag ctt gaa tca gct gat cca agt atg gat aaa gta cat ctt caa<br>Gly Glu Leu Glu Ser Ala Asp Pro Ser Met Asp Lys Val His Leu Gln<br>                240                 245                250 | | 771 |
| agt gta atg ggt gat att gaa aaa aca caa caa ctt cat agc tct cat<br>Ser Val Met Gly Asp Ile Glu Lys Thr Gln Gln Leu His Ser Ser His | | 819 |

```
     255                 260                 265
aaa caa tgt act aca gcc ctt agc agg tgg aaa gag aaa cat aaa ggt    867
Lys Gln Cys Thr Thr Ala Leu Ser Arg Trp Lys Glu Lys His Lys Gly
270                 275                 280                 285 ggg ggg gaa aat agt aca cta act cct tta gaa atg atg cgt gaa cta    915
Gly Gly Glu Asn Ser Thr Leu Thr Pro Leu Glu Met Met Arg Glu Leu
                290                 295                 300 att gca cta aaa aat gaa aat ttt att tct cct tcc tct ata gat aaa    963
Ile Ala Leu Lys Asn Glu Asn Phe Ile Ser Pro Ser Ser Ile Asp Lys
            305                 310                 315 att gtt gat caa gct gat ccc caa gat att gaa aaa gaa gtc ctt ttt   1011
Ile Val Asp Gln Ala Asp Pro Gln Asp Ile Glu Lys Glu Val Leu Phe
        320                 325                 330 tta caa gag atg tta gct gct gta aga aaa ttt ccc att atg gta ttt   1059
Leu Gln Glu Met Leu Ala Ala Val Arg Lys Phe Pro Ile Met Val Phe
    335                 340                 345 gat aat gtc gaa aat cgt gta aga gtt atg ggt gct gta caa gat gct   1107
Asp Asn Val Glu Asn Arg Val Arg Val Met Gly Ala Val Gln Asp Ala
350                 355                 360                 365 gtt gac gat gct gta aga aga gaa gat gaa ttc ctc ttt caa aaa gaa   1155
Val Asp Asp Ala Val Arg Arg Glu Asp Glu Phe Leu Phe Gln Lys Glu
                370                 375                 380 cat cct gat gta cca cta caa cca gat gaa aat aat ata caa taa       1200
His Pro Asp Val Pro Leu Gln Pro Asp Glu Asn Asn Ile Gln
            385                 390                 395

<210> SEQ ID NO 12
<211> LENGTH: 395
<212> TYPE: PRT
<213> ORGANISM: Lawsonia intracellularis

<400> SEQUENCE: 12

Met Ala Asn Val Ser Gly Ile Pro Ala Pro Arg Leu Leu Ser Thr Thr
1               5                   10                  15

Asn Gln Met Thr Asn Ala Ala Ala Gly Asn Thr Asn Arg Ala Thr Gly
            20                  25                  30

Ser Met Asn Gly Arg Asn Leu Thr Gln Ile Lys Thr Pro Gln Ser Met
        35                  40                  45

Ile Asp Asn Ala Ser Glu Glu Leu Thr Thr Ser Leu Glu Ser Lys Ser
    50                  55                  60

Ser Asp Asp Phe Ala Ile Lys Asp Arg Lys Arg Gln Gly Lys Gly Ser
65                  70                  75                  80

Asp Ser Leu Leu Lys Met Val Gln Glu Tyr Thr Glu Leu Thr Asn Asp
                85                  90                  95

Asp Thr Arg Asn Ala Lys Arg Ala Met Leu Ser Gln Val Leu Arg Ala
            100                 105                 110

Ser Gln Ser Ser Gln Asp Val Leu Glu Lys Thr Leu Glu Gln Phe Ser
        115                 120                 125

Asn Lys Thr Asp Ala Trp Ala Ser Leu Ala Glu Ile Ala Gln Glu Tyr
    130                 135                 140

Gly Ala Glu Ser Pro Gln Pro Thr Gly Leu Lys Ser Val Leu Asp Ala
145                 150                 155                 160

Met Glu Thr Leu Glu Asn Glu Phe Gly Asp Glu Ile Lys Ala Gly Leu
                165                 170                 175

Lys Gly Ala Leu Asn Ser Lys Glu Phe Thr Asp Ile Gly Ser Ala Ala
            180                 185                 190

Gln Leu Arg Asp Leu Tyr Thr Thr Thr Val Thr Ile Thr Ala Ala Pro
        195                 200                 205
```

```
Asp Ala Val Leu Ala Arg Leu Leu Glu Glu Tyr Glu Ser Asp Asp
    210                 215                 220

Leu Asp Arg Ala Ile Asp Phe Leu Leu Ser Thr Leu Gly Gly Glu Leu
225                 230                 235                 240

Glu Ser Ala Asp Pro Ser Met Asp Lys Val His Leu Gln Ser Val Met
                245                 250                 255

Gly Asp Ile Glu Lys Thr Gln Gln Leu His Ser Ser Lys Gln Cys
            260                 265                 270

Thr Thr Ala Leu Ser Arg Trp Lys Glu Lys His Lys Gly Gly Gly Glu
            275                 280                 285

Asn Ser Thr Leu Thr Pro Leu Glu Met Met Arg Glu Leu Ile Ala Leu
        290                 295                 300

Lys Asn Glu Asn Phe Ile Ser Pro Ser Ser Ile Asp Lys Ile Val Asp
305                 310                 315                 320

Gln Ala Asp Pro Gln Asp Ile Glu Lys Glu Val Leu Phe Leu Gln Glu
                325                 330                 335

Met Leu Ala Ala Val Arg Lys Phe Pro Ile Met Val Phe Asp Asn Val
            340                 345                 350

Glu Asn Arg Val Arg Val Met Gly Ala Val Gln Asp Ala Val Asp Asp
            355                 360                 365

Ala Val Arg Arg Glu Asp Glu Phe Leu Phe Gln Lys Glu His Pro Asp
    370                 375                 380

Val Pro Leu Gln Pro Asp Glu Asn Asn Ile Gln
385                 390                 395

<210> SEQ ID NO 13
<211> LENGTH: 1269
<212> TYPE: DNA
<213> ORGANISM: Lawsonia intracellularis
<220> FEATURE:
<221> NAME/KEY: CDS
<222> LOCATION: (32)..(1222)

<400> SEQUENCE: 13
tgttggaaat tctctctgga ggagtaaagc a atg aca aat ttt gga gat ata      52
                                   Met Thr Asn Phe Gly Asp Ile
                                    1               5 agc gga agc tcc gca aga atg agt agc ttg atg act ggt aca tcc ggt   100
Ser Gly Ser Ser Ala Arg Met Ser Ser Leu Met Thr Gly Thr Ser Gly
         10                  15                  20 gaa gaa gga ctt gaa gaa ctt gaa ggt ggt gtt cct aaa gag caa ggt   148
Glu Glu Gly Leu Glu Glu Leu Glu Gly Gly Val Pro Lys Glu Gln Gly
 25                  30                  35 ggt cca ggt aaa gga gat gct tca gag gct gct aaa ggt caa gca gca   196
Gly Pro Gly Lys Gly Asp Ala Ser Glu Ala Ala Lys Gly Gln Ala Ala
 40                  45                  50                  55 gca gat agt att aat tca gct ggt ggt act gaa aag cct gga gaa gtt   244
Ala Asp Ser Ile Asn Ser Ala Gly Gly Thr Glu Lys Pro Gly Glu Val
                 60                  65                  70 ggt gat aag gaa gat gta ggg gaa ggt ggc gaa ata cct gaa ggt ggt   292
Gly Asp Lys Glu Asp Val Gly Glu Gly Gly Glu Ile Pro Glu Gly Gly
             75                  80                  85 gaa ata cct gag ggt ggt gaa gaa gtt cca gag gaa ccc cca tat gtc   340
Glu Ile Pro Glu Gly Gly Glu Glu Val Pro Glu Glu Pro Pro Tyr Val
         90                  95                 100 cct cct cca ttg gtt gaa cca gct aaa atc agt aca gta aca gat ctc   388
Pro Pro Pro Leu Val Glu Pro Ala Lys Ile Ser Thr Val Thr Asp Leu
    105                 110                 115
```

```
agt acg tta atg gga tca cta cag ctg aca gag caa aaa aag aat gct    436
Ser Thr Leu Met Gly Ser Leu Gln Leu Thr Glu Gln Lys Lys Asn Ala
120                 125                 130                 135 gaa aaa aca gta aat gaa att aaa gca cag aat aaa gag caa caa gta    484
Glu Lys Thr Val Asn Glu Ile Lys Ala Gln Asn Lys Glu Gln Gln Val
        140                 145                 150 aag ttc caa gag caa att aaa aag att gag gat aat att gct gaa tct    532
Lys Phe Gln Glu Gln Ile Lys Lys Ile Glu Asp Asn Ile Ala Glu Ser
                155                 160                 165 aag aaa agt ggt ata ctt aag ttt ttc caa aag ttg ttt gca gtt att    580
Lys Lys Ser Gly Ile Leu Lys Phe Phe Gln Lys Leu Phe Ala Val Ile
            170                 175                 180 ggt gct gta cta gga gct att gga ggt gcg cta gct att gct gca ggt    628
Gly Ala Val Leu Gly Ala Ile Gly Gly Ala Leu Ala Ile Ala Ala Gly
185                 190                 195 gct gct tca ggt aac cca tta ttg gtt gct gca ggt att atg gct att    676
Ala Ala Ser Gly Asn Pro Leu Leu Val Ala Ala Gly Ile Met Ala Ile
200                 205                 210                 215 gta gct tca att gat gca gca atg tcg tcg cta tcg gat ggt aaa gtg    724
Val Ala Ser Ile Asp Ala Ala Met Ser Ser Leu Ser Asp Gly Lys Val
        220                 225                 230 tcc atc tca gca ggg att agt aag gct ctt gag gct atg gga gta cca    772
Ser Ile Ser Ala Gly Ile Ser Lys Ala Leu Glu Ala Met Gly Val Pro
                235                 240                 245 gca gaa aca gca caa tgg att gca ttt ggt ata cag tta gca atg att    820
Ala Glu Thr Ala Gln Trp Ile Ala Phe Gly Ile Gln Leu Ala Met Ile
            250                 255                 260 gca gtg act ata gct att ggt ttt gcc tct ggt ggt ggt gga gca atg    868
Ala Val Thr Ile Ala Ile Gly Phe Ala Ser Gly Gly Gly Gly Ala Met
265                 270                 275 gct gga gtg tca aaa ata gca gat atg ttt tca aag tct caa gat gta    916
Ala Gly Val Ser Lys Ile Ala Asp Met Phe Ser Lys Ser Gln Asp Val
280                 285                 290                 295 gct aag ttg gca cag atg att gaa aaa gct tct aaa ata gta caa atc    964
Ala Lys Leu Ala Gln Met Ile Glu Lys Ala Ser Lys Ile Val Gln Ile
        300                 305                 310 gct ggt tca gtt aat cag tct gct ata ggc ggt aca ggt att ggt aca    1012
Ala Gly Ser Val Asn Gln Ser Ala Ile Gly Gly Thr Gly Ile Gly Thr
                315                 320                 325 gct gta gtg caa agc aat ata aaa gct aat gaa tct gaa caa aaa gaa    1060
Ala Val Val Gln Ser Asn Ile Lys Ala Asn Glu Ser Glu Gln Lys Glu
            330                 335                 340 att gaa gct gct att gca aaa gtt aaa gct aag ata gag acg tta caa    1108
Ile Glu Ala Ala Ile Ala Lys Val Lys Ala Lys Ile Glu Thr Leu Gln
345                 350                 355 gac ttc ttt aaa aac caa atg gaa caa ttc aat gct ata atg aaa ata    1156
Asp Phe Phe Lys Asn Gln Met Glu Gln Phe Asn Ala Ile Met Lys Ile
360                 365                 370                 375 ata aca gat att att caa gat agc gtc aat aca aaa ata gct gtt caa    1204
Ile Thr Asp Ile Ile Gln Asp Ser Val Asn Thr Lys Ile Ala Val Gln
        380                 385                 390 cgt ggt gca cgt gag taa tacctttagt aaatacagtg actatactat           1252
Arg Gly Ala Arg Glu
            395 aatatataaa ttaataa                                                 1269

<210> SEQ ID NO 14
<211> LENGTH: 396
<212> TYPE: PRT
<213> ORGANISM: Lawsonia intracellularis
```

-continued

```
<400> SEQUENCE: 14

Met Thr Asn Phe Gly Asp Ile Ser Gly Ser Ala Arg Met Ser Ser
1               5                   10                  15

Leu Met Thr Gly Thr Ser Gly Glu Glu Gly Leu Glu Glu Leu Glu Gly
            20                  25                  30

Gly Val Pro Lys Glu Gln Gly Pro Gly Lys Gly Asp Ala Ser Glu
            35                  40                  45

Ala Ala Lys Gly Gln Ala Ala Asp Ser Ile Asn Ser Ala Gly Gly
        50                  55                  60

Thr Glu Lys Pro Gly Glu Val Gly Asp Lys Glu Asp Val Gly Glu Gly
65                  70                  75                  80

Gly Glu Ile Pro Glu Gly Gly Glu Ile Pro Glu Gly Gly Glu Val
            85                  90                  95

Pro Glu Glu Pro Pro Tyr Val Pro Pro Leu Val Glu Pro Ala Lys
            100                 105                 110

Ile Ser Thr Val Thr Asp Leu Ser Thr Leu Met Gly Ser Leu Gln Leu
            115                 120                 125

Thr Glu Gln Lys Lys Asn Ala Glu Lys Thr Val Asn Glu Ile Lys Ala
    130                 135                 140

Gln Asn Lys Glu Gln Gln Val Lys Phe Gln Glu Gln Ile Lys Lys Ile
145                 150                 155                 160

Glu Asp Asn Ile Ala Glu Ser Lys Ser Gly Ile Leu Lys Phe Phe
            165                 170                 175

Gln Lys Leu Phe Ala Val Ile Gly Ala Val Leu Gly Ala Ile Gly Gly
            180                 185                 190

Ala Leu Ala Ile Ala Ala Gly Ala Ser Gly Asn Pro Leu Leu Val
        195                 200                 205

Ala Ala Gly Ile Met Ala Ile Val Ala Ser Ile Asp Ala Ala Met Ser
    210                 215                 220

Ser Leu Ser Asp Gly Lys Val Ser Ile Ser Ala Gly Ile Ser Lys Ala
225                 230                 235                 240

Leu Glu Ala Met Gly Val Pro Ala Glu Thr Ala Gln Trp Ile Ala Phe
            245                 250                 255

Gly Ile Gln Leu Ala Met Ile Ala Val Thr Ile Ala Ile Gly Phe Ala
            260                 265                 270

Ser Gly Gly Gly Gly Ala Met Ala Gly Val Ser Lys Ile Ala Asp Met
        275                 280                 285

Phe Ser Lys Ser Gln Asp Val Ala Lys Leu Ala Gln Met Ile Glu Lys
290                 295                 300

Ala Ser Lys Ile Val Gln Ile Ala Gly Ser Val Asn Gln Ser Ala Ile
305                 310                 315                 320

Gly Gly Thr Gly Ile Gly Thr Ala Val Val Gln Ser Asn Ile Lys Ala
            325                 330                 335

Asn Glu Ser Glu Gln Lys Glu Ile Glu Ala Ala Ile Ala Lys Val Lys
        340                 345                 350

Ala Lys Ile Glu Thr Leu Gln Asp Phe Phe Lys Asn Gln Met Glu Gln
    355                 360                 365

Phe Asn Ala Ile Met Lys Ile Ile Thr Asp Ile Ile Gln Asp Ser Val
370                 375                 380

Asn Thr Lys Ile Ala Val Gln Arg Gly Ala Arg Glu
385                 390                 395

<210> SEQ ID NO 15
<211> LENGTH: 894
```

```
<212> TYPE: DNA
<213> ORGANISM: Lawsonia intracellularis
<220> FEATURE:
<221> NAME/KEY: CDS
<222> LOCATION: (13)..(894)

<400> SEQUENCE: 15
aggaggaatt at atg tct ctt gtc att aat aac aac ctg atg gcc gtc aat        51
           Met Ser Leu Val Ile Asn Asn Asn Leu Met Ala Val Asn
             1               5                  10 gct caa cgt aac tta agc aag tct tat gga gaa ctg agt tct tct gtt          99
Ala Gln Arg Asn Leu Ser Lys Ser Tyr Gly Glu Leu Ser Ser Ser Val
 15              20                  25 cga aaa ctt tct tca ggt ctt cgt gta gga act gct gct gat gac tca         147
Arg Lys Leu Ser Ser Gly Leu Arg Val Gly Thr Ala Ala Asp Asp Ser
30              35                  40                  45 gca ggg tta gcc att cga gaa ctc atg aga tct gac att gca aca aca         195
Ala Gly Leu Ala Ile Arg Glu Leu Met Arg Ser Asp Ile Ala Thr Thr
                50                  55                  60 caa caa gga ata cga aat gcg aat gat gct att tct atg att caa act         243
Gln Gln Gly Ile Arg Asn Ala Asn Asp Ala Ile Ser Met Ile Gln Thr
            65                  70                  75 gcg gat ggt gca ctt gga gtc atc gat gaa aag ctc att cga atg aaa         291
Ala Asp Gly Ala Leu Gly Val Ile Asp Glu Lys Leu Ile Arg Met Lys
80                  85                  90 gaa ctt gct gaa caa gct gct aca ggt aca tat aac tcc act cag cgt         339
Glu Leu Ala Glu Gln Ala Ala Thr Gly Thr Tyr Asn Ser Thr Gln Arg
 95                 100                 105 atg att att gac tct gaa tat caa gct atg gcc tca gaa att act cgt         387
Met Ile Ile Asp Ser Glu Tyr Gln Ala Met Ala Ser Glu Ile Thr Arg
110                 115                 120                 125 att gct aat gcg aca gaa ttt aat ggt ata aaa ctt ctt gat ggt tca         435
Ile Ala Asn Ala Thr Glu Phe Asn Gly Ile Lys Leu Leu Asp Gly Ser
                130                 135                 140 tta tca ggt aat cat gat ggg aaa aaa ata aat tca act ggt gca gta         483
Leu Ser Gly Asn His Asp Gly Lys Lys Ile Asn Ser Thr Gly Ala Val
            145                 150                 155 cgt atc cac ttt ggg aca tct aac agc tct gct gaa gat tac tat gat         531
Arg Ile His Phe Gly Thr Ser Asn Ser Ser Ala Glu Asp Tyr Tyr Asp
        160                 165                 170 att aaa att ggc ggc tct aca gct tct gca tta gga ctt ggt aat aca         579
Ile Lys Ile Gly Gly Ser Thr Ala Ser Ala Leu Gly Leu Gly Asn Thr
175                 180                 185 gta aaa ggt gcg ggt gct aca gtc tct act caa gct gca gca caa aat         627
Val Lys Gly Ala Gly Ala Thr Val Ser Thr Gln Ala Ala Ala Gln Asn
190                 195                 200                 205 gcc tta aaa gct ata gat aat gcc att gtt tca aaa gat aaa att cga         675
Ala Leu Lys Ala Ile Asp Asn Ala Ile Val Ser Lys Asp Lys Ile Arg
                210                 215                 220 gca cac ctt ggt gga tta caa aat aga ctt gaa gct aca gtt gat aat         723
Ala His Leu Gly Gly Leu Gln Asn Arg Leu Glu Ala Thr Val Asp Asn
            225                 230                 235 tta agt ata caa aat gaa aac tta caa gct gct gaa tct cgt ata tct         771
Leu Ser Ile Gln Asn Glu Asn Leu Gln Ala Ala Glu Ser Arg Ile Ser
        240                 245                 250 gat ata gat gta agc caa gaa atg aca caa ttt gta cgt aac caa ata         819
Asp Ile Asp Val Ser Gln Glu Met Thr Gln Phe Val Arg Asn Gln Ile
255                 260                 265 ctt aca caa aca ggt gtt gct atg ctt tca caa gct aat tct cta cca         867
Leu Thr Gln Thr Gly Val Ala Met Leu Ser Gln Ala Asn Ser Leu Pro
270                 275                 280                 285
```

```
cgt atg gct cag caa ctt att ggc taa                                 894
Arg Met Ala Gln Gln Leu Ile Gly
                290

<210> SEQ ID NO 16
<211> LENGTH: 293
<212> TYPE: PRT
<213> ORGANISM: Lawsonia intracellularis

<400> SEQUENCE: 16

Met Ser Leu Val Ile Asn Asn Asn Leu Met Ala Val Asn Ala Gln Arg
1               5                   10                  15

Asn Leu Ser Lys Ser Tyr Gly Glu Leu Ser Ser Ser Val Arg Lys Leu
            20                  25                  30

Ser Ser Gly Leu Arg Val Gly Thr Ala Ala Asp Asp Ser Ala Gly Leu
        35                  40                  45

Ala Ile Arg Glu Leu Met Arg Ser Asp Ile Ala Thr Thr Gln Gln Gly
    50                  55                  60

Ile Arg Asn Ala Asn Asp Ala Ile Ser Met Ile Gln Thr Ala Asp Gly
65                  70                  75                  80

Ala Leu Gly Val Ile Asp Glu Lys Leu Ile Arg Met Lys Glu Leu Ala
                85                  90                  95

Glu Gln Ala Ala Thr Gly Thr Tyr Asn Ser Thr Gln Arg Met Ile Ile
            100                 105                 110

Asp Ser Glu Tyr Gln Ala Met Ala Ser Glu Ile Thr Arg Ile Ala Asn
        115                 120                 125

Ala Thr Glu Phe Asn Gly Ile Lys Leu Leu Asp Gly Ser Leu Ser Gly
    130                 135                 140

Asn His Asp Gly Lys Lys Ile Asn Ser Thr Gly Ala Val Arg Ile His
145                 150                 155                 160

Phe Gly Thr Ser Asn Ser Ser Ala Glu Asp Tyr Tyr Asp Ile Lys Ile
                165                 170                 175

Gly Gly Ser Thr Ala Ser Ala Leu Gly Leu Gly Asn Thr Val Lys Gly
            180                 185                 190

Ala Gly Ala Thr Val Ser Thr Gln Ala Ala Ala Gln Asn Ala Leu Lys
        195                 200                 205

Ala Ile Asp Asn Ala Ile Val Ser Lys Asp Lys Ile Arg Ala His Leu
    210                 215                 220

Gly Gly Leu Gln Asn Arg Leu Glu Ala Thr Val Asp Asn Leu Ser Ile
225                 230                 235                 240

Gln Asn Glu Asn Leu Gln Ala Ala Glu Ser Arg Ile Ser Asp Ile Asp
                245                 250                 255

Val Ser Gln Glu Met Thr Gln Phe Val Arg Asn Gln Ile Leu Thr Gln
            260                 265                 270

Thr Gly Val Ala Met Leu Ser Gln Ala Asn Ser Leu Pro Arg Met Ala
        275                 280                 285

Gln Gln Leu Ile Gly
    290

<210> SEQ ID NO 17
<211> LENGTH: 2848
<212> TYPE: DNA
<213> ORGANISM: Lawsonia intracellularis
<220> FEATURE:
<221> NAME/KEY: CDS
<222> LOCATION: (29)..(2848)

<400> SEQUENCE: 17
```

```
accttaacta aaaaataaaa agaatatt atg tat aat ata att aat aag cat      52
                                  Met Tyr Asn Ile Ile Asn Lys His
                                  1               5 caa atc ata aaa att tta tta ttt tcc tta tgt gtt ttc ttt ttt aca    100
Gln Ile Ile Lys Ile Leu Leu Phe Ser Leu Cys Val Phe Phe Phe Thr
    10              15                  20 ctt aca gaa aaa caa aaa att tat gct gca gac gtc ttt ttt gag ggc    148
Leu Thr Glu Lys Gln Lys Ile Tyr Ala Ala Asp Val Phe Phe Glu Gly
25              30                  35                  40 aga acc gaa acc tta atc aat gta aac aaa cca ttt gat tct ttt ttt    196
Arg Thr Glu Thr Leu Ile Asn Val Asn Lys Pro Phe Asp Ser Phe Phe
                45                  50                  55 gga ggt tct gac tct aca ata gga acc ctt gaa aca gga cct act aat    244
Gly Gly Ser Asp Ser Thr Ile Gly Thr Leu Glu Thr Gly Pro Thr Asn
            60                  65                  70 ctt acc ttc aca aca gta gga gcc ttc cgc aat tct gtt ttc aga att    292
Leu Thr Phe Thr Thr Val Gly Ala Phe Arg Asn Ser Val Phe Arg Ile
        75                  80                  85 att ggt ggt ggt agg tct agt ttt aac aac cca aat aca gtt aaa ggc    340
Ile Gly Gly Gly Arg Ser Ser Phe Asn Asn Pro Asn Thr Val Lys Gly
    90                  95                  100 aat gtt act cta act gtt tat aat act gat gta gaa aga ata att ggt    388
Asn Val Thr Leu Thr Val Tyr Asn Thr Asp Val Glu Arg Ile Ile Gly
105             110                 115                 120 gca ggt atc agc aat aga gga ctt gta acc gtt act ggc tca gta aat    436
Ala Gly Ile Ser Asn Arg Gly Leu Val Thr Val Thr Gly Ser Val Asn
                125                 130                 135 atg aag cta gaa aat gtt tct gtt act aga gga att tat ggt ggt gtc    484
Met Lys Leu Glu Asn Val Ser Val Thr Arg Gly Ile Tyr Gly Gly Val
            140                 145                 150 tat act caa aat gga cat gta cta ggc tct atc aac atg cat ttg aaa    532
Tyr Thr Gln Asn Gly His Val Leu Gly Ser Ile Asn Met His Leu Lys
        155                 160                 165 aac gtc caa act cca cta tta ata ggt tct gga gta agc aat gga cct    580
Asn Val Gln Thr Pro Leu Leu Ile Gly Ser Gly Val Ser Asn Gly Pro
    170                 175                 180 aat cgt att act gta aat gga gac ata aac att gat gtt gaa gac tct    628
Asn Arg Ile Thr Val Asn Gly Asp Ile Asn Ile Asp Val Glu Asp Ser
185                 190                 195                 200 agg att caa tat gta aac att aca gga gaa gta gat gca gga ata aaa    676
Arg Ile Gln Tyr Val Asn Ile Thr Gly Glu Val Asp Ala Gly Ile Lys
                205                 210                 215 gga aat gct act cta act gta aaa aaa tct act gtt gag ctt ata aac    724
Gly Asn Ala Thr Leu Thr Val Lys Lys Ser Thr Val Glu Leu Ile Asn
            220                 225                 230 tct ggt aga ggt aat atc tta ggt aat ctc aaa ata tct ata gca gat    772
Ser Gly Arg Gly Asn Ile Leu Gly Asn Leu Lys Ile Ser Ile Ala Asp
        235                 240                 245 tca aat ata agg ggg tta tca cca gta gac ttt ggt tct tca gta tat    820
Ser Asn Ile Arg Gly Leu Ser Pro Val Asp Phe Gly Ser Ser Val Tyr
    250                 255                 260 ggg gac aca tct ata aat gta att aat tct cag att aat gat att act    868
Gly Asp Thr Ser Ile Asn Val Ile Asn Ser Gln Ile Asn Asp Ile Thr
265                 270                 275                 280 ctt ata cca agg gct ggt gga atg ctt gta ggt cct gtt acc cta gat    916
Leu Ile Pro Arg Ala Gly Gly Met Leu Val Gly Pro Val Thr Leu Asp
                285                 290                 295 atc aca agc agt act ata caa aat ata caa tgt ggg cct gtc agt caa    964
Ile Thr Ser Ser Thr Ile Gln Asn Ile Gln Cys Gly Pro Val Ser Gln
            300                 305                 310
```

```
aat aat caa ctt aac aca cta aat gta act gtt aat act agt aac att    1012
Asn Asn Gln Leu Asn Thr Leu Asn Val Thr Val Asn Thr Ser Asn Ile
        315                 320                 325 act aac tta aac ctt ggt agt gtc gaa ggt cat aca ata tca act aca    1060
Thr Asn Leu Asn Leu Gly Ser Val Glu Gly His Thr Ile Ser Thr Thr
330                 335                 340 gca act gtt act gat agt aat att act aac ctt aat gtc gga acc ttc    1108
Ala Thr Val Thr Asp Ser Asn Ile Thr Asn Leu Asn Val Gly Thr Phe
345                 350                 355                 360 aat gga ctt gga gta act gag aat gcc tct gta atc att aat agt ggc    1156
Asn Gly Leu Gly Val Thr Glu Asn Ala Ser Val Ile Ile Asn Ser Gly
                365                 370                 375 aat att act aac ctt aat gtc gga act aat gta ata gct gca gcc aca    1204
Asn Ile Thr Asn Leu Asn Val Gly Thr Asn Val Ile Ala Ala Ala Thr
        380                 385                 390 act att aat tcc tct gcg acc ata cac gac gga ctt att gca aac ctt    1252
Thr Ile Asn Ser Ser Ala Thr Ile His Asp Gly Leu Ile Ala Asn Leu
395                 400                 405 acc tta ggc tca caa ggt aat ggt cgt act atg ata gct aca gca aat    1300
Thr Leu Gly Ser Gln Gly Asn Gly Arg Thr Met Ile Ala Thr Ala Asn
410                 415                 420 gtt aat ggt gga act att gga tta tta act atg ggt tca gaa aac ttc    1348
Val Asn Gly Gly Thr Ile Gly Leu Leu Thr Met Gly Ser Glu Asn Phe
425                 430                 435                 440 ata cca ggc aca aga cca att act gaa tta gca ata cta aac atg tct    1396
Ile Pro Gly Thr Arg Pro Ile Thr Glu Leu Ala Ile Leu Asn Met Ser
                445                 450                 455 ggt gga tta att gaa aga att atc gta ggt aat gcc aac tct tca acc    1444
Gly Gly Leu Ile Glu Arg Ile Ile Val Gly Asn Ala Asn Ser Ser Thr
        460                 465                 470 ata aac ttt act cct ggg aag aga tca att gta aaa aca ata aat ggt    1492
Ile Asn Phe Thr Pro Gly Lys Arg Ser Ile Val Lys Thr Ile Asn Gly
475                 480                 485 cca gaa ctt cca tat tta gtt aac ata caa aaa ggt gct atg aca caa    1540
Pro Glu Leu Pro Tyr Leu Val Asn Ile Gln Lys Gly Ala Met Thr Gln
490                 495                 500 tgg ggc act aaa aat atg ccc ttt tta ttg gat aca aga aat tta atc    1588
Trp Gly Thr Lys Asn Met Pro Phe Leu Leu Asp Thr Arg Asn Leu Ile
505                 510                 515                 520 ttg tcc gga act ctg att acc tca aat att caa cta gct gat tta tct    1636
Leu Ser Gly Thr Leu Ile Thr Ser Asn Ile Gln Leu Ala Asp Leu Ser
                525                 530                 535 ata acc aat cta ttt gtt gct aat ggc ggt aca cta gta cct aga aaa    1684
Ile Thr Asn Leu Phe Val Ala Asn Gly Gly Thr Leu Val Pro Arg Lys
        540                 545                 550 tta ata cct ggg aac caa cct gtt ata cag ttt ctt gga ggt cct caa    1732
Leu Ile Pro Gly Asn Gln Pro Val Ile Gln Phe Leu Gly Gly Pro Gln
555                 560                 565 tca ctc tta gtt atc cat caa cca tta aaa gta aat tta agc tta tca    1780
Ser Leu Leu Val Ile His Gln Pro Leu Lys Val Asn Leu Ser Leu Ser
570                 575                 580 cca aaa ctt att gga agt agc atg gtg cca ctt gct ttt gtc tct caa    1828
Pro Lys Leu Ile Gly Ser Ser Met Val Pro Leu Ala Phe Val Ser Gln
585                 590                 595                 600 tct ttt tca tca cca gat ctt ttt gtt aaa caa act aga agt ggt ctc    1876
Ser Phe Ser Ser Pro Asp Leu Phe Val Lys Gln Thr Arg Ser Gly Leu
                605                 610                 615 att tgg agt gat ctt gag ttt gat cca aca aca tct att tgg tat gtt    1924
Ile Trp Ser Asp Leu Glu Phe Asp Pro Thr Thr Ser Ile Trp Tyr Val
        620                 625                 630
```

| | |
|---|---|
| aat aat atc caa gca tct caa gat ttt tac tct ttc tct att gct cgt<br>Asn Asn Ile Gln Ala Ser Gln Asp Phe Tyr Ser Phe Ser Ile Ala Arg<br>635 640 645 | 1972 |
| gag act act aac tgg cta aga caa caa cat ata tgg act cta caa aac<br>Glu Thr Thr Asn Trp Leu Arg Gln Gln His Ile Trp Thr Leu Gln Asn<br>650 655 660 | 2020 |
| cgt tca agt aaa ctt tta gac aac gaa cat tat gga cta tgg ata aat<br>Arg Ser Ser Lys Leu Leu Asp Asn Glu His Tyr Gly Leu Trp Ile Asn<br>665 670 675 680 | 2068 |
| gtt caa ggt gga cat gaa agt ctt gat act tct att ggt agc aaa gca<br>Val Gln Gly Gly His Glu Ser Leu Asp Thr Ser Ile Gly Ser Lys Ala<br>685 690 695 | 2116 |
| aaa atg cca tgg ata atg gca aca gca gga tat gac tat ctt caa caa<br>Lys Met Pro Trp Ile Met Ala Thr Ala Gly Tyr Asp Tyr Leu Gln Gln<br>700 705 710 | 2164 |
| cta cca agg tta gat atg aaa gcc ctt tat ggt ctt gct ttt ggt gct<br>Leu Pro Arg Leu Asp Met Lys Ala Leu Tyr Gly Leu Ala Phe Gly Ala<br>715 720 725 | 2212 |
| tct aaa ggt aaa agt aaa tgg tct agc gtc aac tct aca aaa aat gat<br>Ser Lys Gly Lys Ser Lys Trp Ser Ser Val Asn Ser Thr Lys Asn Asp<br>730 735 740 | 2260 |
| gct gag cta ggt atg gtt agt ggt tat gta ggt ctt atc cat aac aaa<br>Ala Glu Leu Gly Met Val Ser Gly Tyr Val Gly Leu Ile His Asn Lys<br>745 750 755 760 | 2308 |
| act ggg ctc tat agt aca ttg acc tta caa ctt gcg tct agt aaa tta<br>Thr Gly Leu Tyr Ser Thr Leu Thr Leu Gln Leu Ala Ser Ser Lys Leu<br>765 770 775 | 2356 |
| cat act aat tct aca ggg ttc tat aga aat ttt aaa tgg aca gaa aca<br>His Thr Asn Ser Thr Gly Phe Tyr Arg Asn Phe Lys Trp Thr Glu Thr<br>780 785 790 | 2404 |
| act cca aca gaa gca ctt gaa ctt gga tgg aaa tac act ttc aac aac<br>Thr Pro Thr Glu Ala Leu Glu Leu Gly Trp Lys Tyr Thr Phe Asn Asn<br>795 800 805 | 2452 |
| ggt att aaa atg aat cct cgt gga caa ctt att ttt gaa caa aca tct<br>Gly Ile Lys Met Asn Pro Arg Gly Gln Leu Ile Phe Glu Gln Thr Ser<br>810 815 820 | 2500 |
| aaa cac cat ttt gat tta gga att caa aat gat aag gct ata tta gat<br>Lys His His Phe Asp Leu Gly Ile Gln Asn Asp Lys Ala Ile Leu Asp<br>825 830 835 840 | 2548 |
| aaa agc cag tta ata aca agt tct ctt ggt att acc gtt gaa tat aag<br>Lys Ser Gln Leu Ile Thr Ser Ser Leu Gly Ile Thr Val Glu Tyr Lys<br>845 850 855 | 2596 |
| cta cca gtt acc aca cct att aat ctt tat gct ggt att gaa agg ata<br>Leu Pro Val Thr Thr Pro Ile Asn Leu Tyr Ala Gly Ile Glu Arg Ile<br>860 865 870 | 2644 |
| aaa ggt cag tct gga aac ttt gca att agt tcc cag agc ctt caa atg<br>Lys Gly Gln Ser Gly Asn Phe Ala Ile Ser Ser Gln Ser Leu Gln Met<br>875 880 885 | 2692 |
| aag ttc aag cat gac aat gat aca agt gta gtt aga gca aca ata ggt<br>Lys Phe Lys His Asp Asn Asp Thr Ser Val Val Arg Ala Thr Ile Gly<br>890 895 900 | 2740 |
| aca aat ata tta ttg gga gaa cat ttt aat att cac tgt gat ata ttt<br>Thr Asn Ile Leu Leu Gly Glu His Phe Asn Ile His Cys Asp Ile Phe<br>905 910 915 920 | 2788 |
| gga gat aaa gga aat gat aaa ggc att ggt ggg caa gca gga ttt aca<br>Gly Asp Lys Gly Asn Asp Lys Gly Ile Gly Gly Gln Ala Gly Phe Thr<br>925 930 935 | 2836 |
| tac aaa ttt taa<br>Tyr Lys Phe | 2848 |

<210> SEQ ID NO 18
<211> LENGTH: 939
<212> TYPE: PRT
<213> ORGANISM: Lawsonia intracellularis

<400> SEQUENCE: 18

```
Met Tyr Asn Ile Ile Asn Lys His Gln Ile Ile Lys Ile Leu Leu Phe
1               5                   10                  15

Ser Leu Cys Val Phe Phe Phe Thr Leu Thr Glu Lys Gln Lys Ile Tyr
            20                  25                  30

Ala Ala Asp Val Phe Phe Glu Gly Arg Thr Glu Thr Leu Ile Asn Val
        35                  40                  45

Asn Lys Pro Phe Asp Ser Phe Phe Gly Gly Ser Asp Ser Thr Ile Gly
    50                  55                  60

Thr Leu Glu Thr Gly Pro Thr Asn Leu Thr Phe Thr Thr Val Gly Ala
65                  70                  75                  80

Phe Arg Asn Ser Val Phe Arg Ile Ile Gly Gly Gly Arg Ser Ser Phe
                85                  90                  95

Asn Asn Pro Asn Thr Val Lys Gly Asn Val Thr Leu Thr Val Tyr Asn
            100                 105                 110

Thr Asp Val Glu Arg Ile Ile Gly Ala Gly Ile Ser Asn Arg Gly Leu
        115                 120                 125

Val Thr Val Thr Gly Ser Val Asn Met Lys Leu Glu Asn Val Ser Val
    130                 135                 140

Thr Arg Gly Ile Tyr Gly Gly Val Tyr Thr Gln Asn Gly His Val Leu
145                 150                 155                 160

Gly Ser Ile Asn Met His Leu Lys Asn Val Gln Thr Pro Leu Leu Ile
                165                 170                 175

Gly Ser Gly Val Ser Asn Gly Pro Asn Arg Ile Thr Val Asn Gly Asp
            180                 185                 190

Ile Asn Ile Asp Val Glu Asp Ser Arg Ile Gln Tyr Val Asn Ile Thr
        195                 200                 205

Gly Glu Val Asp Ala Gly Ile Lys Gly Asn Ala Thr Leu Thr Val Lys
    210                 215                 220

Lys Ser Thr Val Glu Leu Ile Asn Ser Gly Arg Gly Asn Ile Leu Gly
225                 230                 235                 240

Asn Leu Lys Ile Ser Ile Ala Asp Ser Asn Ile Arg Gly Leu Ser Pro
                245                 250                 255

Val Asp Phe Gly Ser Ser Val Tyr Gly Asp Thr Ser Ile Asn Val Ile
            260                 265                 270

Asn Ser Gln Ile Asn Asp Ile Thr Leu Ile Pro Arg Ala Gly Gly Met
        275                 280                 285

Leu Val Gly Pro Val Thr Leu Asp Ile Thr Ser Thr Ile Gln Asn
    290                 295                 300

Ile Gln Cys Gly Pro Val Ser Gln Asn Asn Gln Leu Asn Thr Leu Asn
305                 310                 315                 320

Val Thr Val Asn Thr Ser Asn Ile Thr Asn Leu Asn Leu Gly Ser Val
                325                 330                 335

Glu Gly His Thr Ile Ser Thr Thr Ala Thr Val Thr Asp Ser Asn Ile
            340                 345                 350

Thr Asn Leu Asn Val Gly Thr Phe Asn Gly Leu Gly Val Thr Glu Asn
        355                 360                 365

Ala Ser Val Ile Ile Asn Ser Gly Asn Ile Thr Asn Leu Asn Val Gly
    370                 375                 380

Thr Asn Val Ile Ala Ala Ala Thr Thr Ile Asn Ser Ser Ala Thr Ile
```

-continued

```
              385                 390                 395                 400

His Asp Gly Leu Ile Ala Asn Leu Thr Leu Gly Ser Gln Gly Asn Gly
                405                 410                 415

Arg Thr Met Ile Ala Thr Ala Asn Val Asn Gly Gly Thr Ile Gly Leu
                420                 425                 430

Leu Thr Met Gly Ser Glu Asn Phe Ile Pro Gly Thr Arg Pro Ile Thr
                435                 440                 445

Glu Leu Ala Ile Leu Asn Met Ser Gly Gly Leu Ile Glu Arg Ile Ile
                450                 455                 460

Val Gly Asn Ala Asn Ser Ser Thr Ile Asn Phe Thr Pro Gly Lys Arg
465                 470                 475                 480

Ser Ile Val Lys Thr Ile Asn Gly Pro Glu Leu Pro Tyr Leu Val Asn
                485                 490                 495

Ile Gln Lys Gly Ala Met Thr Gln Trp Gly Thr Lys Asn Met Pro Phe
                500                 505                 510

Leu Leu Asp Thr Arg Asn Leu Ile Leu Ser Gly Thr Leu Ile Thr Ser
                515                 520                 525

Asn Ile Gln Leu Ala Asp Leu Ser Ile Thr Asn Leu Phe Val Ala Asn
530                 535                 540

Gly Gly Thr Leu Val Pro Arg Lys Leu Ile Pro Gly Asn Gln Pro Val
545                 550                 555                 560

Ile Gln Phe Leu Gly Gly Pro Gln Ser Leu Val Ile His Gln Pro
                565                 570                 575

Leu Lys Val Asn Leu Ser Leu Ser Pro Lys Leu Ile Gly Ser Ser Met
                580                 585                 590

Val Pro Leu Ala Phe Val Ser Gln Ser Phe Ser Ser Pro Asp Leu Phe
                595                 600                 605

Val Lys Gln Thr Arg Ser Gly Leu Ile Trp Ser Asp Leu Glu Phe Asp
                610                 615                 620

Pro Thr Thr Ser Ile Trp Tyr Val Asn Ile Gln Ala Ser Gln Asp
625                 630                 635                 640

Phe Tyr Ser Phe Ser Ile Ala Arg Glu Thr Thr Asn Trp Leu Arg Gln
                645                 650                 655

Gln His Ile Trp Thr Leu Gln Asn Arg Ser Ser Lys Leu Leu Asp Asn
                660                 665                 670

Glu His Tyr Gly Leu Trp Ile Asn Val Gln Gly His Glu Ser Leu
                675                 680                 685

Asp Thr Ser Ile Gly Ser Lys Ala Lys Met Pro Trp Ile Met Ala Thr
                690                 695                 700

Ala Gly Tyr Asp Tyr Leu Gln Gln Leu Pro Arg Leu Asp Met Lys Ala
705                 710                 715                 720

Leu Tyr Gly Leu Ala Phe Gly Ala Ser Lys Gly Lys Ser Lys Trp Ser
                725                 730                 735

Ser Val Asn Ser Thr Lys Asn Asp Ala Glu Leu Gly Met Val Ser Gly
                740                 745                 750

Tyr Val Gly Leu Ile His Asn Lys Thr Gly Leu Tyr Ser Thr Leu Thr
                755                 760                 765

Leu Gln Leu Ala Ser Ser Lys Leu His Thr Asn Ser Thr Gly Phe Tyr
                770                 775                 780

Arg Asn Phe Lys Trp Thr Glu Thr Pro Thr Glu Ala Leu Glu Leu
785                 790                 795                 800

Gly Trp Lys Tyr Thr Phe Asn Asn Gly Ile Lys Met Asn Pro Arg Gly
                805                 810                 815
```

```
Gln Leu Ile Phe Glu Gln Thr Ser Lys His His Phe Asp Leu Gly Ile
            820                 825                 830

Gln Asn Asp Lys Ala Ile Leu Asp Lys Ser Gln Leu Ile Thr Ser Ser
        835                 840                 845

Leu Gly Ile Thr Val Glu Tyr Lys Leu Pro Val Thr Thr Pro Ile Asn
850                         855                 860

Leu Tyr Ala Gly Ile Glu Arg Ile Lys Gly Gln Ser Gly Asn Phe Ala
865                     870                 875                 880

Ile Ser Ser Gln Ser Leu Gln Met Lys Phe Lys His Asp Asn Asp Thr
                885                 890                 895

Ser Val Val Arg Ala Thr Ile Gly Thr Asn Ile Leu Leu Gly Glu His
            900                 905                 910

Phe Asn Ile His Cys Asp Ile Phe Gly Asp Lys Gly Asn Asp Lys Gly
        915                 920                 925

Ile Gly Gly Gln Ala Gly Phe Thr Tyr Lys Phe
930                     935
```